US010329581B2

(12) United States Patent
Narva et al.

(10) Patent No.: US 10,329,581 B2
(45) Date of Patent: Jun. 25, 2019

(54) RIBOSOMAL PROTEIN L40 (RPL40) NUCLEIC ACID MOLECULES THAT CONFER RESISTANCE TO COLEOPTERAN AND HEMIPTERAN PESTS

(71) Applicant: Dow AgroSciences LLC, Indianapolis, IN (US)

(72) Inventors: Kenneth E. Narva, Zionsville, IN (US); Elane Fishilevich, Indianapolis, IN (US); Murugesan Rangasamy, Zionsville, IN (US); Meghan L. Frey, Greenwood, IN (US); Wendy Lo, Indianapolis, IN (US); Sarah E. Worden, Indianapolis, IN (US); Premchand Gandra, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 5 days.

(21) Appl. No.: 15/376,771

(22) Filed: Dec. 13, 2016

(65) Prior Publication Data

US 2017/0175132 A1    Jun. 22, 2017

Related U.S. Application Data

(60) Provisional application No. 62/269,382, filed on Dec. 18, 2015.

(51) Int. Cl.
| | |
|---|---|
| *C12N 15/82* | (2006.01) |
| *A01H 4/00* | (2006.01) |
| *A01N 57/16* | (2006.01) |
| *C07K 14/195* | (2006.01) |
| *C07K 14/21* | (2006.01) |
| *C07K 14/32* | (2006.01) |
| *C12N 15/113* | (2010.01) |
| *C12Q 1/6895* | (2018.01) |
| *A01N 65/00* | (2009.01) |

(52) U.S. Cl.
CPC ......... *C12N 15/8286* (2013.01); *A01H 4/008* (2013.01); *A01N 57/16* (2013.01); *A01N 65/00* (2013.01); *C07K 14/195* (2013.01); *C07K 14/21* (2013.01); *C07K 14/32* (2013.01); *C12N 15/113* (2013.01); *C12N 15/8218* (2013.01); *C12N 15/8261* (2013.01); *C12Q 1/6895* (2013.01); *C12N 2310/14* (2013.01); *C12N 2310/531* (2013.01); *C12N 2320/12* (2013.01); *C12Q 2600/13* (2013.01); *C12Q 2600/156* (2013.01); *C12Q 2600/158* (2013.01); *Y02A 40/162* (2018.01); *Y02A 50/324* (2018.01)

(58) Field of Classification Search
CPC .................................................. C12N 15/8286
USPC ......................................................... 800/279
See application file for complete search history.

(56) References Cited

U.S. PATENT DOCUMENTS

| | | | |
|---|---|---|---|
| 5,107,065 A | 4/1992 | Shewmaker et al. | |
| 5,759,829 A | 6/1998 | Shewmaker et al. | |
| 7,612,194 B2 | 11/2009 | Andersen et al. | |
| 7,943,819 B2 | 5/2011 | Baum et al. | |
| 8,088,903 B2 | 1/2012 | Brandt et al. | |
| 9,238,822 B2 | 1/2016 | Baum et al. | |
| 2002/0048814 A1 | 4/2002 | Oeller | |
| 2003/0018993 A1 | 1/2003 | Gutterson et al. | |
| 2004/0067516 A1 | 4/2004 | Brandt et al. | |
| 2007/0050860 A1 | 3/2007 | Anderson et al. | |
| 2007/0124836 A1 | 5/2007 | Baum et al. | |
| 2007/0270576 A1 | 11/2007 | Brandt et al. | |
| 2009/0300796 A1 | 3/2009 | Raemaekers et al. | |
| 2009/0306189 A1 | 12/2009 | Raemaekers et al. | |
| 2010/0192265 A1 | 7/2010 | Anderson et al. | |
| 2011/0154545 A1 | 6/2011 | Anderson et al. | |
| 2011/0301223 A1 | 12/2011 | Broglie et al. | |
| 2012/0151631 A1 | 6/2012 | Niimi et al. | |
| 2012/0174258 A1 | 7/2012 | Narva et al. | |
| 2012/0216318 A1 | 8/2012 | La Rosa et al. | |
| 2013/0058890 A1 | 3/2013 | Raemaekers et al. | |
| 2013/0097730 A1 | 4/2013 | Narva et al. | |
| 2013/0185831 A1 | 7/2013 | Kovalic et al. | |
| 2013/0291188 A1* | 10/2013 | Bogaert | C12N 15/113 800/265 |
| 2014/0057251 A1 | 2/2014 | McKernan | |
| 2014/0194351 A1 | 7/2014 | Baum et al. | |
| 2015/0322455 A1 | 11/2015 | Narva et al. | |

FOREIGN PATENT DOCUMENTS

| | | | |
|---|---|---|---|
| JP | 2005512520 | | 2/2005 |
| KR | 20130077079 | | 7/2013 |
| WO | 9401550 | | 1/1994 |
| WO | 9805770 | A3 | 3/1998 |
| WO | 2005084312 | | 9/2005 |
| WO | 2007035650 | A2 | 3/2007 |
| WO | 2011025860 | A1 | 8/2009 |
| WO | 2011068062 | | 12/2011 |
| WO | 2011068144 | | 12/2011 |
| WO | 2011068162 | | 12/2011 |
| WO | 2011068188 | | 12/2011 |
| WO | 2012085862 | | 6/2012 |
| WO | 2012055982 | | 8/2012 |
| WO | 2014159829 | | 10/2014 |
| WO | WO2016018887 | * | 2/2016 |

OTHER PUBLICATIONS

Thomas et al. 2001, The Plant Journal 25(4):417-425.*

(Continued)

Primary Examiner — Li Zheng

(57) ABSTRACT

This disclosure concerns nucleic acid molecules and methods of use thereof for control of coleopteran and/or hemipteran pests through RNA interference-mediated inhibition of target coding and transcribed non-coding sequences in coleopteran and/or hemipteran pests. The disclosure also concerns methods for making transgenic plants that express nucleic acid molecules useful for the control of coleopteran and/or hemipteran pests, and the plant cells and plants obtained thereby.

35 Claims, 1 Drawing Sheet

Specification includes a Sequence Listing.

(56) References Cited

OTHER PUBLICATIONS

Yibrah et al. 1993, Hereditas 118:273-2890.*
Fourgoux-Nicol et al 1999, Plant Molecular Biology 40 :857-872.*
Price, et al., "RNAi-mediated crop protection against insects" Trends in Biotechnology, May 22, 2008, pp. 393-400, vol. 26, No. 7.
Baum, J.A. et al., "Control of coleopteran insect pests through RNA interference", Nature Biotechnology. vol. 25(11), pp. 1322-1326 (Nov. 4, 2007). See the abstract.
Sparks, Michael E., et al., Transcriptome of the Invasive Brown Marmorated Stink Bug, Halyomorpha halys (Stal) (Heteroptera: Pentatomidae), Plos One, Nov. 11, 2014, vol. 9, Issue, 11, pp. 1-13.
Palli, Subba Reddy, "RNAi methods for management of insects and their pathogens," CAB Reviews, Mar. 28, 2012, pp. 1-10, No. 4.
Cabrera, H.L., et al., (1992). Structure and expression of the *Drosophila* ubiquitin-52-amino-acid fusion-protein gene. The Biochemical Journal 283 (Pt 1_, 281-288.
Cook, R.K., et al., (2012). The generation of chromosomal deletions to provide extensive coverage and subdivision of the *Drosophila melanogaster* genome. Genome biology 13, R21.
Dietzl, G., et al., (2007). A genome-wide transgenic RNAi library for conditional gene inactivation in *Drosophila*. Nature 448, 151-156.
Mosesson, Y., et al., (2006). Monoubiquitylation: a recurrent theme in membrane protein transport. The Israel Medical Association journal : IMAJ 8, 233-237.
Ramanathan, H.N., et al., (2012). Cellular strategies for making monoubiquitin signals. Critical reviews in biochemistry and molecular biology 47, 17-28.
Baum et al., "Progress towards RNAi-mediated insect pest management." Advances in insect physiology, vol. 47. Academic Press, 2014. 249-295.
Bolognesi et al. "Characterizing the mechanism of action of double-stranded RNA activity against western corn rootworm (Diabrotica virgifera virgifera LeConte)." PloS one 7.10 (2012): e47534.
Fishilevich et al. "RNAi as a management tool for the western corn rootworm, Diabrotica virgifera virgifera." Pest management science 72.9 (2016): 1652-1663.
Velez et al. "Parameters for successful parental rnai as an insect pest management tool in western corn rootworm, Diabrotica virgifera virgifera," Genes 8,1 (2016): 7.

* cited by examiner

Generation of dsRNA from a single transcription template with a single pair of primers Generation of dsRNA from two transcription templates

SEQUENCE LISTING

```
<160> NUMBER OF SEQ ID NOS: 112

<210> SEQ ID NO 1
<211> LENGTH: 574
<212> TYPE: DNA
<213> ORGANISM: Diabrotica virgifera

<400> SEQUENCE: 1
aagttgggta taaccacgt ttcaagagag gcaaaaaacc aacggaaaat gcagatattc      60
gttaaaactt taaccggtaa gaccatcaca cttgaggtcg agccaagcga cacaatcgaa     120
aatgtcaagg cgaaaatcca agacaaagag ggtattccac cagatcagca acgtctaatt    180
tttgctggca aacaattgga agatggacgt acattgtccg attacaacat ccaaaaggaa    240
tcgacactcc atttggtgtt acgtctacgt ggtggtatca tcgaaccatc attgcgtatt    300
ttggcacaaa agtacaattg cgacaaaatg atttgccgta agtgctatgc tcgtttgcat    360
ccaagagcaa ccaattgccg taagaagaag tgtggccaca ccaacaattt gcgcccaaag    420
aagaagttga agtagacgat cgtatttttg tgctgtatgt ctggaggaaa acaatgttcg    480
gattcgtcca cagttgttat cattttgaat aatcgaaatt atgtgaatca ttcattgggt    540
acagcctgaa taaacttcgt tttctgaaac cggc                                574

<210> SEQ ID NO 2
<211> LENGTH: 128
<212> TYPE: PRT
<213> ORGANISM: Diabrotica virgifera

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Ile Glu Pro
65                  70                  75                  80

Ser Leu Arg Ile Leu Ala Gln Lys Tyr Asn Cys Asp Lys Met Ile Cys
                85                  90                  95

Arg Lys Cys Tyr Ala Arg Leu His Pro Arg Ala Thr Asn Cys Arg Lys
            100                 105                 110

Lys Lys Cys Gly His Thr Asn Asn Leu Arg Pro Lys Lys Lys Leu Lys
        115                 120                 125

<210> SEQ ID NO 3
<211> LENGTH: 652
<212> TYPE: DNA
<213> ORGANISM: Diabrotica virgifera
```

<400> SEQUENCE: 3

```
attaaatatc tgtactttta aatttaccac gcttttttgta acggaaacgt gttcatcaac    60
tgtcacttat caaataaact agacttcatt tttcacttgt cttttttcatt cggaagttag   120
cacgttgtgg aataaacact tccacaatgc aaattttcgt gaaaactctc actggtaaaa   180
ccatcaccct cgaggttgag ccatccgata caatcgaaaa tgttaaagct aagatccaag   240
acaaagaagg tatcccccca gaccagcaac gtttgatctt cgctggaaaa caactcgaag   300
atggacgtac cttgtcagac tacaacatcc agaaggaatc cacccttcac ttggtgctcc   360
gattgagagg aggtctcatc gagccttccc ttcgtatttt agccatgaag tacaactgcg   420
agaagatgat ctgccgtaaa tgttacgcca ggttacaccc aagggccacc aactgcagaa   480
agaagaagtg tggacacacc aacaacttgc gccccaagaa gaagctaaag tagactatta   540
cgaggttatt ttttacaatg ttaatatctt acaattccag atgttacttg aacatttatt   600
taactaatta taggaaatga catcaatcct aaaaaaaaaa aaaaaaaaaa aa           652
```

<210> SEQ ID NO 4
<211> LENGTH: 128
<212> TYPE: PRT
<213> ORGANISM: Diabrotica virgifera

<400> SEQUENCE: 4

```
Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly Leu Ile Glu Pro
 65                  70                  75                  80

Ser Leu Arg Ile Leu Ala Met Lys Tyr Asn Cys Glu Lys Met Ile Cys
                 85                  90                  95

Arg Lys Cys Tyr Ala Arg Leu His Pro Arg Ala Thr Asn Cys Arg Lys
            100                 105                 110

Lys Lys Cys Gly His Thr Asn Asn Leu Arg Pro Lys Lys Leu Lys
            115                 120                 125
```

<210> SEQ ID NO 5
<211> LENGTH: 4065
<212> TYPE: DNA
<213> ORGANISM: Diabrotica virgifera

<400> SEQUENCE: 5

```
cagattttcg tcaagacatt gacggggaag accattaccc tggaggtcga gcccagtgat    60
tccatcgaga ccgtcaaatc caagattcag gataaggaag ggattcctcc tgaccaacag   120
cgcttgattt tgctggcaa gcaactcgag gaaggccgat cttttgtcaga ctataacatc   180
caaaaagaga gtaccatcca tctcgtgctt cgactgagag gaggtggtat cgagatcgag   240
ccaacgttgg cgcaattggc tcgcaagcac aatattgaga gactcatttg tcgaaaatgt   300
tacgccagac tacacatcaa agctactaat tgccggaaaa aggcctgcgg ccactcatct   360
cagctcagac ccaagaagaa gcctaagagt taataatttt tgaactttct tttttccacg   420
```

```
aactagctta tgtgtactcg ctcagttgtt tcttctcagc cgccgattct tctgcccga    480
aacccaagtc gtcctctttg tacagaaatg tgtctcgccg cactatgtcg ctaactaagc    540
atgactcgat cgtcgaccac tccagtgggc gctcacgtgc ttgctgttcg gcgaggtaca    600
gcacgcggtt gacgcgattt ttgaatactg cattgagcat cgacaccacc tcgctcgcct    660
cctcccggag tccgagtttc ctgacggact tgatgccgag cggaccaccg tattcatttg    720
acgctcggtc cagtaggcgt tgggtgaacg cccaaccgtc ttctctttga ggctcttgtg    780
ggtggtgcat cccactaccg tagtggtgat tgttagatgc ggccgttggc ggtgtgtcgt    840
cctcagcttc aaagagcatc ctcagactac cctcagtcga cacaggctgg ttgggtgaga    900
gcccccaaaa tgcgctctca gagaatggcc caagcgtgaa gaacgcccaa tcctccgcgc    960
aactggacac aactgcggc cctgccgaat ttacagtttg ctgagccggc attctccgaa   1020
aagctggttc ctgatcaatc aaaccatgat cctctgaatt gtgttccaaa tgatcagcca   1080
acctttcata catacgccga ccgtatctc gtattgctga atgcgacaaa gcgtccgcgg   1140
gtttatagcc ggcacgtgcc tgccgtagca acgtatgac gaacctcgcc atcgccgtct    1200
tcggcactat gatgttcttg tcgtttagcc aagcgatctg ccgacatgaa tcagaccgcc   1260
ccttcatgaa cgaataatca ggtaccacag ccttcaccgg agcgcgcagg ttattgttca   1320
tcatttgtag ctcctgtaga gtcccaggcc gtccaacgag caggggccga gcggcggagt   1380
tcatcaagcc gcgataggg accagtcggg ggaggccgcg gagcagttcc ggctgcatat   1440
taggtggaga tgagccaacg ccatcgagac tctgcgggcc gccgaatccc ggcatgtcca   1500
tcattccttg ggcactgaga cttggcgagt tcatcgaatt cggcgtctgg ccttccatca   1560
tgctgttcag agatcccgga ggcgccggct gactggtgaa ggtcggactc tgcccgccag   1620
agcccatgtt ttggccaggc ggctgcggca tagcgcctcc agcgtgcatc atcatttgct   1680
gttgctgcat catttgttgc tggagcatgt acggcggctg ttgtggaggt ggcatcatgc   1740
gttgaggcgc cggctggata ttgccagcgt gcataatcgg cgtcatcgag ttcatacccca  1800
tcatcgtact ctgcatcata gggtgatgca ttggcgctga agccatgact tgagggttcg   1860
gcgcgccgta catttgaccc tggggcggcg gctgggctcc gggaggtggc tgccagcgct   1920
gttgctgttg ctgagcttgt tgctgtggtg tcggtacata tctattagtt ggggccctcc    1980
atgtattatg catcgtcaga gtggccgtgc gattgagttt tcgagcataa aaagtgcggc   2040
ctcagtgatt gggaatgatc atttcggcag tcggagtctt gtatggcctg agtatcagag   2100
acgtagtcca agagatcttg ctcgtgctgc gaggcagcaa gggaccgtta atcgtaatga   2160
agggctgatg tttgccattg tccgtgcgtg aagtcaagtc taggactgtg ccgtgacaag   2220
ctatggccgt aaactcaatt tccagttcgt agctaactcc aactcgttca tgtcggaagg   2280
tagcctctag actggcaggg atgtagagcg gaactatcgc aaccagggtc tgcgtaacag   2340
tcgtggaggc ttcacacaca gccacggtgt ccgtcgttat aacaatcagc gttgaatcta   2400
cattcgtcaa cgcgtggtag cttctgaaat ccagccaact caaaccggtc gtggcgttgg   2460
gccggtaccc gaaattttgt ctatgcttgt tccactgaag cgcctcgagc ggagacagtg   2520
gcggctgata agacctcgta gtttgtttca atctaacaca cacttccacc acggccaaag   2580
acgaattagt gaattcggtc ttgacataaa ttgtactacc taggtgcccc tcaagagtgt   2640
atgactcatc aacagtggtt ggtggcgatt tattgccctc gtacactttg gattgcggcg   2700
tcgccaaaca aacgtctgct ggccatatat tgacgacttg gatatcggac agatgggaac   2760
cattgatcga aactctgtag acgggggtag tttgggggcg cacctgtgca tccgcttcaa   2820
```

-continued

```
aagatgagac aaaattgcct gcagttcctt tttgactctt agagctgctc atgcacctga   2880
tcgagccgac aatcttatca atctcaaatc catttccgag tctttcgatg agattcacct   2940
catggacagc gcgctgctga attttctgcc tcaataactt caagcattct ccaggctctt   3000
ctaagaattc gttcaaagct gcagcagata ctcctgttgc cgtcatatgc ttcgctggcc   3060
gagtttcgct caaagtgcta tgcatatcag cacaggtgta actgagccat ctgagatata   3120
agagtccggc atcaaccttt tctttggcga cgagaaaatc attttgtgat tcttgttcat   3180
tgtgtgacca gccagctatc gggagcggaa tgggcagaga gccagaagtg aaagcggctc   3240
cgaaatccca atttaaggcg aggtaggtgg gggtgaaggg ccgagctggt agcggtggat   3300
atataggcgg aggttgtaga atgatagaag cgagctgcgt gaacttcata agatgggga   3360
tccattcact taagggggttg atcagaatag gacacgggct aatggttatt gccaagctta   3420
tttgcggcgg gattggcggc cctggagcgc cgtttgttgg agtagatatt tcggactcga   3480
tactgtcgag ggtgctggcg cgagctggag ggaggtgcct cacggatgag ccgccgctcg   3540
cgctacgatc attcaaacct accgacccac tattgttgtg tgaaagtaga gttgctccgc   3600
ccgttggccc aatagtcaca ggcgcgtcat ttctgatagc tagaacgtag tcatagctga   3660
atcgtcctcc tcgtcggatg acggtggca agctaactgg gatgtagagc tggcatttgt   3720
acctgtccac gtcgcctgtg acctcgagag tattgcttag cgcgaacact cgccctgatt   3780
tcttattggt ggtggcggag gtggcttgtt gttgatgtcc gggggatggg agcgtagtag   3840
tggaaacgga ttttccaaac tctctgaggg ctctagtgac tacctcgtaa ccatttgaa   3900
ctttgtcagt agagaataac gggggggctg atggacagcg atcggtgtcc aatccgttga   3960
ccagaccata cacgtatatt cgatcaccgg cggtgaagtg ggtgtgacaa aaactgatgg   4020
actggccacc tctaggcatt catttaatct ggcaagtgtt ccgct              4065
```

<210> SEQ ID NO 6
<211> LENGTH: 130
<212> TYPE: PRT
<213> ORGANISM: Diabrotica virgifera

<400> SEQUENCE: 6

```
Gln Ile Phe Val Lys Thr Leu Thr Gly Lys Thr Ile Thr Leu Glu Val
1               5                   10                  15

Glu Pro Ser Asp Ser Ile Glu Thr Val Lys Ser Lys Ile Gln Asp Lys
            20                  25                  30

Glu Gly Ile Pro Pro Asp Gln Gln Arg Leu Ile Phe Ala Gly Lys Gln
        35                  40                  45

Leu Glu Glu Gly Arg Ser Leu Ser Asp Tyr Asn Ile Gln Lys Glu Ser
    50                  55                  60

Thr Ile His Leu Val Leu Arg Leu Arg Gly Gly Ile Glu Ile Glu
65                  70                  75                  80

Pro Thr Leu Ala Gln Leu Ala Arg Lys His Asn Ile Glu Arg Leu Ile
                85                  90                  95

Cys Arg Lys Cys Tyr Ala Arg Leu His Ile Lys Ala Thr Asn Cys Arg
            100                 105                 110

Lys Lys Ala Cys Gly His Ser Ser Gln Leu Arg Pro Lys Lys Pro
        115                 120                 125

Lys Ser
    130
```

<210> SEQ ID NO 7
<211> LENGTH: 665
<212> TYPE: PRT
<213> ORGANISM: Diabrotica virgifera

<400> SEQUENCE: 7

Met Pro Arg Gly Gly Gln Ser Ile Ser Phe Cys His Thr His Phe Thr
1               5                   10                  15

Ala Gly Asp Arg Ile Tyr Val Tyr Gly Leu Val Asn Gly Leu Asp Thr
            20                  25                  30

Asp Arg Cys Pro Ser Ala Pro Pro Leu Phe Ser Thr Asp Lys Val Gln
        35                  40                  45

Asn Gly Tyr Glu Val Val Thr Arg Ala Leu Arg Glu Phe Gly Lys Ser
    50                  55                  60

Val Ser Thr Thr Thr Leu Pro Ser Pro Gly His Gln Gln Gln Ala Thr
65                  70                  75                  80

Ser Ala Thr Thr Asn Lys Lys Ser Gly Arg Val Phe Ala Leu Ser Asn
                85                  90                  95

Thr Leu Glu Val Thr Gly Asp Val Asp Arg Tyr Lys Cys Gln Leu Tyr
            100                 105                 110

Ile Pro Val Ser Leu Pro Pro Ser Ile Arg Arg Gly Gly Arg Phe Ser
        115                 120                 125

Tyr Asp Tyr Val Leu Ala Ile Arg Asn Asp Ala Pro Val Thr Ile Gly
    130                 135                 140

Pro Thr Gly Gly Ala Thr Leu Leu Ser His Asn Asn Ser Gly Ser Val
145                 150                 155                 160

Gly Leu Asn Asp Arg Ser Ala Ser Gly Gly Ser Ser Val Arg His Leu
                165                 170                 175

Pro Pro Ala Arg Ala Ser Thr Leu Asp Ser Ile Glu Ser Glu Ile Ser
            180                 185                 190

Thr Pro Thr Asn Gly Ala Pro Gly Pro Pro Ile Pro Pro Gln Ile Ser
        195                 200                 205

Leu Ala Ile Thr Ile Ser Pro Cys Pro Ile Leu Ile Asn Pro Leu Ser
    210                 215                 220

Glu Trp Ile Pro Ile Phe Met Lys Phe Thr Gln Leu Ala Ser Ile Ile
225                 230                 235                 240

Leu Gln Pro Pro Ile Tyr Pro Pro Leu Pro Ala Arg Pro Phe Thr
                245                 250                 255

Pro Thr Tyr Leu Ala Leu Asn Trp Asp Phe Gly Ala Ala Phe Thr Ser
            260                 265                 270

Gly Ser Leu Pro Ile Pro Leu Pro Ile Ala Gly Trp Ser His Asn Glu
        275                 280                 285

Gln Glu Ser Gln Asn Asp Phe Leu Val Ala Lys Glu Lys Val Asp Ala
    290                 295                 300

Gly Leu Leu Tyr Leu Arg Trp Leu Ser Tyr Thr Cys Ala Asp Met His
305                 310                 315                 320

Ser Thr Leu Ser Glu Thr Arg Pro Ala Lys His Met Thr Ala Thr Gly
                325                 330                 335

Val Ser Ala Ala Ala Leu Asn Glu Phe Leu Glu Glu Pro Gly Glu Cys
            340                 345                 350

Leu Lys Leu Leu Arg Gln Lys Ile Gln Gln Arg Ala Val His Glu Val
        355                 360                 365

Asn Leu Ile Glu Arg Leu Gly Asn Gly Phe Glu Ile Asp Lys Ile Val
    370                 375                 380

Gly Ser Ile Arg Cys Met Ser Ser Lys Ser Gln Lys Gly Thr Ala
385                 390                 395                 400

Gly Asn Phe Val Ser Ser Phe Glu Ala Asp Ala Gln Val Arg Pro Gln
                405                 410                 415

Thr Thr Pro Val Tyr Arg Val Ser Ile Asn Gly Ser His Leu Ser Asp
            420                 425                 430

Ile Gln Val Val Asn Ile Trp Pro Ala Asp Val Cys Leu Ala Thr Pro
        435                 440                 445

Gln Ser Lys Val Tyr Glu Gly Asn Lys Ser Pro Pro Thr Thr Val Asp
    450                 455                 460

Glu Ser Tyr Thr Leu Glu Gly His Leu Gly Ser Thr Ile Tyr Val Lys
465                 470                 475                 480

Thr Glu Phe Thr Asn Ser Ser Leu Ala Val Val Glu Val Cys Val Arg
                485                 490                 495

Leu Lys Gln Thr Thr Arg Ser Tyr Gln Pro Pro Leu Ser Pro Leu Glu
            500                 505                 510

Ala Leu Gln Trp Asn Lys His Arg Gln Asn Phe Gly Tyr Arg Pro Asn
        515                 520                 525

Ala Thr Thr Gly Leu Ser Trp Leu Asp Phe Arg Ser Tyr His Ala Leu
    530                 535                 540

Thr Asn Val Asp Ser Thr Leu Ile Val Ile Thr Thr Asp Thr Val Ala
545                 550                 555                 560

Val Cys Glu Ala Ser Thr Thr Val Thr Gln Thr Leu Val Ala Ile Val
                565                 570                 575

Pro Leu Tyr Ile Pro Ala Ser Leu Glu Ala Thr Phe Arg His Glu Arg
            580                 585                 590

Val Gly Val Ser Tyr Glu Leu Glu Ile Glu Phe Thr Ala Ile Ala Cys
        595                 600                 605

His Gly Thr Val Leu Asp Leu Thr Ser Arg Thr Asp Asn Gly Lys His
    610                 615                 620

Gln Pro Phe Ile Thr Ile Asn Gly Pro Leu Leu Pro Arg Ser Thr Ser
625                 630                 635                 640

Lys Ile Ser Trp Thr Thr Ser Leu Ile Leu Arg Pro Tyr Lys Thr Pro
                645                 650                 655

Thr Ala Glu Met Ile Ile Pro Asn His
            660                 665

<210> SEQ ID NO 8
<211> LENGTH: 537
<212> TYPE: PRT
<213> ORGANISM: Diabrotica virgifera

<400> SEQUENCE: 8

Gly Arg Thr Phe Tyr Ala Arg Lys Leu Asn Arg Thr Ala Thr Leu Thr
1               5                   10                  15

Met His Asn Thr Trp Arg Pro Pro Thr Asn Arg Tyr Val Pro Thr Pro
                20                  25                  30

Gln Gln Gln Ala Gln Gln Gln Gln Arg Trp Gln Pro Pro Gly
            35                  40                  45

Ala Gln Pro Pro Gln Gly Gln Met Tyr Gly Ala Pro Asn Pro Gln
        50                  55                  60

Val Met Ala Ser Ala Pro Met His Pro Met Met Gln Ser Thr Met
65                  70                  75                  80

Met Gly Met Asn Ser Met Thr Pro Ile Met His Ala Gly Asn Ile Gln
                85                  90                  95

```
Pro Ala Pro Gln Arg Met Met Pro Pro Gln Gln Pro Pro Tyr Met
            100                 105                 110

Leu Gln Gln Met Met Gln Gln Gln Met Met Met His Ala Gly
            115                 120                 125

Gly Ala Met Pro Gln Pro Pro Gly Gln Asn Met Gly Ser Gly Gly Gln
130                 135                 140

Ser Pro Thr Phe Thr Ser Gln Pro Ala Pro Pro Gly Ser Leu Asn Ser
145                 150                 155                 160

Met Met Glu Gly Gln Thr Pro Asn Ser Met Asn Ser Pro Ser Leu Ser
                165                 170                 175

Ala Gln Gly Met Met Asp Met Pro Gly Phe Gly Gly Pro Gln Ser Leu
            180                 185                 190

Asp Gly Val Gly Ser Ser Pro Pro Asn Met Gln Pro Glu Leu Leu Arg
            195                 200                 205

Gly Leu Pro Arg Leu Val Pro Tyr Arg Gly Leu Met Asn Ser Ala Ala
            210                 215                 220

Arg Pro Leu Leu Val Gly Arg Pro Gly Thr Leu Gln Glu Leu Gln Met
225                 230                 235                 240

Met Asn Asn Asn Leu Arg Ala Pro Val Lys Ala Val Pro Asp Tyr
                245                 250                 255

Ser Phe Met Lys Gly Arg Ser Asp Ser Cys Arg Gln Ile Ala Trp Leu
                260                 265                 270

Asn Asp Lys Asn Ile Ile Val Pro Lys Thr Ala Met Ala Arg Phe Val
            275                 280                 285

Ile Ala Leu Leu Arg Gln Ala Arg Ala Gly Tyr Lys Pro Ala Asp Ala
            290                 295                 300

Leu Ser His Ser Ala Ile Arg Asp Thr Ala Arg Arg Met Tyr Glu Arg
305                 310                 315                 320

Leu Ala Asp His Leu Glu His Asn Ser Glu Asp His Gly Leu Ile Asp
                325                 330                 335

Gln Glu Pro Ala Phe Arg Arg Met Pro Ala Gln Gln Thr Val Asn Ser
            340                 345                 350

Ala Gly Pro Pro Val Val Ser Ser Cys Ala Glu Asp Trp Ala Phe Phe
            355                 360                 365

Thr Leu Gly Pro Phe Ser Glu Ser Ala Phe Trp Gly Leu Ser Pro Asn
            370                 375                 380

Gln Pro Val Ser Thr Glu Gly Ser Leu Arg Met Leu Phe Glu Ala Glu
385                 390                 395                 400

Asp Asp Thr Pro Pro Thr Ala Ala Ser Asn Asn His His Tyr Gly Ser
            405                 410                 415

Gly Met His His Pro Gln Glu Pro Gln Arg Glu Asp Gly Trp Ala Phe
            420                 425                 430

Thr Gln Arg Leu Leu Asp Arg Ala Ser Asn Glu Tyr Gly Gly Pro Leu
            435                 440                 445

Gly Ile Lys Ser Val Arg Lys Leu Gly Leu Arg Glu Glu Ala Ser Glu
            450                 455                 460

Val Val Ser Met Leu Asn Ala Val Phe Lys Asn Arg Val Asn Arg Val
465                 470                 475                 480

Leu Tyr Leu Ala Glu Gln Ala Arg Glu Arg Pro Leu Glu Trp Ser
                485                 490                 495

Thr Ile Glu Ser Cys Leu Val Ser Asp Ile Val Arg Arg Asp Thr Phe
            500                 505                 510
```

Leu Tyr Lys Glu Asp Asp Leu Gly Phe Gly Pro Glu Glu Ser Ala Ala
    515                 520                 525

Glu Lys Lys Gln Leu Ser Glu Tyr Thr
    530                 535

<210> SEQ ID NO 9
<211> LENGTH: 306
<212> TYPE: DNA
<213> ORGANISM: Diabrotica virgifera

<400> SEQUENCE: 9

```
gaaaatgtca aggcgaaaat ccaagacaaa gagggtattc caccagatca gcaacgtcta    60
atttttgctg gcaaacaatt ggaagatgga cgtacattgt ccgattacaa catccaaaag   120
gaatcgacac tccatttggt gttacgtcta cgtggtggta tcatcgaacc atcattgcgt   180
attttggcac aaaagtacaa ttgcgacaaa atgatttgcc gtaagtgcta tgctcgtttg   240
catccaagag caaccaattg ccgtaagaag aagtgtggcc acaccaacaa tttgcgccca   300
aagaag                                                              306
```

<210> SEQ ID NO 10
<211> LENGTH: 361
<212> TYPE: DNA
<213> ORGANISM: Diabrotica virgifera

<400> SEQUENCE: 10

```
cagattttcg tcaagacatt gacggggaag accattaccc tggaggtcga gcccagtgat    60
tccatcgaga ccgtcaaatc caagattcag gataaggaag ggattcctcc tgaccaacag   120
cgcttgattt ttgctggcaa gcaactcgag gaaggccgat ctttgtcaga ctataacatc   180
caaaaagaga gtaccatcca tctcgtgctt cgactgagag gaggtggtat cgagatcgag   240
ccaacgttgg cgcaattggc tcgcaagcac aatattgaga gactcatttg tcgaaaatgt   300
tacgccagac tacacatcaa agctactaat tgccggaaaa aggcctgcgg ccactcatct   360
c                                                                   361
```

<210> SEQ ID NO 11
<211> LENGTH: 117
<212> TYPE: DNA
<213> ORGANISM: Diabrotica virgifera

<400> SEQUENCE: 11

```
ccaccagatc agcaacgtct aattttgct ggcaaacaat tggaagatgg acgtacattg    60
tccgattaca acatccaaaa ggaatcgaca ctccatttgg tgttacgtct acgtggt     117
```

<210> SEQ ID NO 12
<211> LENGTH: 143
<212> TYPE: DNA
<213> ORGANISM: Diabrotica virgifera

<400> SEQUENCE: 12

```
tcgaaccatc attgcgtatt ttggcacaaa agtacaattg cgacaaaatg atttgccgta    60
agtgctatgc tcgtttgcat ccaagagcaa ccaattgccg taagaagaag tgtggccaca   120
ccaacaattt gcgcccaaag aag                                           143
```

<210> SEQ ID NO 13
<211> LENGTH: 141
<212> TYPE: DNA
<213> ORGANISM: Diabrotica virgifera

<400> SEQUENCE: 13

```
caagagaggc aaaaaaccaa cggaaaatgc agatattcgt taaaacttta accggtaaga    60
ccatcacact tgaggtcgag ccaagcgaca caatcgaaaa tgtcaaggcg aaaatccaag   120
acaaagaggg tattccacca g                                             141
```

<210> SEQ ID NO 14
<211> LENGTH: 130
<212> TYPE: DNA
<213> ORGANISM: Diabrotica virgifera

<400> SEQUENCE: 14

```
gccgtaagtg ctatgctcgt ttgcatccaa gagcaaccaa ttgccgtaag aagaagtgtg    60
gccacaccaa caatttgcgc ccaaagaaga agttgaagta gacgatcgta tttttgtgct   120
gtatgtctgg                                                          130
```

<210> SEQ ID NO 15
<211> LENGTH: 165
<212> TYPE: DNA
<213> ORGANISM: Diabrotica virgifera

<400> SEQUENCE: 15

```
cagcaacgtc taattttgc tggcaaacaa ttggaagatg gacgtacatt gtccgattac    60
aacatccaaa aggaatcgac actccatttg gtgttacgtc tacgtggtgg tatcatcgaa   120
ccatcattgc gtattttggc acaaaagtac aattgcgaca aaatg                   165
```

<210> SEQ ID NO 16
<211> LENGTH: 24
<212> TYPE: DNA
<213> ORGANISM: Artificial Sequence
<220> FEATURE:
<223> OTHER INFORMATION: synthesized promotor oligonucleotide

<400> SEQUENCE: 16

```
ttaatacgac tcactatagg gaga                                           24
```

<210> SEQ ID NO 17
<211> LENGTH: 503
<212> TYPE: DNA
<213> ORGANISM: Artificial Sequence
<220> FEATURE:
<223> OTHER INFORMATION: synthesized partial coding region

<400> SEQUENCE: 17

```
caccatgggc tccagcggcg ccctgctgtt ccacggcaag atcccctacg tggtggagat    60
ggagggcaat gtggatggcc acaccttcag catccgcgc aagggctacg gcgatgccag   120
cgtgggcaag gtggatgccc agttcatctg caccaccggc gatgtgcccg tgccctggag   180
cacccctggtg accacctga cctacggcgc ccagtgcttc gccaagtacg gccccgagct   240
gaaggatttc tacaagagct gcatgcccga tggctacgtg caggagcgca ccatcaccttt   300
cgagggcgat ggcaatttca agacccgcgc cgaggtgacc ttcgagaatg gcagcgtgta   360
caatcgcgtg aagctgaatg ccagggctt caagaaggat ggccacgtgc tgggcaagaa   420
tctggagttc aatttcaccc ccactgcct gtacatctgg ggcgatcagg ccaatcacgg   480
cctgaagagc gccttcaaga tct                                           503
```

<210> SEQ ID NO 18

<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 18
ttaatacgac tcactatagg gagagaaaat gtcaaggcga aaatccaag    49

<210> SEQ ID NO 19
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 19
ttaatacgac tcactatagg gagacttctt tgggcgcaaa ttgttg    46

<210> SEQ ID NO 20
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 20
ttaatacgac tcactatagg gagacagatt ttcgtcaaga cattgacg    48

<210> SEQ ID NO 21
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 21
ttaatacgac tcactatagg gagagagatg agtggccgca ggccttttc    50

<210> SEQ ID NO 22
<211> LENGTH: 52
<212> TYPE: DNA
<213> ORGANISM: Artificial Sequence
<220> FEATURE:
<223> OTHER INFORMATION: synthesized primer oligonucleotide

<400> SEQUENCE: 22
ttaatacgac tcactatagg gagaccacca gatcagcaac gtctaatttt tg    52

<210> SEQ ID NO 23
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 23
ttaatacgac tcactatagg gagaaccacg tagacgtaac accaaatg    48

<210> SEQ ID NO 24
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 24

```
ttaatacgac tcactatagg gagatcgaac catcattgcg tattttgg          48

<210> SEQ ID NO 25
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 25
ttaatacgac tcactatagg gagacttctt tgggcgcaaa ttgttggtg         49

<210> SEQ ID NO 26
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 26
ttaatacgac tcactatagg gagacaagag aggcaaaaaa ccaacg            46

<210> SEQ ID NO 27
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 27
ttaatacgac tcactatagg gagactggtg gaatacectc tttgtc            46

<210> SEQ ID NO 28
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 28
ttaatacgac tcactatagg gagagccgta agtgctatgc tcgtttg           47

<210> SEQ ID NO 29
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 29
ttaatacgac tcactatagg gagaccagac atacagcaca aaaatac           47

<210> SEQ ID NO 30
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 30
ttaatacgac tcactatagg gagacagcaa cgtctaattt ttgctg            46

<210> SEQ ID NO 31
<211> LENGTH: 48
<212> TYPE: DNA
```

```
<213> ORGANISM: Artificial Sequence
<220> FEATURE:
<223> OTHER INFORMATION: synthesized primer oligonucleotide

<400> SEQUENCE: 31
ttaatacgac tcactatagg gagacattttt gtcgcaattg tacttttg                    48

<210> SEQ ID NO 32
<211> LENGTH: 705
<212> TYPE: DNA
<213> ORGANISM: Artificial Sequence
<220> FEATURE:
<223> OTHER INFORMATION: synthesized protein coding region

<400> SEQUENCE: 32
atgtcatctg gagcacttct ctttcatggg aagattcctt acgttgtgga gatggaaggg       60
aatgttgatg gccacacctt tagcatacgt gggaaaggct acggagatgc ctcagtggga      120
aaggttgatg cacagttcat ctgcacaact ggtgatgttc ctgtgccttg gagcacactt      180
gtcaccactc tcacctatgg agcacagtgc tttgccaagt atggtccaga gttgaaggac      240
ttctacaagt cctgtatgcc agatggctat gtgcaagagc gcacaatcac ctttgaagga      300
gatggcaact tcaagactag ggctgaagtc acctttgaga tgggtctgt ctacaatagg       360 gtcaaactca atggtcaagg cttcaagaaa gatggtcatg tgttgggaaa gaacttggag      420
ttcaacttca ctccccactg cctctacatc tggggtgacc aagccaacca cggtctcaag      480
tcagccttca agatctgtca tgagattact ggcagcaaag gcgacttcat agtggctgac      540
cacacccaga tgaacactcc cattggtgga ggtccagttc atgttccaga gtatcatcac      600
atgtcttacc atgtgaaact ttccaaagat gtgacagacc acagagacaa catgtccttg      660
aaagaaactg tcagagctgt tgactgtcgc aagacctacc tttga                      705

<210> SEQ ID NO 33
<211> LENGTH: 218
<212> TYPE: DNA
<213> ORGANISM: Diabrotica virgifera

<400> SEQUENCE: 33
tagctctgat gacagagccc atcgagtttc aagccaaaca gttgcataaa gctatcagcg       60
gattgggaac tgatgaaagt acaatmgtmg aaattttaag tgtmcacaac aacgatgaga      120
ttataagaat ttcccaggcc tatgaaggat tgtaccaacg mtcattggaa tctgatatca      180
aaggagatac ctcaggaaca ttaaaaaaga attattag                              218

<210> SEQ ID NO 34
<211> LENGTH: 424
<212> TYPE: DNA
<213> ORGANISM: Diabrotica virgifera
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t

<400> SEQUENCE: 34
ttgttacaag ctggagaact tctctttgct ggaaccgaag agtcagtatt taatgctgta       60
```

```
ttctgtcaaa gaaataaacc acaattgaat ttgatattcg acaaatatga agaaattgtt      120
gggcatccca ttgaaaaagc cattgaaaac gagttttcag gaaatgctaa acaagccatg      180
ttacacctta tccagagcgt aagagatcaa gttgcatatt tggtaaccag gctgcatgat      240
tcaatggcag gcgtcggtac tgacgataga actttaatca gaattgttgt ttcgagatct      300
gaaatcgatc tagaggaaat caaacaatgc tatgaagaaa tctacagtaa aaccttggct      360
gataggatag cggatgacac atctggcgac tannnaaaag ccttattagc cgttgttggt      420
taag                                                                   424

<210> SEQ ID NO 35
<211> LENGTH: 397
<212> TYPE: DNA
<213> ORGANISM: Diabrotica virgifera

<400> SEQUENCE: 35
agatgttggc tgcatctaga gaattacaca agttcttcca tgattgcaag gatgtactga       60
gcagaatagt ggaaaaacag gtatccatgt ctgatgaatt gggaagggac gcaggagctg      120
tcaatgccct tcaacgcaaa caccagaact tcctccaaga cctacaaaca ctccaatcga      180
acgtccaaca aatccaagaa gaatcagcta aacttcaagc tagctatgcc ggtgatagag      240
ctaaagaaat caccaacagg gagcaggaag tggtagcagc ctgggcagcc ttgcagatcg      300
cttgcgatca gagacacgga aaattgagcg atactggtga tctattcaaa ttctttaact      360
tggtacgaac gttgatgcag tggatggacg aatggac                               397

<210> SEQ ID NO 36
<211> LENGTH: 490
<212> TYPE: DNA
<213> ORGANISM: Diabrotica virgifera

<400> SEQUENCE: 36
gcagatgaac accagcgaga aaccaagaga tgttagtggt gttgaattgt tgatgaacaa       60
ccatcagaca ctcaaggctg agatcgaagc cagagaagac aactttacgg cttgtatttc      120
tttaggaaag gaattgttga gccgtaatca ctatgctagt gctgatatta aggataaatt      180
ggtcgcgttg acgaatcaaa ggaatgctgt actacagagg tgggaagaaa gatgggagaa      240
cttgcaactc atcctcgagg tataccaatt cgccagagat gcggccgtcg ccgaagcatg      300
gttgatcgca caagaacctt acttgatgag ccaagaacta ggacacacca ttgacgacgt      360
tgaaaacttg ataagaaac acgaagcgtt cgaaaaatcg gcagcggcgc aagaagagag      420
attcagtgct ttggagagac tgacgacgtt cgaattgaga gaaataaaga ggaaacaaga      480
agctgcccag                                                             490

<210> SEQ ID NO 37
<211> LENGTH: 330
<212> TYPE: DNA
<213> ORGANISM: Diabrotica virgifera

<400> SEQUENCE: 37
agtgaaatgt tagcaaatat aacatccaag tttcgtaatt gtacttgctc agttagaaaa       60
tattctgtag tttcactatc ttcaaccgaa aatagaataa atgtagaacc tcgcgaactt      120
gcctttcctc caaatatcta agaacctcga caagtttggt tggagagttt agatacgata      180
gacgacaaaa aattgggtat tcttgagctg catcctgatg ttttttgctac taatccaaga      240
```

```
atagatatta tacatcaaaa tgttagatgg caaagtttat atagatatgt aagctatgct    300
catacaaagt caagatttga agtgagaggt                                    330

<210> SEQ ID NO 38
<211> LENGTH: 320
<212> TYPE: DNA
<213> ORGANISM: Diabrotica virgifera

<400> SEQUENCE: 38
caaagtcaag atttgaagtg agaggtggag gtcgaaaacc gtggccgcaa aagggattgg    60
gacgtgctcg acatggttca attagaagtc cactttggag aggtggagga gttgttcatg   120
gaccaaaatc tccaacccct catttttaca tgattccatt ctacacccgt ttgctgggtt   180
tgactagcgc actttcagta aaatttgccc aagatgactt gcacgttgtg gatagtctag   240
atctgccaac tgacgaacaa agttatatag aagagctggt caaaagccgc ttttggggt    300 ccttcttgtt ttatttgtag                                               320

<210> SEQ ID NO 39
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 39
ttaatacgac tcactatagg gagacaccat gggctccagc ggcgccc                  47

<210> SEQ ID NO 40
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 40
agatcttgaa ggcgctcttc agg                                            23

<210> SEQ ID NO 41
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 41
caccatgggc tccagcggcg ccc                                            23

<210> SEQ ID NO 42
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 42
ttaatacgac tcactatagg gagaagatct tgaaggcgct cttcagg                  47

<210> SEQ ID NO 43
<211> LENGTH: 46
<212> TYPE: DNA
<213> ORGANISM: Artificial Sequence
<220> FEATURE:
<223> OTHER INFORMATION: synthesized primer oligonucleotide
```

<400> SEQUENCE: 43
ttaatacgac tcactatagg gagagctcca acagtggttc cttatc                    46

<210> SEQ ID NO 44
<211> LENGTH: 29
<212> TYPE: DNA
<213> ORGANISM: Artificial Sequence
<220> FEATURE:
<223> OTHER INFORMATION: synthesized primer oligonucleotide

<400> SEQUENCE: 44
ctaataattc tttttaatg ttcctgagg                                         29

<210> SEQ ID NO 45
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 45
gctccaacag tggttcctta tc                                               22

<210> SEQ ID NO 46
<211> LENGTH: 53
<212> TYPE: DNA
<213> ORGANISM: Artificial Sequence
<220> FEATURE:
<223> OTHER INFORMATION: synthesized primer oligonucleotide

<400> SEQUENCE: 46
ttaatacgac tcactatagg gagactaata attcttttt aatgttcctg agg              53

<210> SEQ ID NO 47
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 47
ttaatacgac tcactatagg gagattgtta caagctggag aacttctc                   48

<210> SEQ ID NO 48
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 48
cttaaccaac aacggctaat aagg                                             24

<210> SEQ ID NO 49
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 49
ttgttacaag ctggagaact tctc                                             24

<210> SEQ ID NO 50

<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 50
ttaatacgac tcactatagg gagacttaac caacaacggc taataagg    48

<210> SEQ ID NO 51
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 51
ttaatacgac tcactatagg gagaagatgt tggctgcatc tagagaa    47

<210> SEQ ID NO 52
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 52
gtccattcgt ccatccactg ca    22

<210> SEQ ID NO 53
<211> LENGTH: 23
<212> TYPE: DNA
<213> ORGANISM: Artificial Sequence
<220> FEATURE:
<223> OTHER INFORMATION: synthesized primer oligonucleotide

<400> SEQUENCE: 53
agatgttggc tgcatctaga gaa    23

<210> SEQ ID NO 54
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 54
ttaatacgac tcactatagg gagagtccat tcgtccatcc actgca    46

<210> SEQ ID NO 55
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 55
ttaatacgac tcactatagg gagagcagat gaacaccagc gagaaa    46

<210> SEQ ID NO 56
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 56
ctgggcagct tcttgtttcc tc                                            22

<210> SEQ ID NO 57
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 57
gcagatgaac accagcgaga aa                                            22

<210> SEQ ID NO 58
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 58
ttaatacgac tcactatagg gagactgggc agcttcttgt ttcctc                  46

<210> SEQ ID NO 59
<211> LENGTH: 51
<212> TYPE: DNA
<213> ORGANISM: Artificial Sequence
<220> FEATURE:
<223> OTHER INFORMATION: synthesized primer oligonucleotide

<400> SEQUENCE: 59
ttaatacgac tcactatagg gagaagtgaa atgttagcaa atataacatc c            51

<210> SEQ ID NO 60
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 60
acctctcact tcaaatcttg actttg                                        26

<210> SEQ ID NO 61
<211> LENGTH: 27
<212> TYPE: DNA
<213> ORGANISM: Artificial Sequence
<220> FEATURE:
<223> OTHER INFORMATION: synthesized primer oligonucleotide

<400> SEQUENCE: 61
agtgaaatgt tagcaaatat aacatcc                                       27

<210> SEQ ID NO 62
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 62
ttaatacgac tcactatagg gagaacctct cacttcaaat cttgactttg              50

<210> SEQ ID NO 63
<211> LENGTH: 50
<212> TYPE: DNA

```
<213> ORGANISM: Artificial Sequence
<220> FEATURE:
<223> OTHER INFORMATION: synthesized primer oligonucleotide

<400> SEQUENCE: 63
ttaatacgac tcactatagg gagacaaagt caagatttga agtgagaggt          50

<210> SEQ ID NO 64
<211> LENGTH: 25
<212> TYPE: DNA
<213> ORGANISM: Artificial Sequence
<220> FEATURE:
<223> OTHER INFORMATION: synthesized primer oligonucleotide

<400> SEQUENCE: 64
ctacaaataa aacaagaagg acccc                                     25

<210> SEQ ID NO 65
<211> LENGTH: 26
<212> TYPE: DNA
<213> ORGANISM: Artificial Sequence
<220> FEATURE:
<223> OTHER INFORMATION: synthesized primer oligonucleotide

<400> SEQUENCE: 65
caaagtcaag atttgaagtg agaggt                                    26

<210> SEQ ID NO 66
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 66
ttaatacgac tcactatagg gagactacaa ataaacaag aaggacccc             49

<210> SEQ ID NO 67
<211> LENGTH: 1150
<212> TYPE: DNA
<213> ORGANISM: Zea mays

<400> SEQUENCE: 67
caacggggca gcactgcact gcactgcaac tgcgaatttc cgtcagcttg gagcggtcca    60
agcgccctgc gaagcaaact acgccgatgg cttcggcggc ggcgtgggag ggtccgacgg   120
ccgcggagct gaagacagcg ggggcggagg tgattcccgg cggcgtgcga gtgaaggggt   180
gggtcatcca gtcccacaaa ggccctatcc tcaacgccgc ctctctgcaa cgctttgaag   240
atgaacttca acaacacat ttacctgaga tggttttttgg agagagtttc ttgtcacttc   300
aacatacaca aactggcatc aaatttcatt ttaatgcgct tgatgcactc aaggcatgga   360
agaaagaggc actgccacct gttgaggttc ctgctgcagc aaaatggaag ttcagaagta   420
agccttctga ccaggttata cttgactacg actatacatt tacgacacca tattgtggga   480
gtgatgctgt ggttgtgaac tctggcactc cacaaacaag tttagatgga tgcggcactt   540
tgtgttggga ggatactaat gatcggattg acattgttgc cctttcagca aaagaaccca   600 ttctttttcta cgacgaggtt atcttgtatg aagatgagtt agctgacaat ggtatctcat   660
ttcttactgt gcgagtgagg gtaatgccaa ctggttggtt tctgcttttg cgttttggc    720 ttagagttga tggtgtactg atgaggttga gagacactcg gttacattgc ctgtttggaa   780
acggcgacgg agccaagcca gtggtacttc gtgagtgctg ctggagggaa gcaacatttg   840
```

```
ctactttgtc tgcgaaagga tatccttcgg actctgcagc gtacgcggac ccgaacctta    900
ttgcccataa gcttcctatt gtgacgcaga agacccaaaa gctgaaaaat cctacctgac    960
tgacacaaag gcgccctacc gcgtgtacat catgactgtc ctgtcctatc gttgcctttt   1020
gtgtttgcca catgttgtgg atgtacgttt ctatgacgaa acaccatagt ccatttcgcc   1080
tgggccgaac agagatagct gattgtcatg tcacgtttga attagaccat tccttagccc   1140
tttttccccc                                                          1150
```

<210> SEQ ID NO 68
<211> LENGTH: 22
<212> TYPE: DNA
<213> ORGANISM: Artificial Sequence
<220> FEATURE:
<223> OTHER INFORMATION: synthesized primer oligonucleotide
<220> FEATURE:
<221> NAME/KEY: misc_feature
<222> LOCATION: (22)..(22)
<223> OTHER INFORMATION: n is a, c, g, or t

<400> SEQUENCE: 68

```
tttttttttt tttttttttt vn                                              22
```

<210> SEQ ID NO 69
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 69

```
ttgtgatgtt ggtggcgtat                                                 20
```

<210> SEQ ID NO 70
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 70

```
tgttaaataa aaccccaaag atcg                                            24
```

<210> SEQ ID NO 71
<211> LENGTH: 21
<212> TYPE: DNA
<213> ORGANISM: Artificial Sequence
<220> FEATURE:
<223> OTHER INFORMATION: synthesized primer oligonucleotide

<400> SEQUENCE: 71

```
tgagggtaat gccaactggt t                                               21
```

<210> SEQ ID NO 72
<211> LENGTH: 24
<212> TYPE: DNA
<213> ORGANISM: Artificial Sequence
<220> FEATURE:
<223> OTHER INFORMATION: synthesized primer oligonucleotide

<400> SEQUENCE: 72

```
gcaatgtaac cgagtgtctc tcaa                                            24
```

<210> SEQ ID NO 73

```
<211> LENGTH: 32
<212> TYPE: DNA
<213> ORGANISM: Artificial Sequence
<220> FEATURE:
<223> OTHER INFORMATION: synthesized probe oligonucleotide

<400> SEQUENCE: 73
tttttggctt agagttgatg gtgtactgat ga                                    32

<210> SEQ ID NO 74
<211> LENGTH: 151
<212> TYPE: DNA
<213> ORGANISM: Escherichia coli

<400> SEQUENCE: 74
gaccgtaagg cttgatgaaa caacgcggcg agctttgatc aacgaccttt tggaaacttc      60
ggcttcccct ggagagagcg agattctccg cgctgtagaa gtcaccattg ttgtgcacga     120
cgacatcatt ccgtggcgtt atccagctaa g                                   151

<210> SEQ ID NO 75
<211> LENGTH: 69
<212> TYPE: DNA
<213> ORGANISM: Artificial Sequence
<220> FEATURE:
<223> OTHER INFORMATION: synthesized partial coding region

<400> SEQUENCE: 75
tgttcggttc cctctaccaa gcacagaacc gtcgcttcag caacacctca gtcaaggtga      60
tggatgttg                                                              69

<210> SEQ ID NO 76
<211> LENGTH: 4233
<212> TYPE: DNA
<213> ORGANISM: Zea mays

<400> SEQUENCE: 76
agcctggtgt ttccggagga gacagacatg atccctgccg ttgctgatcc gacgacgctg      60
gacggcgggg gcgcgcgcag gccgttgctc ccggagacgg accctcgggg gcgtgctgcc     120
gccggcgccg agcagaagcg gccgccggct acgccgaccg ttctcaccgc cgtcgtctcc     180
gccgtgctcc tgctcgtcct cgtggcggtc acagtcctcg cgtcgcagca cgtcgacggg     240
caggctgggg gcgttcccgc gggcgaagat gccgtcgtcg tcgaggtggc cgcctcccgt     300
ggcgtggctg agggcgtgtc ggagaagtcc acggccccgc tcctcggctc cggcgcgctc     360
caggacttct cctggaccaa cgcgatgctg gcgtggcagc gcacggcgtt ccacttccag     420 cccccccaaga actggatgaa cggttagttg gacccgtcgc catcggtgac gacgcgcgga     480 tcgtttttt cttttttcct ctcgttctgg ctctaacttg gttccgcgtt tctgtcacgg     540
acgcctcgtg cacatggcga tacccgatcc gccggccgcg tatatctatc tacctcgacc     600
ggcttctcca gatccgaacg gtaagttgtt ggctccgata cgatcgatca catgtgagct     660
cggcatgctg cttttctgcg cgtgcatgcg gctcctagca ttccacgtcc acgggtcgtg     720
acatcaatgc acgatataat cgtatcggta cagagatatt gtcccatcag ctgctagctt     780
tcgcgtattg atgtcgtgac attttgcacg caggtccgct gtatcacaag gctggtacc     840 acctcttcta ccagtggaac ccggactccg cggtatgggg caacatcacc tggggccacg     900
ccgtctcgcg cgacctcctc cactggctgc acctaccgct ggccatggtg cccgatcacc     960
cgtacgacgc caacggcgtc tggtccgggt cggcgacgcg cctgcccgac ggccggatcg    1020
```

```
tcatgctcta cacgggctcc acggcggagt cgtcggcgca ggtgcagaac ctcgcggagc    1080
cggccgacgc gtccgacccg ctgctgcggg agtgggtcaa gtcggacgcc aacccggtgc    1140
tggtgccgcc gccgggcatc gggccgacgg acttccgcga cccgacgacg gcgtgtcgga    1200
cgccggccgg caacgacacg gcgtggcggg tcgccatcgg gtccaaggac cgggaccacg    1260
cggggctggc gctggtgtac cggacggagg acttcgtgcg gtacgacccg gcgccggcgc    1320
tgatgcacgc cgtgccgggc accggcatgt gggagtgcgt ggacttctac ccggtggccg    1380
cgggatcagg cgccgcggcg ggcagcgggg acgggctgga gacgtccgcg gcgccgggac    1440
ccggggtgaa gcacgtgctc aaggctagcc tcgacgacga caagcacgac tactacgcga    1500
tcggcaccta cgaccggcg acggacacct ggaccccga cagcgcggag gacgacgtcg    1560
ggatcggcct ccggtacgac tatggcaagt actacgcgtc gaagaccttc tacgaccccg    1620
tccttcgccg gcgggtgctc tgggggtggg tcggcgagac cgacagcgag cgcgcggaca    1680
tcctcaaggg ctgggcatcc gtgcaggtac gtctcagggt ttgaggctag catggcttca    1740
atcttgctgg catcgaatca ttaatgggca gatattataa cttgataatc tgggttggtt    1800
gtgtgtggtg gggatggtga cacacgcgcg gtaataatgt agctaagctg gttaaggatg    1860
agtaatgggg ttgcgtataa acgacagctc tgctaccatt acttctgaca cccgattgaa    1920
ggagacaaca gtaggggtag ccggtagggt tcgtcgactt gccttttctt ttttcctttg    1980
ttttgttgtg gatcgtccaa cacaaggaaa ataggatcat ccaacaaaca tggaagtaat    2040
cccgtaaaac atttctcaag gaaccatcta gctagacgag cgtggcatga tccatgcatg    2100
cacaaacact agataggtct ctgcagctgt gatgttcctt tacatatacc accgtccaaa    2160
ctgaatccgg tctgaaaatt gttcaagcag agaggcccg atcctcacac ctgtacacgt    2220
ccctgtacgc gccgtcgtgg tctcccgtga tcctgccccg tccctccac gcggccacgc    2280 ctgctgcagc gctctgtaca agcgtgcacc acgtgagaat ttccgtctac tcgagcctag    2340
tagttagacg ggaaaacgag aggaagcgca cggtccaagc acaacacttt gcgcgggccc    2400
gtgacttgtc tccggttggc tgagggcgcg cgacagagat gtatggcgcc gcggcgtgtc    2460
ttgtgtcttg tcttgcctat acaccgtagt cagagactgt gtcaaagccg tccaacgaca    2520
atgagctagg aaacggttg gagagctggg ttcttgcctt gcctcctgtg atgtctttgc    2580
cttgcatagg gggcgcagta tgtagctttg cgttttactt cacgccaaag gatactgctg    2640
atcgtgaatt attattatta tatatatatc gaatatcgat ttcgtcgctc tcgtggggtt    2700 ttatttttcca gactcaaact tttcaaaagg cctgtgtttt agttcttttc ttccaattga    2760
gtaggcaagg cgtgtgagtg tgaccaacgc atgcatggat atcgtggtag actggtagag    2820
ctgtcgttac cagcgcgatg cttgtatatg tttgcagtat tttcaaatga atgtctcagc    2880
tagcgtacag ttgaccaagt cgacgtggag ggcgcacaac agacctctga cattattcac    2940
ttttttttta ccatgccgtg cacgtgcagt caatccccag gacggtcctc ctggacacga    3000
agacgggcag caacctgctc cagtggccgg tggtggaggt ggagaacctc cggatgagcg    3060
gcaagagctt cgacggcgtc gcgctggacc gcggatccgt cgtgcccctc gacgtcggca    3120
aggcgacgca ggtgacgccg cacgcagcct gctgcagcga acgaactcgc gcgttgccgg    3180
cccgcggcca gctgacttag tttctctggc tgatcgaccg tgtgcctgcg tgcgtgcagt    3240
tggacatcga ggctgtgttc gaggtggacg cgtcggacgc ggcggcgtc acggaggccg    3300 acgtgacgtt caactgcagc accagcgcag gcgcggcggg ccggggcctg ctcggcccgt    3360
```

| | |
|---|---|
| tcggccttct cgtgctggcg gacgacgact tgtccgagca gaccgccgtg tacttctacc | 3420 |
| tgctcaaggg cacggacggc agcctccaaa ctttcttctg ccaagacgag ctcaggtatg | 3480 |
| tatgttatga cttatgacca tgcatgcatg cgcatttctt agctaggctg tgaagcttct | 3540 |
| tgttgagttg tttcacagat gcttaccgtc tgctttgttt cgtatttcga ctaggcatcc | 3600 |
| aaggcgaacg atctggttaa gagagtatac gggagcttgg tccctgtgct agatggggag | 3660 |
| aatctctcgg tcagaatact ggtaagtttt tacagcgcca gccatgcatg tgttggccag | 3720 |
| ccagctgctg gtactttgga cactcgttct tctcgcactg ctcattattg cttctgatct | 3780 |
| ggatgcacta caaattgaag gttgaccact ccatcgtgga gagctttgct caaggcggga | 3840 |
| ggacgtgcat cacgtcgcga gtgtacccca cacgagccat ctacgactcc gcccgcgtct | 3900 |
| tcctcttcaa caacgccaca catgctcacg tcaaagcaaa atccgtcaag atctggcagc | 3960 |
| tcaactccgc ctacatccgg ccatatccgg caacgacgac ttctctatga ctaaattaag | 4020 |
| tgacggacag ataggcgata ttgcatactt gcatcatgaa ctcatttgta caacagtgat | 4080 |
| tgtttaattt atttgctgcc ttccttatcc ttcttgtgaa actatatggt acacacatgt | 4140 |
| atcattaggt ctagtagtgt tgttgcaaag acacttagac accagaggtt ccaggagtat | 4200 |
| cagagataag gtataagagg gagcagggag cag | 4233 |

<210> SEQ ID NO 77
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 77
tgttcggttc cctctaccaa                                          20

<210> SEQ ID NO 78
<211> LENGTH: 22
<212> TYPE: DNA
<213> ORGANISM: Artificial Sequence
<220> FEATURE:
<223> OTHER INFORMATION: synthesized primer oligonucleotide

<400> SEQUENCE: 78
caacatccat caccttgact ga                                       22

<210> SEQ ID NO 79
<211> LENGTH: 24
<212> TYPE: DNA
<213> ORGANISM: Artificial Sequence
<220> FEATURE:
<223> OTHER INFORMATION: synthesized probe oligonucleotide

<400> SEQUENCE: 79
cacagaaccg tcgcttcagc aaca                                     24

<210> SEQ ID NO 80
<211> LENGTH: 18
<212> TYPE: DNA
<213> ORGANISM: Artificial Sequence
<220> FEATURE:
<223> OTHER INFORMATION: synthesized primer oligonucleotide

<400> SEQUENCE: 80
tggcggacga cgacttgt                                            18

```
<210> SEQ ID NO 81
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 81
aaagtttgga ggctgccgt                                              19

<210> SEQ ID NO 82
<211> LENGTH: 26
<212> TYPE: DNA
<213> ORGANISM: Artificial Sequence
<220> FEATURE:
<223> OTHER INFORMATION: synthesized probe oligonucleotide

<400> SEQUENCE: 82
cgagcagacc gccgtgtact tctacc                                      26

<210> SEQ ID NO 83
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 83
cttagctgga taacgccac                                              19

<210> SEQ ID NO 84
<211> LENGTH: 19
<212> TYPE: DNA
<213> ORGANISM: Artificial Sequence
<220> FEATURE:
<223> OTHER INFORMATION: synthesized primer oligonucleotide

<400> SEQUENCE: 84
gaccgtaagg cttgatgaa                                              19

<210> SEQ ID NO 85
<211> LENGTH: 21
<212> TYPE: DNA
<213> ORGANISM: Artificial Sequence
<220> FEATURE:
<223> OTHER INFORMATION: synthesized probe oligonucleotide

<400> SEQUENCE: 85
cgagattctc cgcgctgtag a                                           21

<210> SEQ ID NO 86
<211> LENGTH: 25
<212> TYPE: DNA
<213> ORGANISM: Artificial Sequence
<220> FEATURE:
<223> OTHER INFORMATION: synthesized primer oligonucleotide

<400> SEQUENCE: 86
gtatgtttct gcttctacct ttgat                                       25

<210> SEQ ID NO 87
<211> LENGTH: 29
<212> TYPE: DNA
<213> ORGANISM: Artificial Sequence
<220> FEATURE:
<223> OTHER INFORMATION: synthesized primer oligonucleotide
```

<400> SEQUENCE: 87
ccatgttttg gtcatatatt agaaaagtt                                29

<210> SEQ ID NO 88
<211> LENGTH: 34
<212> TYPE: DNA
<213> ORGANISM: Artificial Sequence
<220> FEATURE:
<223> OTHER INFORMATION: synthesized probe oligonucleotide

<400> SEQUENCE: 88
agtaatatag tatttcaagt attttttca aaat                           34

<210> SEQ ID NO 89
<211> LENGTH: 736
<212> TYPE: DNA
<213> ORGANISM: Euschistus heros

<400> SEQUENCE: 89
gtaagtatag tgcgttaaga ttaattttat ttggattaag ttcttctttc gtgttttaaa      60
tttatagtaa atctaataga taaaaaaact ctcgtattca gtaatgttta gttattgctc     120
tgcttgatga aaccttaatg aagtagttgg atcagtacaa tgcaaatctt cgtgaaaacc     180
ctcacgggta agaccattac cctagaggtt gaaccttcgg atacaatcga aaatgtaaag     240
gctaaaattc aagacaaaga aggaattcct ccagatcagc agaggcttat ttttgctggc     300
aagcagttag aagatggtag aaccttatct gattataaca ttcaaaaaga gtctacccct     360
cacttggttc ttcgtctgag gggtggtgtc attgagccaa ctctgaagat ccttgcacag     420
aaatacaatt gcgataaaat gatttgccgc aagtgctatg ctagacttca tccaagagct     480
accaattgcc gcaagaagaa atgtggtcat actaacaaca tccgcccaa gaagaagctg     540 aagtagatta tctgcttatt tttcaacctg gatttaaaaa aaaaaaaatt caagacataa     600
aaccatgtta aataaatttt taagaaata tatataaaaa aagtaattgt tttttcttaa     660
ttccttttca aatgctatga ttttgttttt tatgtaatct aatttcaaac tgtacaaaaa     720
atatatctgt accaag                                                    736

<210> SEQ ID NO 90
<211> LENGTH: 128
<212> TYPE: PRT
<213> ORGANISM: Euschistus heros

<400> SEQUENCE: 90

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Val Ile Glu Pro
65                  70                  75                  80

Thr Leu Lys Ile Leu Ala Gln Lys Tyr Asn Cys Asp Lys Met Ile Cys
                85                  90                  95

Arg Lys Cys Tyr Ala Arg Leu His Pro Arg Ala Thr Asn Cys Arg Lys
            100                 105                 110

```
        Lys Lys Cys Gly His Thr Asn Asn Ile Arg Pro Lys Lys Lys Leu Lys
            115                 120                 125
```

<210> SEQ ID NO 91
<211> LENGTH: 410
<212> TYPE: DNA
<213> ORGANISM: Euschistus heros

<400> SEQUENCE: 91

```
gcaaatcttc gtgaaaaccc tcacgggtaa gaccattacc ctagaggttg aaccttcgga       60
tacaatcgaa aatgtaaagg ctaaaattca agacaaagaa ggaattcctc cagatcagca      120
gaggcttatt tttgctggca agcagttaga agatggtaga accttatctg attataacat      180
tcaaaaagag tctacccttc acttggttct tcgtctgagg ggtggtgtca ttgagccaac      240
tctgaagatc cttgcacaga aatacaattg cgataaaatg atttgccgca agtgctatgc      300
tagacttcat ccaagagcta ccaattgccg caagaagaaa tgtggtcata ctaacaacat      360
ccgccccaag aagaagctga agtagattat ctgcttattt ttcaacctgg               410
```

<210> SEQ ID NO 92
<211> LENGTH: 132
<212> TYPE: DNA
<213> ORGANISM: Euschistus heros

<400> SEQUENCE: 92

```
tgatttgccg caagtgctat gctagacttc atccaagagc taccaattgc cgcaagaaga       60
aatgtggtca tactaacaac atccgcccca agaagaagct gaagtagatt atctgcttat      120
ttttcaacct gg                                                          132
```

<210> SEQ ID NO 93
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 93

```
ttaatacgac tcactatagg gagagcaaat cttcgtgaaa accctcac                    48
```

<210> SEQ ID NO 94
<211> LENGTH: 50
<212> TYPE: DNA
<213> ORGANISM: Artificial Sequence
<220> FEATURE:
<223> OTHER INFORMATION: synthesized primer oligonucleotide

<400> SEQUENCE: 94

```
ttaatacgac tcactatagg gagaccaggt tgaaaaataa gcagataatc                  50
```

<210> SEQ ID NO 95
<211> LENGTH: 301
<212> TYPE: DNA
<213> ORGANISM: Artificial Sequence
<220> FEATURE:
<223> OTHER INFORMATION: synthesized artificial sequence

<400> SEQUENCE: 95

```
catctggagc acttctcttt catgggaaga ttccttacgt tgtggagatg aagggaatg        60 ttgatggcca cacctttagc atacgtggga aaggctacgg agatgcctca gtgggaaagg      120
ttgatgcaca gttcatctgc acaactggtg atgttcctgt gccttggagc acacttgtca      180
```

```
ccactctcac ctatggagca cagtgctttg ccaagtatgg tccagagttg aaggacttct      240
acaagtcctg tatgccagat ggctatgtgc aagagcgcac aatcaccttt gaaggagatg      300
g                                                                     301
```

```
<210> SEQ ID NO 96
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 96
ttaatacgac tcactatagg gagagcatct ggagcacttc tctttca                    47
```

```
<210> SEQ ID NO 97
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 97
ttaatacgac tcactatagg gagaccatct ccttcaaagg tgattg                     46
```

```
<210> SEQ ID NO 98
<211> LENGTH: 574
<212> TYPE: RNA
<213> ORGANISM: Diabrotica virgifera

<400> SEQUENCE: 98
aaguugggua uaaaccacgu ucaagagag gcaaaaaacc aacggaaaau gcagauauuc        60
guuaaaacuu uaaccgguaa gaccaucaca cuugaggucg agccaagcga cacaaucgaa      120
aaugucaagg cgaaaauucca agacaaagag gguauuccac cagaucagca cgucuaauu      180 uuugcuggca aacaauugga agauggacgu acauugccg auuacaacau ccaaaaggaa       240
ucgacacucc auuuggucuu acgucuacgu gguggauaca ucgaaccauc auugcguauu      300
uuggcacaaa aguacaauug cgacaaaaug auuugccgua agucuaugc ucguuugcau       360 ccaagagcaa ccaauugccg uaagaagaag uguggccaca ccaacaauuu gcgcccaaag      420
aagaaguuga aguagacgau cguauuuuug ugcuguaugu cuggaggaaa acaauguucg      480
gauucgucca caguuguuau cauuuugaau aaucgaaauu augugaauca ucauuggguu      540
acagccugaa uaaacuucgu uuucugaaac cggc                                  574
```

```
<210> SEQ ID NO 99
<211> LENGTH: 652
<212> TYPE: RNA
<213> ORGANISM: Diabrotica virgifera

<400> SEQUENCE: 99
auuaaauauc uguacuuuua aauuuaccac gcuuuugua acggaaacgu guucaucaac        60
ugucacuuau caaauaaacu agacuucauu uuucacuugu cuuuuucauu cggaaguuag      120
cacguugugg aauaaacacu uccacaaugc aaauuuucgu gaaaacucuc acugguaaaa      180
ccaucacccu cgagguugag ccauccgaua caaucgaaaa uguaaagcu aagauccaag       240 acaaagaagg uaucccccca gaccagcaac guuugaucuu cgcuggaaaa caacucgaag      300
auggacguac cuugucagac uacaacaucc agaaggaauc cacccuucac uuggugcucc      360
gauugagagg aggucucauc gagccuuccc uucguauuuu agccaugaag uacaacugcg      420
```

| | |
|---|---|
| agaagaugau cugccguaaa uguuacgcca gguuacaccc aagggccacc aacugcagaa | 480 |
| agaagaagug uggacacacc aacaacuugc gccccaagaa gaagcuaaag uagacuauua | 540 |
| cgagguuauu uuuuacaaug uuaauaucuu acaauuccag auguuacuug aacauuuauu | 600 |
| uaacuaauua uaggaaauga caucaauccu aaaaaaaaaa aaaaaaaaaa aa | 652 |

<210> SEQ ID NO 100
<211> LENGTH: 4065
<212> TYPE: RNA
<213> ORGANISM: Diabrotica virgifera

<400> SEQUENCE: 100

| | |
|---|---|
| cagauuuucg ucaagacauu gacggggaag accauuaccc uggaggucga gcccagugau | 60 |
| uccaucgaga ccgucaaauc caagauucag gauaaggaag ggauuccucc ugaccaacag | 120 |
| cgcuugauuu uugcuggcaa gcaacucgag gaaggccgau cuuugucaga cuauaacauc | 180 |
| caaaaagaga guaccaucca ucucgugcuu cgacgugagg gagguggguau cgagaucgag | 240 |
| ccaacguugg cgcaauuggc ucgcaagcac aauauugaga gacucauuug ucgaaaaugu | 300 |
| uacgccagac uacacaucaa agcuacuaau ugccggaaaa aggccugcgg ccacucaucu | 360 |
| cagcucagac ccaagaagaa gccuaagagu uaauaauuuu ugaacuuucu uuuuuccacg | 420 |
| aacuagcuua uguguacucg ucaguuguu ucuucucagc cgccgauucu ucuggcccga | 480 |
| aacccaaguc guccucuuug uacagaaaug ugucucgccg cacuaugucg cuaacuaagc | 540 |
| augacucgau cgucgaccac uccaguggggc gcucacgugc uugcguucg gcgagguaca | 600 |
| gcacgcgguu gacgcgauuu uugaauacg cauugagcau cgacaccacc ucgcucgccu | 660 |
| ccucccggag uccaguuuuc cugacggacu ugaugccgag cggaccaccg uauucauuug | 720 |
| acgcucgguc caguaggcgu ugggugaacg cccaaccguc uucucuuuga ggcucuugug | 780 |
| ggguggugcau cccacuaccg uaguggugau uguuagaugc ggccguuggc ggugugucgu | 840 |
| ccucagcuuc aaagagcauc cucagacuac ccucagucga cacaggcugg uuggugaga | 900 |
| gccccccaaaa ugcgcucuca gagaauggcc caagcgugaa gaacgccaa uccuccgcgc | 960 |
| aacuggacac aacuggcggc ccugccgaau uuacaguuug cugagccggc auucuccgaa | 1020 |
| aagcugguuc cugaucaauc aaaccaugau ccucugaauu guuuccaaa ugaucagcca | 1080 |
| accuuucaua cauacgccga gccguaucuc guauugcuga augcgacaaa gcuccgcgg | 1140 |
| guuuauagcc ggcacgugcc ugccguagca acgcuaugac gaaccucgcc aucgccgucu | 1200 |
| ucggcacuau gauguucuug cguuuagcc aagcgaucug ccgacaugaa ucagaccgcc | 1260 |
| ccuucaugaa cgaauaauca gguaccacag ccuucaccgg agcgcgcagg uuauuguuca | 1320 |
| ucauuuguag cuccguaga gucccaggcc guccaacgag cagggccgag cggcggagu | 1380 |
| ucaucaagcc gcgauagggg accagucggg ggaggccgcg gagcaguucc ggcugcauau | 1440 |
| uagguggaga ugagccaacg ccaucgagac ucugcgggcc gccgaauccc ggcaugucca | 1500 |
| ucauuccuug ggcacugaga cuuggcgagu ucaucgaauu cggcgucugg ccuuccauca | 1560 |
| ugcuguucag agaucccgga ggcgccggcu gacuggugaa ggucggacuc ugccgccag | 1620 |
| agcccaugu uuggccaggc ggcugcggca uagcgccucc agcgugcauc aucauuugcu | 1680 |
| guugcugcau cauuuguugc uggagcaugu acggcggcug uuguggaggu ggcaucaugc | 1740 |
| guugaggcgc cggcuggaua uugccagcgu gcauaaucgg cgucaucgag uucauaccca | 1800 |
| ucaucguacu cugcaucaua ggugaugca uuggcgcuga agccaugacu ugagggguucg | 1860 |

-continued

```
gcgcgccgua cauuugaccc uggggcggcg gcugggcucc gggaggyggc ugccagcgcu    1920
guugcuguug cugagcuugu ugcugugguu ucgguacaua ucuauuaguu ggggccucc      1980 auguauuaug caucgucaga guggccgugc gauugaguuu ucgagcauaa aaagugcggc    2040
cucagugauu gggaaugauc auuucggcag ucggagucuu guauggccug aguaucagag    2100
acguagucca agagaucuug cucgugcugc gaggcagcaa gggaccguua aucguaauga    2160
agggcugaug uuugccauug uccgugcgug aagucaaguc uaggacugug ccgugacaag    2220
cuauggccgu aaacucaauu uccaguucgu agcuaacucc aacucguuca ugucggaagg    2280
uagccucuag acuggcaggg auguagagcg gaacuaucgc aaccaggguc ugcguaacag    2340
ucguggaggc uucacacaca gccacggugu ccgucguuau aacaaucagc guugaaucua    2400
cauucgucaa cgcgugguag cuucugaaau ccagccaacu caaaccgguc guggcguugg    2460
gccgguaccc gaaauuuugu cuaugcuugu uccacugaag cgccucgagc ggagacagug    2520
gcggcugaua agaccucgua guuuguuuca aucuaacaca cacuuccacc acggccaaag    2580
acgaauuagu gaauucgguc uugacauaaa uguacuacc uaggugcccc ucaagagugu     2640 augcucauc aacagugguu ggugcgauu uauugcccuc guacacuuug gauucggcg      2700 ucgccaaaca aacgucugcu ggccauauau ugacgacuug gauaucggac agaugggaac    2760
cauugaucga aacucuguag acggggguag uuggggggcg caccugugca uccgcuucaa    2820
aagaugagac aaaauugccu gcaguuccuu uuugacucuu agagcugcuc augcaccuga    2880
ucgagccgac aaucuuauca aucucaaauc cauuuccgag cuuucgaug agauucaccu     2940 cauggacagc gcgcugcuga auuucugcc ucaauaacuu caagcauucu ccaggcucuu     3000
cuaagaauuc guucaaagcu gcagcagaua ucccuguugc cgucauaugc uucgcuggcc    3060
gaguuucgcu caaagugcua ugcauaucag cacaggugua acugagccau cugagauaua    3120
agaguccggc aucaaccuuu ucuuggcga cgagaaaauc auuugugau ucuuguucau      3180 ugugugacca gccagcuauc gggagcggaa ugggcagaga gccagaagug aaagcggcuc    3240 cgaaaucccca auuuaaggcg agguaggugg gggugaaggg ccgagcuggu agcgguggau   3300
auauaggcgg agguuguaga augauagaag cgagcugcgu gaacuucaua aagauggggga  3360 uccauucacu uaaggggguug aucagaauag gacacgggcu aauugguuauu gccaagcuua  3420 uuugcggcgg gauuggcggc ccuggagcgc cguuuguugg aguagauauu ucggacucga    3480
uacugucgag ggugcuggcg cgagcuggag ggaggugccu cacggaugag ccgccgcucg    3540
cgcuacgauc auucaaaccu accgacccac uauuguugug ugaaaguaga guugcuccgc    3600
ccguuggccc aauagucaca ggcgcgucau uucugauagc uagaacguag ucauagcuga    3660 aucgccucc ucgucggaug gacgguggca agcuaacugg gauguagagc uggcauuugu     3720
accuguccac gucgccugug accucgagag uauugcuuag cgcgaacacu cgcccugauu    3780 ucuuauggu ggugcggag guggcuuguu uugaugucc gggggauggg agcguaguag       3840
uggaaacgga uuuccaaac ucucugaggg cucuagugac uaccucguaa ccauuugaa      3900 cuuugucagu agagaauaac gggggggcug augggacagcg aucggugucc aauccguuga   3960
ccagaccaua cacguauauu cgaucaccgg cggugaagug ggugugacaa aaacugaugg    4020
acuggccacc ucuaggcauu cauuuaaucu ggcaagguguu ccgcu                  4065
```

<210> SEQ ID NO 101
<211> LENGTH: 306
<212> TYPE: RNA
<213> ORGANISM: Diabrotica virgifera

<400> SEQUENCE: 101
gaaaauguca aggcgaaaau ccaagacaaa gagggauuuc caccagauca gcaacgucua    60
auuuuugcug gcaaacaauu ggaagaugga cguacauugu ccgauuacaa cauccaaaag   120
gaaucgacac uccauuuggu guuacgucua cguggugua ucaucgaacc aucauugcgu    180
auuuuggcac aaaaguacaa uugcgacaaa augauuugcc guaagugcua ugcucguuug   240
cauccaagag caaccaauug ccguaagaag aaguguggcc acaccaacaa uuugcgccca   300
aagaag                                                              306

<210> SEQ ID NO 102
<211> LENGTH: 361
<212> TYPE: RNA
<213> ORGANISM: Diabrotica virgifera

<400> SEQUENCE: 102
cagauuuucg ucaagacauu gacggggaag accauuaccc uggaggucga gcccagugau   60
uccaucgaga ccgucaaauc caagauucag gauaaggaag ggauuccucc ugaccaacag   120
cgcuugauuu uugcuggcaa gcaacucgag gaaggccgau cuuugucaga cuauaacauc   180 caaaagaga guaccaucca ucucgugcuu cgacugagag gaggugguau cgagaucgag   240
ccaacguugg cgcaauuggc ucgcaagcac aauauugaga gacucauuug ucgaaaaugu   300
uacgccagac uacacaucaa agcuacuaau ugccggaaaa aggccugcgg ccaucaucu    360 c                                                                   361

<210> SEQ ID NO 103
<211> LENGTH: 117
<212> TYPE: RNA
<213> ORGANISM: Diabrotica virgifera

<400> SEQUENCE: 103
ccaccagauc agcaacgucu aauuuuugcu ggcaaacaau uggaagaugg acguacauug    60
uccgauuaca acauccaaaa ggaaucgaca cuccauuugg uguuacgucu acgugu        117

<210> SEQ ID NO 104
<211> LENGTH: 143
<212> TYPE: RNA
<213> ORGANISM: Diabrotica virgifera

<400> SEQUENCE: 104
ucgaaccauc auugcguauu uuggcacaaa aguacaauug cgacaaaaug auuugccgua    60
agugcuaugc ucguuugcau ccaagagcaa ccaauugccg uaagaagaag uguggccaca   120
ccaacaauuu gcgcccaaag aag                                           143

<210> SEQ ID NO 105
<211> LENGTH: 141
<212> TYPE: RNA
<213> ORGANISM: Diabrotica virgifera

<400> SEQUENCE: 105
caagagaggc aaaaaccaa cggaaaaugc agauauucgu aaaacuuua accgguaaga     60 ccaucacacu ugaggucgag ccaagcgaca caaucgaaaa ugucaaggcg aaaauccaag   120
acaaagaggg uauuccacca g                                             141

<210> SEQ ID NO 106

```
<211> LENGTH: 130
<212> TYPE: RNA
<213> ORGANISM: Diabrotica virgifera

<400> SEQUENCE: 106
gccguaagug cuaugcucgu uugcauccaa gagcaaccaa uugccguaag aagaagugug      60
gccacaccaa caauuugcgc ccaaagaaga aguugaagua gacgaucgua uuuugugcu     120 guaugucugg                                                           130

<210> SEQ ID NO 107
<211> LENGTH: 165
<212> TYPE: RNA
<213> ORGANISM: Diabrotica virgifera

<400> SEQUENCE: 107
cagcaacguc uaauuuuugc uggcaaacaa uuggaagaug gacguacauu guccgauuac      60
aacauccaaa aggaaucgac acuccauuug guguuacguc uacgugguggg uaucaucgaa    120 ccaucauugc guauuuuggc acaaaaguac aauugcgaca aaaug                    165

<210> SEQ ID NO 108
<211> LENGTH: 736
<212> TYPE: RNA
<213> ORGANISM: Euschistus heros

<400> SEQUENCE: 108
guaaguauag ugcguuaaga uuaauuuuau uuggauuaag uucuucuuuc uguuuuaaa       60 uuuauaguaa aucuaauaga uaaaaaaacu cucguauuca guaaguuua guuauugcuc    120 ugcuugauga aaccuuaaug aaguaguugg aucaguacaa ugcaaaucuu cgugaaaacc    180
cucacgggua agaccauuac ccuagagguu gaaccuucgg auacaaucga aaauguaaag   240
gcuaaaauuc aagacaaaga aggaauuccu ccagaucagc agaggcuuau uuugcuggc    300 aagcaguuag aagaugguag aaccuuaucu gauuauaaca uucaaaaaga gcuacccuu    360 cacuggguuc uucgucugag ggguggguguc auugagccaa cucugaagau ccuugcacag  420
aaauacaauu gcgauaaaau gauuugccgc aagugcuaug cuagacuuca uccaagagcu   480
accaauugcc gcaagaagaa augggucau acuaacaaca uccgcccaa gaagaagcug    540 aaguagauua ucugcuuauu uuucaaccug gauuuaaaa aaaaaaaauu caagacauaa   600
aaccauguua aauaaauuu uuaagaaaua uauauaaaa aaguaauugu uuuucuuaa    660 uuccuuuuca aaugcuauga uuuuguuuu uauguaaucu aauuucaaac ugacaaaaa    720 auauaucugu accaag                                                   736

<210> SEQ ID NO 109
<211> LENGTH: 410
<212> TYPE: RNA
<213> ORGANISM: Euschistus heros

<400> SEQUENCE: 109
gcaaaucuuc gugaaaaccc ucacggguaa gaccauuacc cuagagguug aaccuucgga    60
uacaaucgaa aauguaaagg cuaaaauuca agacaaagaa ggaauuccuc cagaucagca   120
gaggcuuauu uugcuggca agcaguuaga agaugguaga accuuaucug auuauaacau   180
ucaaaaagag cuacccuuc acuggguucu cgucugagg ggugugucau uagagccaac   240
ucugaagauc cuugcacaga aauacaauug cgauaaaaug auuugccgca agugcuaugc   300
uagacuucau ccaagagcua ccaauugccg caagaagaaa ugggucaua cuaacaacau   360
```

```
ccgccccaag aagaagcuga aguagauuau cugcuuauuu uucaaccugg          410

<210> SEQ ID NO 110
<211> LENGTH: 132
<212> TYPE: RNA
<213> ORGANISM: Euschistus heros

<400> SEQUENCE: 110
ugauuugccg caagugcuau gcuagacuuc auccaagagc uaccaauugc cgcaagaaga    60
aaugugguca uacuaacaac auccgcccca agaagaagcu gaaguagauu aucugcuuau   120
uuuucaaccu gg                                                      132

<210> SEQ ID NO 111
<211> LENGTH: 153
<212> TYPE: DNA
<213> ORGANISM: Artificial Sequence
<220> FEATURE:
<223> OTHER INFORMATION: synthesized probe oligonucleotide

<400> SEQUENCE: 111
agtcatcacg ctggagcgca catataggcc ctccatcaga aagtcattgt gtatatctct    60
catagggaac gagctgcttg cgtatttccc ttccgtagtc agagtcatca atcagctgca   120
ccgtgtcgta aagcgggacg ttcgcaagct cgt                                153

<210> SEQ ID NO 112
<211> LENGTH: 153
<212> TYPE: DNA
<213> ORGANISM: Artificial Sequence
<220> FEATURE:
<223> OTHER INFORMATION: linker polynucleotide

<400> SEQUENCE: 112
agtcatcacg ctggagcgca catataggcc ctccatcaga aagtcattgt gtatatctct    60
catagggaac gagctgcttg cgtatttccc ttccgtagtc agagtcatca atcagctgca   120
ccgtgtcgta aagcgggacg ttcgcaagct cgt                                153
```

RIBOSOMAL PROTEIN L40 (RPL40) NUCLEIC ACID MOLECULES THAT CONFER RESISTANCE TO COLEOPTERAN AND HEMIPTERAN PESTS

PRIORITY CLAIM

This application claims the benefit of the filing date of U.S. Provisional Patent Application Ser. No. 62/269,382, filed Dec. 18, 2015, which is incorporated herein in its entirety.

TECHNICAL FIELD

The present invention relates generally to genetic control of plant damage caused by coleopteran and/or hemipteran pests. In particular embodiments, the present disclosure relates to identification of target coding and non-coding sequences, and the use of recombinant DNA technologies for post-transcriptionally repressing or inhibiting expression of target coding and non-coding sequences in the cells of a coleopteran and/or hemipteran pest to provide a plant protective effect.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in the Americas: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; *D. speciosa* Germar; and *D. u. undecimpunctata* Mannerheim. The United States Department of Agriculture estimates that corn rootworms cause $1 billion in lost revenue each year, including $800 million in yield loss and $200 million in treatment costs.

Both WCR and NCR eggs are deposited in the soil during the summer. The insects remain in the egg stage throughout the winter. The eggs are oblong, white, and less than 0.004 inches (0.010 cm) in length. The larvae hatch in late May or early June, with the precise timing of egg hatching varying from year to year due to temperature differences and location. The newly hatched larvae are white worms that are less than 0.125 inches (0.3175 cm) in length. Once hatched, the larvae begin to feed on corn roots. Corn rootworms go through three larval instars. After feeding for several weeks, the larvae molt into the pupal stage. They pupate in the soil, and then they emerge from the soil as adults in July and August. Adult rootworms are about 0.25 inches (0.635 cm) in length.

Corn rootworm larvae complete development on corn and several other species of grasses. Larvae reared on yellow foxtail emerge later and have a smaller head capsule size as adults than larvae reared on corn (Ellsbury et al. (2005) Environ. Entomol. 34:627-634). WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis* (Bt)), transgenic plants that express Bt toxins, or a combination thereof. Crop rotation suffers from the disadvantage of placing unwanted restrictions upon the use of farmland. Moreover, oviposition of some rootworm species may occur in crop fields other than corn or extended diapause results in egg hatching over multiple years, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity of many of them to non-target species.

Stink bugs and other hemipteran insects (heteroptera) are another important agricultural pest complex. Worldwide over 50 closely related species of stink bugs are known to cause crop damage (McPherson & McPherson, R. M. (2000) *Stink bugs of economic importance in America north of Mexico* CRC Press). These insects are present in a large number of important crops including maize, soybean, fruit, vegetables, and cereals.

Stink bugs go through multiple nymph stages before reaching the adult stage. The time to develop from eggs to adults is about 30-40 days. Both nymphs and adults feed on sap from soft tissues into which they also inject digestive enzymes causing extra-oral tissue digestion and necrosis. Digested plant material and nutrients are then ingested. Depletion of water and nutrients from the plant vascular system results in plant tissue damage. Damage to developing grain and seeds is the most significant as yield and germination are significantly reduced. Multiple generations occur in warm climates resulting in significant insect pressure. Current management of stink bugs relies on insecticide treatment on an individual field basis. Therefore, alternative management strategies are urgently needed to minimize ongoing crop losses.

RNA interference (RNAi) is a process utilizing endogenous cellular pathways, whereby an interfering RNA (iRNA) molecule (e.g., a dsRNA molecule) that is specific for all, or any portion of adequate size, of a target gene sequence results in the degradation of the mRNA encoded thereby. In recent years, RNAi has been used to perform gene "knockdown" in a number of species and experimental systems; for example, *Caenorhabditis elegans*, plants, insect embryos, and cells in tissue culture. See, e.g., Fire et al. (1998) Nature 391:806-811; Martinez et al. (2002) Cell 110:563-574; McManus and Sharp (2002) Nature Rev. Genetics 3:737-747.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Post-transcriptional gene silencing occurs when the guide strand binds specifically to a complementary sequence of an mRNA molecule and induces cleavage by Argonaute, the catalytic component of the RISC complex. This process is known to spread systemically throughout some eukaryotic organisms despite initially limited concentrations of siRNA and/or miRNA such as plants, nematodes, and some insects.

U.S. Pat. No. 7,612,194 and U.S. Patent Publication Nos. 2007/0050860, 2010/0192265, and 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. 2007/0050860 to operably link to a promoter a nucleic acid molecule that is complementary to one of several particular partial sequences of *D. v. virgifera* vacuolar-type $H^+$-ATPase (V-ATPase) disclosed therein for the expression of anti-sense RNA in plant cells. U.S. Patent Publication No. 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midguts, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. 2007/0050860, 2010/0192265 and 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. 2007/0050860 and 2010/0192265, and 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA. U.S. Patent Application Publication No. U.S. 2013/040173 and PCT Application Publication No. WO 2013/169923 describes the use of a sequence derived from a *Diabrotica virgifera* Snf7 gene for RNA interference in maize. (Also disclosed in Bolognesi et al. (2012) PLoS ONE 7(10): e47534. doi:10.1371/journal.pone.0047534).

The overwhelming majority of sequences complementary to corn rootworm DNAs (such as the foregoing) are not lethal in species of corn rootworm when used as dsRNA or siRNA. For example, Baum et al. (2007, Nature Biotechnology 25:1322-1326), describe the effects of inhibiting several WCR gene targets by RNAi. These authors reported that 8 of the 26 target genes they tested were not able to provide experimentally significant coleopteran pest mortality at a very high iRNA (e.g., dsRNA) concentration of more than 520 $ng/cm^2$.

The authors of U.S. Pat. No. 7,612,194 and U.S. Patent Publication No. 2007/0050860 made the first report of in planta RNAi in corn plants targeting the western corn rootworm (Baum et al. (2007) Nat. Biotechnol. 25(11):1322-6). These authors describe a high-throughput in vivo dietary RNAi system to screen potential target genes for developing transgenic RNAi maize. Of an initial gene pool of 290 targets, only 14 exhibited larval control potential. One of the most effective double-stranded RNAs (dsRNA) targeted a gene encoding vacuolar ATPase subunit A (V-ATPase), resulting in a rapid suppression of corresponding endogenous mRNA and triggering a specific RNAi response with low concentrations of dsRNA. Thus, these authors documented for the first time the potential for in planta RNAi as a possible pest management tool, while simultaneously demonstrating that effective targets could not be accurately identified a priori, even from a relatively small set of candidate genes.

SUMMARY

Disclosed herein are nucleic acid molecules (e.g., target genes, DNAs, dsRNAs, siRNAs, shRNA, miRNAs, and hpRNAs), and methods of use thereof, for the control of coleopteran pests, including, for example, *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; *D. speciosa* Germar; and *D. u. undecimpunctata* Mannerheim and hemipteran pests, including, for example, *Euschistus heros* (Fabr.) (Neotropical Brown Stink Bug, "BSB"), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois). In particular examples, exemplary nucleic acid molecules are disclosed that may be homologous to at least a portion of one or more native nucleic acid sequences in a coleopteran and/or hemipteran pest.

In these and further examples, the native nucleic acid sequence may be a target gene, the product of which may be, for example and without limitation: involved in a metabolic process or involved in larval/nymph development. In some examples, post-translational inhibition of the expression of a target gene by a nucleic acid molecule comprising a sequence homologous thereto may be lethal in coleopteran and/or hemipteran pests, or result in reduced growth and/or development. In specific examples, a gene encoding a fusion protein that is post-translationally cleaved into ribosomal protein RpL40 and a mono-ubiquitin (referred to herein collectively as rpL40) may be selected as a target gene for post-transcriptional silencing. In particular examples, a target gene useful for post-transcriptional inhibition is the novel gene referred to herein as rpL40. An isolated nucleic acid molecule comprising a nucleotide sequence of rpL40 (SEQ ID NOs:1, 3, 5, and 89); the complement of rpL40 (SEQ ID NOs:1, 3, 5, and 89); and fragments of any of the foregoing is therefore disclosed herein.

Also disclosed are nucleic acid molecules comprising a nucleotide sequence that encodes a polypeptide that is at least 85% identical to an amino acid sequence within a target gene product (for example, the product of a gene referred to as RPL40 and/or mono-ubiquitin, collectively referred to herein as RPL40). For example, a nucleic acid molecule may comprise a nucleotide sequence encoding a polypeptide that is at least 85% identical to an amino acid sequence of SEQ ID NOs:2, 4, 6, 7, 8, and 90 (RPL40 protein). In particular examples, a nucleic acid molecule comprises a nucleotide sequence encoding a polypeptide that is at least 85% identical to an amino acid sequence within a product of RPL40. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, shRNA, miRNA, and hpRNA) molecules that are complementary to all or part of a coleopteran and/or hemipteran pest target gene, for example: rpL40. In particular embodiments, dsRNAs, siRNAs, shRNAs, miRNAs, and/or hpRNAs may be produced in vitro or in vivo by a genetically-modified organism, such as a plant or bacterium. In particular examples, cDNA molecules are disclosed that may be used to produce iRNA molecules that are complementary to all or part of rpL40 (S SEQ ID NOs:1, 3, 5, and 89).

Further disclosed are means for inhibiting expression of an essential gene in a coleopteran and/or hemipteran pest, and means for protecting a plant from coleopteran and/or hemipteran pests. A means for inhibiting expression of an essential gene in a coleopteran and/or hemipteran pest is a single- or double-stranded RNA molecule consisting of at least one of SEQ ID NO:9 (*Diabrotica* rpL40-1 region 1, herein sometimes referred to as rpL40-1 reg1), or SEQ ID NO:10 (*Diabrotica* rpL40-3 region 3, herein sometimes referred to as rpL40-3 reg3), or SEQ ID NO:11 (*Diabrotica* rpL40-1 version 1, herein sometimes referred to as rpL40-1 v1), or SEQ ID NO:12 (*Diabrotica* rpL40-1 version 2, herein sometimes referred to as rpL40-1 v2), or SEQ ID NO:13 (*Diabrotica* rpL40-1 version 3, herein sometimes referred to as rpL40-1 v3), or SEQ ID NO:14 (*Diabrotica* rpL40-1 version 4, herein sometimes referred to as rpL40-1 v4), or SEQ ID NO:15 (*Diabrotica* rpL40-1 version 5, herein sometimes referred to as rpL40-1 v5), or SEQ ID NO:91 (*Euschistus heros* rpL40 region 1, herein sometimes referred to as BSB_rpL40 reg1), or SEQ ID NO:92 (*Euschistus heros* rpL40 version 1, herein sometimes referred to as BSB_rpL40 v1), or the complement thereof. Functional equivalents of means for inhibiting expression of an essential gene in a coleopteran and/or hemipteran pest include single- or double-stranded RNA molecules that are substantially homologous to all or part of a WCR or BSB gene comprising SEQ ID NOs:1, 3, 5, or 89. A means for protecting a plant from coleopteran and/or hemipteran pests is a DNA molecule comprising a nucleic acid sequence encoding a means for inhibiting expression of an essential gene in a coleopteran and/or hemipteran pest operably linked to a promoter, wherein the DNA molecule is capable of being integrated into the genome of a plant.

Disclosed are methods for controlling a population of an insect pest (e.g., a coleopteran or hemipteran pest), comprising providing to an insect pest (e.g., a coleopteran or hemipteran pest) an iRNA (e.g., dsRNA, siRNA, shRNA, miRNA, and hpRNA) molecule that functions upon being taken up by the pest to inhibit a biological function within the pest.

In some embodiments, methods for controlling a population of a coleopteran pest comprises providing to the coleopteran pest an iRNA molecule that comprises all or part of a polynucleotide selected from the group consisting of: SEQ ID NO:98; the complement of SEQ ID NO:98; SEQ ID NO:99; the complement of SEQ ID NO:99; SEQ ID NO:100; the complement of SEQ ID NO:100; SEQ ID NO:101; the complement of SEQ ID NO:101; SEQ ID NO:102; the complement of SEQ ID NO:102; SEQ ID NO:103; the complement of SEQ ID NO:103; SEQ ID NO:104; the complement of SEQ ID NO:104; SEQ ID NO:105; the complement of SEQ ID NO:105; SEQ ID NO:106; the complement of SEQ ID NO:106; SEQ ID NO:107; the complement of SEQ ID NO:107; a polynucleotide that hybridizes to a native rpL40 polynucleotide of a coleopteran pest (e.g., WCR); the complement of a polynucleotide that hybridizes to a native rpL40 polynucleotide of a coleopteran pest; a polynucleotide that hybridizes to a native coding polynucleotide of a *Diabrotica* organism (e.g., WCR) comprising all or part of any of SEQ ID NOs:1, 3, 5 and 9-15; and the complement of a polynucleotide that hybridizes to a native coding polynucleotide of a *Diabrotica* organism comprising all or part of any of SEQ ID NOs:1, 3, 5, and 9-15.

In some embodiments, a methods for controlling a population of a hemipteran pest comprises providing to the hemipteran pest an iRNA molecule that comprises all or part of a polynucleotide selected from the group consisting of: SEQ ID NO:108; the complement of SEQ ID NO:108; SEQ ID NO:109; the complement of SEQ ID NO:109; SEQ ID NO:110; the complement of SEQ ID NO:110; a polynucleotide that hybridizes to a native rpL40 polynucleotide of a hemipteran pest (e.g., BSB); the complement of a polynucleotide that hybridizes to a native rpL40 polynucleotide of a hemipteran pest; a polynucleotide that hybridizes to a native coding polynucleotide of a hemipteran organism (e.g., BSB) comprising all or part of any of SEQ ID NOs:76, 78, and 80-82; and the complement of a polynucleotide that hybridizes to a native coding polynucleotide of a hemipteran organism comprising all or part of any of SEQ ID NOs:76, 78, and 80-82.

In particular embodiments, an iRNA that functions upon being taken up by an insect pest to inhibit a biological function within the pest is transcribed from a DNA comprising all or part of a polynucleotide selected from the group consisting of: SEQ ID NOs:1, 3, 5, 9-15, 89, and 91-92; the complement of SEQ ID NOs:1, 3, 5, 9-15, 89, and 91-92; a native coding sequence of a *Diabrotica* organism (e.g., WCR) or hemipteran organism (e.g. BSB) comprising all or part of any of SEQ ID NOs:1, 3, 5, 9-15, 89, and 91-92; the complement of a native coding sequence of a *Diabrotica* organism or hemipteran organism comprising all or part of any of SEQ ID NOs:1, 3, 5, 9-15, 89, and 91-92; a native non-coding sequence of a *Diabrotica* organism or hemipteran organism that is transcribed into a native RNA molecule comprising all or part of any of SEQ ID NOs:1, 3, 5, 9-15, 89, and 91-92; and the complement of a native non-coding sequence of a *Diabrotica* organism or hemipteran organism that is transcribed into a native RNA molecule comprising all or part of any of SEQ ID NOs:1, 3, 5, 9-15, 89, and 91-92.

Also disclosed herein are methods wherein dsRNAs, siRNAs, shRNAs, miRNAs, and/or hpRNAs may be provided to a coleopteran and/or hemipteran pest in a diet-based assay, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by coleopteran pest larvae and/or hemipteran pest nymphs. Ingestion of dsRNAs, siRNA, shRNAs, miRNAs, and/or hpRNAs of the invention may then result in RNAi in the larvae or nymph, which in turn may result in silencing of a gene essential for viability of the coleopteran and/or hemipteran pest and leading ultimately to larval/nymph mortality. Thus, methods are disclosed wherein nucleic acid molecules comprising exemplary nucleic acid sequence(s) useful for control of coleopteran and/or hemipteran pests are provided to a coleopteran and/or hemipteran pest. In particular examples, the coleopteran and/or hemipteran pest controlled by use of nucleic acid molecules of the invention may be WCR, NCR, SCR, MCR, *D. balteata, D. u. tenella, D. speciosa, D. u. undecimpunctata, Euschistus heros, E. servus, Piezodorus guildinii, Halyomorpha halys, Nezara viridula, Chinavia hilare, C. marginatum, Dichelops melacanthus, D. furcatus, Edessa meditabunda, Thyanta perditor, Horcias nobilellus, Taedia stigmosa, Dysdercus peruvianus, Neomegalotomus parvus, Leptoglossus zonatus, Niesthrea sidae, Lygus hesperus*, and/or *Lygus lineolaris*.

The foregoing and other features will become more apparent from the following Detailed Description of several embodiments, which proceeds with reference to the accompanying FIGS. 1 and 2.

SEQUENCE LISTING

Figure 1:
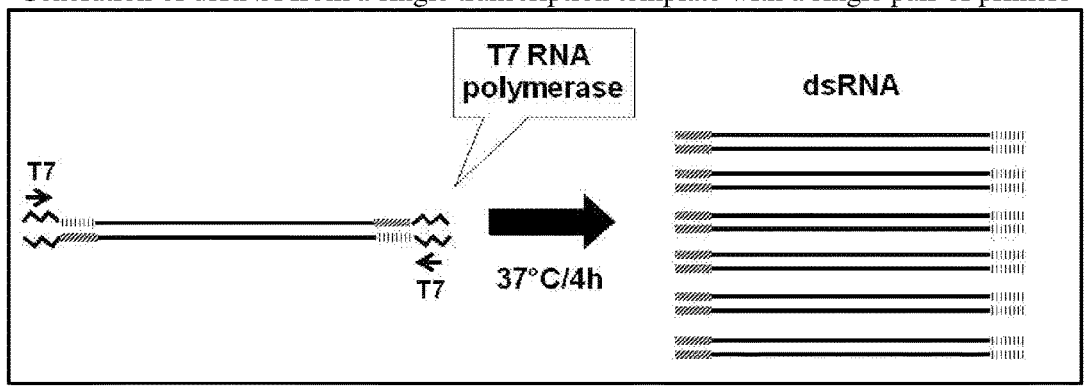
FIG. 1 includes a depiction of a strategy used to provide dsRNA from a single transcription template with a single pair of primers.

The nucleic acid sequences identified in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of a RNA strand is determined by the sequence of the DNA from which it was transcribed (but for the substitution of uracil (U) nucleobases for thymine (T)), a RNA sequence is included by any reference to the DNA sequence encoding it. In the accompanying sequence listing:

SEQ ID NO:1 shows a DNA sequence comprising rpL40-1 from *Diabrotica virgifera*.

SEQ ID NO:2 shows an amino acid sequence of a RPL40-1 protein from *Diabrotica virgifera*.

SEQ ID NO:3 shows a DNA sequence comprising rpL40-2 from *Diabrotica virgifera*.

SEQ ID NO:4 shows an amino acid sequence of a RPL40-2 protein from *Diabrotica virgifera*.

SEQ ID NO:5 shows a DNA sequence comprising rpL40-3 from *Diabrotica virgifera*.

SEQ ID NO:6 shows an amino acid sequence of a RPL40-3 protein from *Diabrotica virgifera*.

SEQ ID NO:7 shows an amino acid sequence of a hypothetical protein protein from *Diabrotica virgifera* SEQ ID NO:5.

SEQ ID NO:8 shows an amino acid sequence of a hypothetical protein protein from *Diabrotica virgifera* SEQ ID NO:5.

SEQ ID NO:9 shows a DNA sequence of rpL40-1 reg1 (region 1) from *Diabrotica virgifera* that was used for in vitro dsRNA synthesis (T7 promoter sequences at 5' and 3' ends not shown).

SEQ ID NO:10 shows a DNA sequence of rpL40-3 reg3 (region 3) from *Diabrotica virgifera* that was used for in vitro dsRNA synthesis (T7 promoter sequences at 5' and 3' ends not shown).

SEQ ID NO:11 shows a DNA reverse complement sequence of rpL40-1 v1 (version 1) from *Diabrotica virgifera* that was used for in vitro dsRNA synthesis (T7 promoter sequences at 5' and 3' ends not shown).

SEQ ID NO:12 shows a DNA sequence of rpL40-1 v2 (version 2) from *Diabrotica virgifera* that was used for in vitro dsRNA synthesis (T7 promoter sequences at 5' and 3' ends not shown).

SEQ ID NO:13 shows a DNA sequence of rpL40-1 v3 (version 3) from *Diabrotica virgifera* that was used for in vitro dsRNA synthesis (T7 promoter sequences at 5' and 3' ends not shown).

SEQ ID NO:14 shows a DNA sequence of rpL40-1 v4 (version 4) from *Diabrotica virgifera* that was used for in vitro dsRNA synthesis (T7 promoter sequences at 5' and 3' ends not shown).

SEQ ID NO:15 shows a DNA sequence of rpL40-1 v5 (version 5) from *Diabrotica virgifera* that was used for in vitro dsRNA synthesis (T7 promoter sequences at 5' and 3' ends not shown).

SEQ ID NO:16 shows a DNA sequence of a T7 phage promoter.

SEQ ID NO:17 shows a DNA sequence of a YFP coding region segment that was used for in vitro dsRNA synthesis (T7 promoter sequences at 5' and 3' ends not shown).

SEQ ID NOs:18 to 31 show primers used to amplify portions of a rpL40 subunit sequence from *Diabrotica virgifera* comprising rpL40 reg1 and rpL40 reg3.

SEQ ID NO:32 shows a YFP protein coding sequence

SEQ ID NO:33 shows a DNA sequence of Annexin region 1.

SEQ ID NO:34 shows a DNA sequence of Annexin region 2.

SEQ ID NO:35 shows a DNA sequence of Beta spectrin 2 region 1.

SEQ ID NO:36 shows a DNA sequence of Beta spectrin 2 region 2.

SEQ ID NO:37 shows a DNA sequence of mtRP-L4 region 1.

SEQ ID NO:38 shows a DNA sequence of mtRP-L4 region 2.

SEQ ID NOs:29 to 66 show primers used to amplify gene regions of YFP, Annexin, Beta spectrin 2, and mtRP-L4 for dsRNA synthesis.

SEQ ID NO:67 shows a maize DNA sequence encoding a TIP41-like protein.

SEQ ID NO:68 shows a DNA sequence of oligonucleotide T20NV.

SEQ ID NOs:69 to 73 show sequences of primers and probes used to measure maize transcript levels.

SEQ ID NO:74 shows a DNA sequence of a portion of a SpecR coding region used for binary vector backbone detection.

SEQ ID NO:75 shows a DNA sequence of a portion of an AAD1 coding region used for genomic copy number analysis.

SEQ ID NO:76 shows a DNA sequence of a maize invertase gene.

SEQ ID NOs:77 to 85 show sequences of primers and probes used for gene copy number analyses.

SEQ ID NOs:86 to 88 show sequences of primers and probes used for maize expression analysis.

SEQ ID NO:89 shows an exemplary DNA sequence of BSB rpL40 transcript from a Neotropical Brown Stink Bug (*Euschistus heros*).

SEQ ID NO:90 shows an amino acid sequence of a from *Euschistus heros* RPL40 protein.

SEQ ID NO:91 shows a DNA sequence of BSB_rpL40 reg1 (region 1) from *Euschistus heros* that was used for in vitro dsRNA synthesis (T7 promoter sequences at 5' and 3' ends not shown).

SEQ ID NO:92 shows a DNA sequence of BSB_rpL40 v1 (version 1) from *Euschistus heros* that was used for in vitro dsRNA synthesis (T7 promoter sequences at 5' and 3' ends not shown).

SEQ ID NO:93-94 show primers used to amplify portions of a from *Euschistus heros* rpL40 sequence comprising BSB_rpL40 reg1.

SEQ ID NO:95 is the sense strand of YFP-targeted dsRNA: YFPv2

SEQ ID NO:96-97 show primers used to amplify portions of a YFP-targeted dsRNA: YFPv2

SEQ ID NOs:98-110 show exemplary RNAs transcribed from nucleic acids comprising exemplary rpL40 polynucleotides and fragments thereof.

SEQ ID NO:111 shows an IDT Custom Oligo probe rpl40 PRB Set1, labeled with FAM and double quenched with Zen and Iowa Black quenchers.

SEQ ID NO:112 shows an exemplary linker polynucleotide, which forms a "loop" when transcribed in an RNA transcript to form a hairpin structure:

DETAILED DESCRIPTION

I. Overview of Several Embodiments

We developed RNA interference (RNAi) as a tool for insect pest management, using one of the most likely target pest species for transgenic plants that express dsRNA; the western corn rootworm. Thus far, most genes proposed as targets for RNAi in rootworm larvae do not actually achieve their purpose. Herein, we describe RNAi-mediated knockdown of ribosomal protein L40 (rpL40) in the exemplary insect pests, western corn rootworm and Neotropical brown stink bug, which is shown to have a lethal phenotype when, for example, iRNA molecules are delivered via ingested or injected rpL40 dsRNA. In embodiments herein, the ability to deliver rpL40 dsRNA by feeding to insects confers an RNAi effect that is very useful for insect (e.g., coleopteran and hemipteran) pest management. By combining rpL40-mediated RNAi with other useful RNAi targets (e.g., ROP (U.S. patent application Publication Ser. No. 14/577,811), RNA-PII (U.S. patent application Publication Ser. No. 14/577,854), RNA polymerase I1 RNAi targets (U.S. Patent Application No. 62/133,214), RNA polymerase II215 RNAi targets (U.S. Patent Application No. 62/133,202), RNA polymerase II33 RNAi targets (U.S. Patent Application No. 62/133,210), ncm RNAi targets (U.S. Patent Application No. 62/095,487), snap25 RNAi targets (U.S. Patent Application No. 62/193,502), transcription elongation factor spt5 RNAi targets (U.S. Patent Application No. 62/168,613), transcription elongation factor spt6 RNAi targets (U.S. Patent Application No. 62/168,606), COPI alpha (U.S. Patent Application No. 62/063,199), COPI gamma (U.S. Patent Application No. 62/063,192), COPI delta (U.S. Patent Application No. 62/063,216), COPI beta (U.S. Patent Application No. 62/063,203), sec23 (U.S. Patent Application No. 61/989,170), sec24 (U.S. Patent Application No. 62/061,608), and dre4 (U.S. Patent Application No. 61/989,843)), the potential to affect multiple target sequences, for example, in larval rootworms, may increase opportunities to develop sustainable approaches to insect pest management involving RNAi technologies.

Disclosed herein are methods and compositions for genetic control of coleopteran and/or hemipteran pest infestations. Methods for identifying one or more gene(s) essential to the lifecycle of a coleopteran and/or hemipteran pest for use as a target gene for RNAi-mediated control of a coleopteran and/or hemipteran pest population are also provided. DNA plasmid vectors encoding one or more dsRNA molecules may be designed to suppress one or more target gene(s) essential for growth, survival, development, and/or reproduction. In some embodiments, methods are provided for post-transcriptional repression of expression or inhibition of a target gene via nucleic acid molecules that are complementary to a coding or non-coding sequence of the target gene in a coleopteran and/or hemipteran pest. In these and further embodiments, a coleopteran and/or hemipteran pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, shRNA, miRNA and/or hpRNA that is complementary to coding and/or non-coding sequences of the target gene(s) to achieve at least partial control of a coleopteran and/or hemipteran pest. Disclosed is a set of isolated and purified nucleic acid molecules comprising a nucleotide sequence, for example, as set forth in any of SEQ ID NOs:1, 3, 5, 9-15, 89, 91-92, and fragments thereof. In some embodiments, a stabilized dsRNA molecule may be expressed from this sequence, fragments thereof, or a gene comprising one of these sequences, for the post-transcriptional silencing or inhibition of a target gene. In certain embodiments, isolated and purified nucleic acid molecules comprise all or part of SEQ ID NO:1. In other embodiments, isolated and purified nucleic acid molecules comprise all or part of SEQ ID NO:3. In still further embodiments, isolated and purified nucleic acid molecules comprise all or part of SEQ ID NO:5. In other embodiments, isolated and purified nucleic acid molecules comprise all or part of SEQ ID NO:9. In yet other embodiments, isolated and purified nucleic acid molecules comprise all or part of SEQ ID NOs:10-15, SEQ ID NO:89, or SEQ ID NOs:91-92.

Some embodiments involve a recombinant host cell (e.g., a plant cell) having in its genome at least one recombinant DNA sequence encoding at least one iRNA (e.g., dsRNA) molecule(s). In particular embodiments, the dsRNA molecule(s) may be produced when ingested by a coleopteran and/or hemipteran pest to post-transcriptionally silence or inhibit the expression of a target gene in the coleopteran and/or hemipteran pest. The recombinant DNA sequence may comprise, for example, one or more of any of SEQ ID NOs:1, 3, 5, 9-15, 89, or 91-92; fragments of any of SEQ ID NOs:1, 3, 5, 9-15, 89, or 91-92; or a partial sequence of a gene comprising one or more of SEQ ID NOs:1, 3, 5, 9-15, 89, or 91-92; or complements thereof.

Some embodiments involve a recombinant host cell having in its genome a recombinant DNA sequence encoding at least one iRNA (e.g., dsRNA) molecule(s) comprising all or part of SEQ ID NO:98, SEQ ID NO:99, SEQ ID NO:100, and/or SEQ ID NO:108 (e.g., at least one polynucleotide selected from a group comprising SEQ ID NOs:101-107 and 109-110), or the complement thereof. When ingested by a coleopteran and/or hemipteran pest, the iRNA molecule(s) may silence or inhibit the expression of a target gene comprising SEQ ID NOs:1, 3, 5, 9-15, 89, and/or 91-92, in the coleopteran and/or hemipteran pest, and thereby result in cessation of growth, development, reproduction, and/or feeding in the coleopteran and/or hemipteran pest.

In some embodiments, a recombinant host cell having in its genome at least one recombinant DNA sequence encoding at least one dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA sequence(s). In particular embodiments, a dsRNA molecule of the invention may be expressed in a transgenic plant cell. Therefore, in these and other embodiments, a dsRNA molecule of the invention may be isolated from a transgenic plant cell. In particular embodiments, the transgenic plant is a plant selected from the group comprising corn (*Zea mays*), soybean (*Glycine max*), and plants of the family Poaceae.

Some embodiments involve a method for modulating the expression of a target gene in a coleopteran and/or hemipteran pest cell. In these and other embodiments, a nucleic acid molecule may be provided, wherein the nucleic acid molecule comprises a nucleotide sequence encoding a dsRNA molecule. In particular embodiments, a nucleotide sequence encoding a dsRNA molecule may be operatively linked to a promoter, and may also be operatively linked to a transcription termination sequence. In particular embodiments, a method for modulating the expression of a target gene in a coleopteran and/or hemipteran pest cell may comprise: (a) transforming a plant cell with a vector comprising a nucleotide sequence encoding a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the dsRNA molecule encoded by the nucleotide sequence of the vector. A plant may be regenerated from a plant cell that has the vector integrated in its genome and comprises the dsRNA molecule encoded by the nucleotide sequence of the vector.

Thus, also disclosed is a transgenic plant comprising a vector having a nucleotide sequence encoding a dsRNA molecule integrated in its genome, wherein the transgenic plant comprises the dsRNA molecule encoded by the nucleotide sequence of the vector. In particular embodiments, expression of a dsRNA molecule in the plant is sufficient to modulate the expression of a target gene in a cell of a coleopteran and/or hemipteran pest that contacts the transformed plant or plant cell, for example, by feeding on the transformed plant, a part of the plant (e.g., root) or plant cell. Transgenic plants disclosed herein may display resistance and/or enhanced tolerance to coleopteran and/or hemipteran pest infestations. Particular transgenic plants may display resistance and/or enhanced tolerance to one or more coleopteran and/or hemipteran pests selected from the group consisting of: WCR, NCR, SCR, MCR, *D. balteata*, *D. u. tenella*, *D. speciosa*, *D. u. undecimpunctata*, *Euschistus heros*, *E. servus*, *Piezodorus guildinii*, *Halyomorpha halys*, *Nezara viridula*, *Chinavia hilare*, *C. marginatum*, *Dichelops melacanthus*, *D. furcatus*, *Edessa meditabunda*, *Thyanta perditor*, *Horcias nobilellus*, *Taedia stigmosa*, *Dysdercus peruvianus*, *Neomegalotomus parvus*, *Leptoglossus zonatus*, *Niesthrea sidae*, *Lygus hesperus*, and/or *Lygus lineolaris*.

Also disclosed herein are methods for delivery of control agents, such as an iRNA molecule, to a coleopteran and/or hemipteran pest. Such control agents may cause, directly or indirectly, impairment in the ability of the coleopteran and/or hemipteran pest to feed, grow or otherwise cause damage in a host. In some embodiments, a method is provided comprising delivery of a stabilized dsRNA molecule to a coleopteran and/or hemipteran pest to suppress at least one target gene in the coleopteran and/or hemipteran pest, thereby reducing or eliminating plant damage by a coleopteran and/or hemipteran pest. In some embodiments, a method of inhibiting expression of a target gene in a coleopteran and/or hemipteran pest may result in the cessation of growth, development, reproduction, and/or feeding in the coleopteran and/or hemipteran pest. In some embodiments, the method may eventually result in death of the coleopteran and/or hemipteran pest.

In some embodiments, compositions (e.g., a topical composition) are provided that comprise an iRNA (e.g., dsRNA) molecule of the invention for use in plants, animals, and/or the environment of a plant or animal to achieve the elimination or reduction of a coleopteran and/or hemipteran pest infestation. In particular embodiments, the composition may be a nutritional composition or food source to be fed to the coleopteran and/or hemipteran pest. Some embodiments comprise making the nutritional composition or food source available to the coleopteran and/or hemipteran pest. Ingestion of a composition comprising iRNA molecules may result in the uptake of the molecules by one or more cells of the coleopteran and/or hemipteran pest, which may in turn result in the inhibition of expression of at least one target gene in cell(s) of the coleopteran and/or hemipteran pest. Ingestion of or damage to a plant or plant cell by a coleopteran and/or hemipteran pest may be limited or eliminated in or on any host tissue or environment in which the coleopteran and/or hemipteran pest is present by providing one or more compositions comprising an iRNA molecule of the invention in the host of the coleopteran and/or hemipteran pest.

RNAi baits are formed when the dsRNA is mixed with food or an attractant or both. When the pests eat the bait, they also consume the dsRNA. Baits may take the form of granules, gels, flowable powders, liquids, or solids. In another embodiment, rab5 may be incorporated into a bait formulation such as that described in U.S. Pat. No. 8,530,440 which is hereby incorporated by reference. Generally, with baits, the baits are placed in or around the environment of the insect pest, for example, WCR can come into contact with, and/or be attracted to, the bait.

The compositions and methods disclosed herein may be used together in combinations with other methods and compositions for controlling damage by coleopteran and/or hemipteran pests. For example, an iRNA molecule as described herein for protecting plants from coleopteran and/or hemipteran pests may be used in a method comprising the additional use of one or more chemical agents effective against a coleopteran and/or hemipteran pest, biopesticides effective against a coleopteran and/or hemipteran pest, crop rotation, or recombinant genetic techniques that exhibit features different from the features of the RNAi-mediated methods and RNAi compositions of the invention (e.g., recombinant production of proteins in plants that are harmful to a coleopteran and/or hemipteran pest (e.g., Bt toxins)).

II. Abbreviations dsRNA double-stranded ribonucleic acid
GI growth inhibition
NCBI National Center for Biotechnology Information
gDNA genomic Deoxyribonucleic Acid
iRNA inhibitory ribonucleic acid
ORF open reading frame
RNAi ribonucleic acid interference
miRNA micro ribonucleic acid
shRNA small hairpin ribonucleic acid
siRNA small inhibitory ribonucleic acid
hpRNA hairpin ribonucleic acid
UTR untranslated region
WCR western corn rootworm (*Diabrotica virgifera virgifera* LeConte)
NCR northern corn rootworm (*Diabrotica barberi* Smith and Lawrence)
MCR Mexican corn rootworm (*Diabrotica virgifera zeae* Krysan and Smith)
PCR Polymerase chain reaction
RISC RNA-induced Silencing Complex
SCR southern corn rootworm (*Diabrotica undecimpunctata howardi* Barber)
BSB Neotropical brown stink bug (*Euschistus heros* Fabricius)
YFP yellow fluorescent protein
SEM standard error of the mean

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to insects of the genus *Diabrotica*, which feed upon corn and other true grasses. In particular examples, a coleopteran pest is selected from the list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella; D. speciosa* Germar; and *D. u. undecimpunctata* Mannerheim.

Hemipteran pest: As used herein, the term "hemipteran pest" refers to insects of the order Hemiptera, including, for example and without limitation, insects in the families Pentatomidae, Miridae, Pyrrhocoridae, Coreidae, Alydidae, and Rhopalidae, which feed on a wide range of host plants and have piercing and sucking mouth parts. In particular examples, a hemipteran pest is selected from the list comprising, *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Seal) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

Contact (with an organism): As used herein, the term "contact with" or "uptake by" an organism (e.g., a coleopteran and/or hemipteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize).

Encoding a dsRNA: As used herein, the term "encoding a dsRNA" includes a gene whose RNA transcription product is capable of forming an intramolecular dsRNA structure (e.g., a hairpin) or intermolecular dsRNA structure (e.g., by hybridizing to a target RNA molecule).

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern (RNA) blot, RT-PCR, western (immuno-) blot, or in vitro, in situ, or in vivo protein activity assay(s).

Genetic material: As used herein, the term "genetic material" includes all genes and nucleic acid molecules, such as DNA and RNA.

Inhibition: As used herein, the term "inhibition", when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

```
ATGATGATG    polynucleotide

TACTACTAC    "complement" of the polynucleotide

CATCATCAT    "reverse complement" of the poly-
             nucleotide
```

Some embodiments of the invention may include hairpin RNA-forming RNAi molecules. In these RNAi molecules, both the complement of a nucleic acid to be targeted by RNA interference and the reverse complement may be found in the same molecule, such that the single-stranded RNA molecule may "fold over" and hybridize to itself over region comprising the complementary and reverse complementary polynucleotides, as demonstrated in the following illustration:

```
5' AUGAUGAUG-linker polynucleotide-CAUCAUCAU 3',
``` which hybridizes to form:

```
    5' AUGAUGAUG
       |||||||||
       linker polynucleotide
    3' UACUACUAC
```

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), shRNA (small hairpin RNA), miRNA (micro-RNA), hpRNA (hairpin RNA), tRNA (transfer RNA, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "polynucleotide" and "nucleic acid" and "fragments" thereof, or more generally "segment", will be understood by those in the art as a functional term that includes both genomic sequences, ribosomal RNA sequences, transfer RNA sequences, messenger RNA sequences, operon sequences, and smaller engineered nucleotide sequences that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a "primer", which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence", "structural nucleotide sequence", or "structural nucleic acid molecule" refers to a nucleotide sequence that is ultimately translated into a polypeptide, via transcription and mRNA, when placed under the control of appropriate regulatory sequences. With respect to RNA, the term "coding polynucleotide" refers to a polynucleotide that is translated into a peptide, polypeptide, or protein. The boundaries of a coding sequence are determined by a translation start codon at the 5'-terminus and a translation stop codon at the 3'-terminus. Coding polynucleotides include, but are not limited to: genomic DNA; cDNA; EST; and recombinant nucleotide sequences.

As used herein, "transcribed non-coding polynucleotide" refers to segments of mRNA molecules such as 5'UTR, 3'UTR and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18S rRNA, 23S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "linker" in a nucleic acid and which is transcribed into an RNA molecule.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity", as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-244; Higgins and Sharp (1989) CABIOS 5:151-153; Corpet et al. (1988) Nucleic Acids Res. 16:10881-10890; Huang et al. (1992) Comp. Appl. Biosci. 8:155-165; Pearson et al. (1994) Methods Mol. Biol. 24:307-331; Tatiana et al. (1999) FEMS Microbiol. Lett. 174:247-250. A detailed consideration of sequence alignment methods and homology calculations can be found in, e.g., Altschul et al. (1990) J. Mol. Biol. 215:403-410.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an antiparallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^+$ concentration) of the hybridization will determine the stringency of hybridization. The ionic strength of the wash buffer and the wash temperature also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11, and updates; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995, and updates.

As used herein, "stringent conditions" encompass conditions under which hybridization will occur only if there is more than 80% sequence match between the hybridization molecule and a homologous sequence within the target nucleic acid molecule. "Stringent conditions" include further particular levels of stringency. Thus, as used herein, "moderate stringency" conditions are those under which molecules with more than 80% sequence match (i.e., having less than 20% mismatch) will hybridize; conditions of "high stringency" are those under which sequences with more than 90% match (i.e. having less than 10% mismatch) will hybridize; and conditions of "very high stringency" are those under which sequences with more than 95% match (i.e., having less than 5% mismatch) will hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology", with regard to a contiguous nucleic acid sequence, refers to contiguous nucleotide sequences that are borne by nucleic acid molecules that hybridize under stringent conditions to a nucleic acid molecule having the reference nucleic acid sequence. For example, nucleic acid molecules having sequences that are substantially homologous to a reference nucleic acid sequence of SEQ ID NO:1 are those nucleic acid molecules that hybridize under stringent conditions (e.g., the Moderate Stringency conditions set forth, supra) to nucleic acid molecules having the reference nucleic acid sequence of SEQ ID NO:1. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary, two protein-coding regions may be joined in the same reading frame (e.g., in a translationally fused ORF). However, nucleic acids need not be contiguous to be operably linked.

The term, "operably linked", when used in reference to a regulatory sequence and a coding sequence, means that the regulatory sequence affects the expression of the linked coding sequence. "Regulatory sequences", or "control elements", refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:10421-10425).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, Xba1/NcoI fragment 5' to the *Brassica napus* ALS3 structural gene (or a nucleotide sequence similar to said Xba1/NcoI fragment) (U.S. Pat. No. 5,659,026).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Soybean plant: As used herein, the term "soybean plant" refers to a plant of the species *Glycine*; for example, *Glycine max*.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-793); lipofection (Feigner et al. (1987) Proc. Natl. Acad. Sci. USA 84:7413-7417); microinjection (Mueller et al. (1978) Cell 15:579-585); *Agrobacterium*-mediated transfer (Fraley et al. (1983) Proc. Natl. Acad. Sci. USA 80:4803-4807); direct DNA uptake; and microprojectile bombardment (Klein et al. (1987) Nature 327:70).

Transgene: An exogenous nucleic acid sequence. In some examples, a transgene may be a sequence that encodes one or both strand(s) of a dsRNA molecule that comprises a nucleotide sequence that is complementary to a nucleic acid molecule found in a coleopteran and/or hemipteran pest. In further examples, a transgene may be an antisense nucleic acid sequence, wherein expression of the antisense nucleic acid sequence inhibits expression of a target nucleic acid sequence. In still further examples, a transgene may be a gene sequence (e.g., a herbicide-resistance gene), a gene encoding an industrially or pharmaceutically useful compound, or a gene encoding a desirable agricultural trait. In these and other examples, a transgene may contain regulatory sequences operably linked to a coding sequence of the transgene (e.g., a promoter).

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also be an RNA molecule. A vector may also include one or more genes, antisense sequences, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% to 115% or greater relative to the yield of check varieties in the same growing location containing significant densities of coleopteran and/or hemipteran pests that are injurious to that crop growing at the same time and under the same conditions.

Unless specifically indicated or implied, the terms "a", "an", and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Coleopteran and/or Hemipteran Pest Sequence A. Overview Described herein are nucleic acid molecules useful for the control of coleopteran and/or hemipteran pests. Described nucleic acid molecules include target sequences (e.g., native genes, and non-coding sequences), dsRNAs, siRNAs, hpRNAs, shRNA, and miRNAs. For example, dsRNA, siRNA, shRNA, miRNA and/or hpRNA molecules are described in some embodiments that may be specifically complementary to all or part of one or more native nucleic acid sequences in a coleopteran and/or hemipteran pest. In these and further embodiments, the native nucleic acid sequence(s) may be one or more target gene(s), the product of which may be, for example and without limitation: involved in a metabolic process; involved in a reproductive process; or involved in larval/nymph development. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in coleopteran and/or hemipteran pests, or result in reduced growth and/or reproduction.

In some embodiments, at least one target gene in a coleopteran and/or hemipteran pest may be selected, wherein the target gene comprises a nucleotide sequence comprising rpL40 (SEQ ID NOs:1, 3, 5, or 89). In particular examples, a target gene in a coleopteran and/or hemipteran pest is selected, wherein the target gene comprises a novel nucleotide sequence comprising rpL40 (SEQ ID NOs:1, 3, 5, or 89).

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of a protein product of rpL40 (SEQ ID NOs:1, 3, 5, or 89). A target gene may be any nucleic acid sequence in a coleopteran and/or hemipteran pest, the post-transcriptional inhibition of which has a deleterious effect on the coleopteran and/or hemipteran pest, or provides a protective benefit against the coleopteran and/or hemipteran pest to a plant. In particular examples, a target gene is a nucleic acid molecule comprising a nucleotide sequence that encodes a polypeptide comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of a protein product of novel nucleotide sequence SEQ ID NOs:1, 3, 5, or 89.

Provided according to the invention are nucleotide sequences, the expression of which results in an RNA molecule comprising a nucleotide sequence that is specifically complementary to all or part of a native RNA molecule that is encoded by a coding sequence in a coleopteran and/or hemipteran pest. In some embodiments, after ingestion of the expressed RNA molecule by a coleopteran and/or hemipteran pest, down-regulation of the coding sequence in cells of the coleopteran and/or hemipteran pest may be obtained. In particular embodiments, down-regulation of the coding sequence in cells of the coleopteran and/or hemipteran pest may result in a deleterious effect on the growth, viability, proliferation, and/or reproduction of the coleopteran and/or hemipteran pest.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target coleopteran and/or hemipteran pest genes. Such sequences may be derived from both mono-cistronic and poly-cistronic genes.

Thus, also described herein in connection with some embodiments are iRNA molecules (e.g., dsRNAs, siRNAs, shRNA, miRNAs and hpRNAs) that comprise at least one nucleotide sequence that is specifically complementary to all or part of a target sequence in a coleopteran and/or hemipteran pest. In some embodiments an iRNA molecule may comprise nucleotide sequence(s) that are complementary to all or part of a plurality of target sequences; for example, 2, 3, 4, 5, 6, 7, 8, 9, 10, or more target sequences. In particular embodiments, an iRNA molecule may be produced in vitro, or in vivo by a genetically-modified organism, such as a plant or bacterium. Also disclosed are cDNA sequences that may be used for the production of dsRNA molecules, siRNA molecules, shRNA molecules, miRNA molecules and/or hpRNA molecules that are specifically complementary to all or part of a target sequence in a coleopteran and/or hemipteran pest. Further described are recombinant DNA constructs for use in achieving stable transformation of particular host targets. Transformed host targets may express effective levels of dsRNA, siRNA, shRNA, miRNA and/or hpRNA molecules from the recombinant DNA constructs. Therefore, also described is a plant transformation vector comprising at least one nucleotide sequence operably linked to a heterologous promoter functional in a plant cell, wherein expression of the nucleotide sequence(s) results in an RNA molecule comprising a nucleotide sequence that is specifically complementary to all or part of a target sequence in a coleopteran and/or hemipteran pest.

In some embodiments, nucleic acid molecules useful for the control of coleopteran and/or hemipteran pests may include: all or part of a native nucleic acid sequence isolated from *Diabrotica* or a hemipteran comprising rpL40 (SEQ ID NOs:1, 3, 5, or 89); nucleotide sequences that when expressed result in an RNA molecule comprising a nucleotide sequence that is specifically complementary to all or part of a native RNA molecule that is encoded by rpL40 (SEQ ID NOs:1, 3, 5, or 89); iRNA molecules (e.g., dsRNAs, siRNAs, shRNA, miRNAs and hpRNAs) that comprise at least one nucleotide sequence that is specifically complementary to all or part of rpL40 (SEQ ID NOs:1, 3, 5, or 89); cDNA sequences that may be used for the production of dsRNA molecules, siRNA molecules, shRNA molecules, miRNA and/or hpRNA molecules that are specifically complementary to all or part of rpL40 (S SEQ ID NOs:1, 3, 5, or 89); and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, shRNA, miRNA and hpRNA) molecules that inhibit target gene expression in a cell, tissue, or organ of a coleopteran and/or hemipteran pest; and DNA molecules capable of being expressed as an iRNA molecule in a cell or microorganism to inhibit target gene expression in a cell, tissue, or organ of a coleopteran and/or hemipteran pest.

Some embodiments of the invention provide an isolated nucleic acid molecule comprising at least one (e.g., one, two, three, or more) nucleotide sequence(s) selected from the group consisting of: SEQ ID NO:1; the complement of SEQ ID NO:1; SEQ ID NO:3; the complement of SEQ ID NO:3; SEQ ID NO:5; the complement of SEQ ID NO:5; SEQ ID NO:89; the complement of SEQ ID NO:89; a fragment of at least 15 contiguous nucleotides (e.g., 15, 16, 17, 18, 19, 20, 21, 22, 23, 24, 25, 26, 27, 28, 29, 30 or more contiguous nucleotides) of any of SEQ ID NOs:1, 3, 5, and 89; the complement of a fragment of at least 15 contiguous nucleotides of any of SEQ ID NOs:1, 3, 5, and 89; a native coding sequence of a coleopteran or hemipteran organism (e.g., WCR and BSB) comprising all or part of any of SEQ ID NOs:1, 3, 5, and 89; the complement of a native coding sequence of a coleopteran or hemipteran organism comprising all or part of any of SEQ ID NOs:1, 3, 5, and 89; a native non-coding sequence of a coleopteran or hemipteran organism that is transcribed into a native RNA molecule comprising all or part of any of SEQ ID NOs:1, 3, 5, and 89; the complement of a native non-coding sequence of a coleopteran or hemipteran organism that is transcribed into a native RNA molecule comprising all or part of any of SEQ ID NOs:1, 3, 5, and 89; a fragment of at least 15 contiguous nucleotides of a native non-coding sequence of a coleopteran or hemipteran organism that is transcribed into a native RNA molecule comprising all or part of any of SEQ ID NOs:1, 3, 5, and 89; the complement of a fragment of at least 15 contiguous nucleotides of a native non-coding sequence of a coleopteran or hemipteran organism that is transcribed into a native RNA molecule comprising all or part of any of SEQ ID NOs:1, 3, 5, and 89; a fragment of at least 15 contiguous nucleotides of a native coding sequence of a coleopteran or hemipteran organism that is transcribed into a native RNA molecule comprising SEQ ID NOs:1, 3, 5, and 89; the complement of a fragment of at least 15 contiguous nucleotides of a native coding sequence of a coleopteran or hemipteran organism that is transcribed into a native RNA molecule comprising SEQ ID NOs:1, 3, 5, and 89. In particular embodiments, contact with or uptake by a coleopteran and/or hemipteran pest of the isolated nucleic acid sequence inhibits the growth, development, reproduction and/or feeding of the coleopteran and/or hemipteran pest.

In some embodiments, a nucleic acid molecule of the invention may comprise at least one (e.g., one, two, three, or more) DNA sequence(s) capable of being expressed as an iRNA molecule in a cell or microorganism to inhibit target gene expression in a cell, tissue, or organ of a coleopteran and/or hemipteran pest. Such DNA sequence(s) may be operably linked to a promoter sequence that functions in a cell comprising the DNA molecule to initiate or enhance the transcription of the encoded RNA capable of forming a dsRNA molecule(s). In one embodiment, the at least one (e.g., one, two, three, or more) DNA sequence(s) may be derived from a polynucleotide(s) selected from the group consisting of: SEQ ID NOs:1, 3, 5, and 89. Derivatives of SEQ ID NOs:1, 3, 5, or 89 include fragments of SEQ ID NOs:1, 3, 5, or 89. In some embodiments, such a fragment may comprise, for example, at least about 15 contiguous nucleotides of SEQ ID NOs:1, 3, 5, or 89, or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NOs:1, 3, 5, or 89, or a complement thereof. In these and further embodiments, such a fragment may comprise, for example, more than about 15 contiguous nucleotides of SEQ ID NOs:1, 3, 5, or 89, or a complement thereof. Thus, a fragment of SEQ ID NOs:1, 3, 5, or 89 may comprise, for example, 15, 16, 17, 18, 19, 20, 21, about 25, (e.g., 22, 23, 24, 25, 26, 27, 28, and 29), about 30, about 40, (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200 or more contiguous nucleotides of SEQ ID NOs:1, 3, 5, or 89, or a complement thereof.

Some embodiments comprise introducing partial- or fully-stabilized dsRNA molecules into a coleopteran and/or hemipteran pest to inhibit expression of a target gene in a cell, tissue, or organ of the coleopteran and/or hemipteran pest. When expressed as an iRNA molecule (e.g., dsRNA, siRNA, shRNA, miRNA, and hpRNA) and taken up by a coleopteran and/or hemipteran pest, nucleic acid sequences comprising one or more fragments of SEQ ID NOs:1, 3, 5, or 89 may cause one or more of death, growth inhibition, change in sex ratio, reduction in brood size, cessation of infection, and/or cessation of feeding by a coleopteran and/or hemipteran pest. For example, in some embodiments, a dsRNA molecule comprising a nucleotide sequence including about 15 to about 300 or about 19 to about 300 nucleotides that are substantially homologous to a coleopteran and/or hemipteran pest target gene sequence and comprising one or more fragments of a nucleotide sequence comprising SEQ ID NOs:1, 3, 5, or 89 is provided. Expression of such a dsRNA molecule may, for example, lead to mortality and/or growth inhibition in a coleopteran and/or hemipteran pest that takes up the dsRNA molecule.

In certain embodiments, dsRNA molecules provided by the invention comprise nucleotide sequences complementary to a target gene comprising SEQ ID NOs:1, 3, 5, or 89 and/or nucleotide sequences complementary to a fragment of SEQ ID NOs:1, 3, 5, or 89, the inhibition of which target gene in a coleopteran and/or hemipteran pest results in the reduction or removal of a protein or nucleotide sequence agent that is essential for the coleopteran and/or hemipteran pest's growth, development, or other biological function. A selected nucleotide sequence may exhibit from about 80% to about 100% sequence identity to SEQ ID NOs:1, 3, 5, or 89, a contiguous fragment of the nucleotide sequence set forth in SEQ ID NOs:1, 3, 5, or 89, or the complement of either of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NOs:1, 3, 5, or 89, a contiguous fragment of the nucleotide sequence set forth SEQ ID NOs:1, 3, 5, or 89, or the complement of either of the foregoing.

In some embodiments, an isolated nucleic acid molecule of the invention may comprise at least one (e.g., one, two, three, or more) polynucleotide(s) selected from the group consisting of: SEQ ID NO:98; the complement of SEQ ID NO:98; SEQ ID NO:99; the complement of SEQ ID NO:99; SEQ ID NO:100; the complement of SEQ ID NO:100; a fragment of at least 15 contiguous nucleotides of SEQ ID NOs:98-100 (e.g., SEQ ID NOs:101-107); the complement of a fragment of at least 15 contiguous nucleotides of SEQ ID NOs:98-100; a native coding polynucleotide of a *Diabrotica* organism comprising any of SEQ ID NOs:101-107; the complement of a native coding polynucleotide of a *Diabrotica* organism comprising any of SEQ ID NOs:101-107; a fragment of at least 15 contiguous nucleotides of a native coding polynucleotide of a *Diabrotica* organism comprising any of SEQ ID NOs:101-107; and the complement of a fragment of at least 15 contiguous nucleotides of a native coding polynucleotide of a *Diabrotica* organism comprising any of SEQ ID NOs:101-107.

In other embodiments, an isolated nucleic acid molecule of the invention may comprise at least one (e.g., one, two, three, or more) polynucleotide(s) selected from the group consisting of: SEQ ID NO:108; the complement of SEQ ID NO:108; a fragment of at least 15 contiguous nucleotides of SEQ ID NO:108 (e.g., SEQ ID NOs:109-110); the complement of a fragment of at least 15 contiguous nucleotides of SEQ ID NO:108; a native coding polynucleotide of a hemipteran (e.g., BSB) organism comprising any of SEQ ID NOs:109-110; the complement of a native coding polynucleotide of a hemipteran organism comprising any of SEQ ID NOs:109-110; a fragment of at least 15 contiguous nucleotides of a native coding polynucleotide of a hemipteran organism comprising any of SEQ ID NOs:109-110; and the complement of a fragment of at least 15 contiguous nucleotides of a native coding polynucleotide of a hemipteran organism comprising any of SEQ ID NOs:109-110.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target coleopteran and/or hemipteran pest species, or the DNA molecule can be constructed as a chimera from a plurality of such specifically complementary sequences.

In some embodiments, a nucleic acid molecule may comprise a first and a second nucleotide sequence separated by a "spacer sequence". A spacer sequence may be a region comprising any sequence of nucleotides that facilitates secondary structure formation between the first and second nucleotide sequences, where this is desired. In one embodiment, the spacer sequence is part of a sense or antisense coding sequence for mRNA. The spacer sequence may alternatively comprise any combination of nucleotides or homologues thereof that are capable of being linked covalently to a nucleic acid molecule.

For example, in some embodiments, the DNA molecule may comprise a nucleotide sequence coding for one or more different RNA molecules, wherein each of the different RNA molecules comprises a first nucleotide sequence and a second nucleotide sequence, wherein the first and second nucleotide sequences are complementary to each other. The first and second nucleotide sequences may be connected within an RNA molecule by a spacer sequence. The spacer sequence may constitute part of the first nucleotide sequence or the second nucleotide sequence. Expression of an RNA molecule comprising the first and second nucleotide sequences may lead to the formation of a dsRNA molecule of the present invention, by specific base-pairing of the first and second nucleotide sequences. The first nucleotide sequence or the second nucleotide sequence may be substantially identical to a nucleic acid sequence native to a coleopteran and/or hemipteran pest (e.g., a target gene, or transcribed non-coding sequence), a derivative thereof, or a complementary sequence thereto.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNAse III enzyme, such as DICER in eukaryotes, either in vitro or in vivo. See Elbashir et al. (2001) Nature 411:494-498; and Hamilton and Baulcombe (1999) Science 286(5441):950-952. DICER or functionally-equivalent RNAse III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNAse III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNAse III enzymes from heterologous nucleic acid molecules may efficiently mediate the down-regulation of target genes in coleopteran and/or hemipteran pests.

In some embodiments, a nucleic acid molecule of the invention may include at least one non-naturally occurring nucleotide sequence that can be transcribed into a single-stranded RNA molecule capable of forming a dsRNA molecule in vivo through intermolecular hybridization. Such dsRNA sequences typically self-assemble, and can be provided in the nutrition source of a coleopteran and/or hemipteran pest to achieve the post-transcriptional inhibition of a target gene. In these and further embodiments, a nucleic acid molecule of the invention may comprise two different non-naturally occurring nucleotide sequences, each of which is specifically complementary to a different target gene in a coleopteran and/or hemipteran pest. When such a nucleic acid molecule is provided as a dsRNA molecule to a coleopteran and/or hemipteran pest, the dsRNA molecule inhibits the expression of at least two different target genes in the coleopteran and/or hemipteran pest.

C. Obtaining Nucleic Acid Molecules

A variety of native sequences in coleopteran and/or hemipteran pests may be used as target sequences for the design of nucleic acid molecules of the invention, such as iRNAs and DNA molecules encoding iRNAs. Selection of native sequences is not, however, a straight-forward process. Only a small number of native sequences in the coleopteran and/or hemipteran pest will be effective targets. For example, it cannot be predicted with certainty whether a particular native sequence can be effectively down-regulated by nucleic acid molecules of the invention, or whether down-regulation of a particular native sequence will have a detrimental effect on the growth, viability, proliferation, and/or reproduction of the coleopteran and/or hemipteran pest. The vast majority of native coleopteran and/or hemipteran pest sequences, such as ESTs isolated therefrom (for example, as listed in U.S. Pat. Nos. 7,612,194 and 7,943,819), do not have a detrimental effect on the growth, viability, proliferation, and/or reproduction of the coleopteran and/or hemipteran pest, such as WCR, NCR, SCR, BSB, *Nezara viridula, Piezodorus guildinii, Halyomorpha halys, Chinavia hilare, Euschistus servus, Dichelops melacanthus, Dichelops furcatus, Edessa meditabunda, Thyanta perditor, Chinavia marginatum, Horcias nobilellus, Taedia stigmosa, Dysdercus peruvianus, Neomegalotomus parvus, Leptoglossus zonatus, Niesthrea sidae, Lygus hesperus*, and *Lygus lineolaris*.

Neither is it predictable which of the native sequences which may have a detrimental effect on a coleopteran and/or hemipteran pest are able to be used in recombinant techniques for expressing nucleic acid molecules complementary to such native sequences in a host plant and providing the detrimental effect on the coleopteran and/or hemipteran pest upon feeding without causing harm to the host plant.

In some embodiments, nucleic acid molecules of the invention (e.g., dsRNA molecules to be provided in the host plant of a coleopteran and/or hemipteran pest) are selected to target cDNA sequences that encode proteins or parts of proteins essential for coleopteran and/or hemipteran pest survival, such as amino acid sequences involved in metabolic or catabolic biochemical pathways, cell division, reproduction, energy metabolism, digestion, host plant recognition, and the like. As described herein, ingestion of compositions by a target organism containing one or more dsRNAs, at least one segment of which is specifically complementary to at least a substantially identical segment of RNA produced in the cells of the target pest organism, can result in the death or other inhibition of the target. A nucleotide sequence, either DNA or RNA, derived from a coleopteran and/or hemipteran pest can be used to construct plant cells resistant to infestation by the coleopteran and/or hemipteran pests. The host plant of the coleopteran and/or hemipteran pest (e.g., *Z. mays* or *G. max*), for example, can be transformed to contain one or more of the nucleotide sequences derived from the coleopteran and/or hemipteran pest as provided herein. The nucleotide sequence transformed into the host may encode one or more RNAs that form into a dsRNA sequence in the cells or biological fluids within the transformed host, thus making the dsRNA available if/when the coleopteran and/or hemipteran pest forms a nutritional relationship with the transgenic host. This may result in the suppression of expression of one or more genes in the cells of the coleopteran and/or hemipteran pest, and ultimately death or inhibition of its growth or development.

Thus, in some embodiments, a gene is targeted that is essentially involved in the growth, development and reproduction of a coleopteran and/or hemipteran pest. Other target genes for use in the present invention may include, for example, those that play important roles in coleopteran and/or hemipteran pest viability, movement, migration, growth, development, infectivity, establishment of feeding sites and reproduction. A target gene may therefore be a housekeeping gene or a transcription factor. Additionally, a native coleopteran and/or hemipteran pest nucleotide sequence for use in the present invention may also be derived from a homolog (e.g., an ortholog), of a plant, viral, bacterial or insect gene, the function of which is known to those of skill in the art, and the nucleotide sequence of which is specifically hybridizable with a target gene in the genome of the target coleopteran and/or hemipteran pest. Methods of identifying a homolog of a gene with a known nucleotide sequence by hybridization are known to those of skill in the art.

In some embodiments, the invention provides methods for obtaining a nucleic acid molecule comprising a nucleotide sequence for producing an iRNA (e.g., dsRNA, siRNA, shRNA, miRNA, and hpRNA) molecule. One such embodiment comprises: (a) analyzing one or more target gene(s) for their expression, function, and phenotype upon dsRNA-mediated gene suppression in a coleopteran and/or hemipteran pest; (b) probing a cDNA or gDNA library with a probe comprising all or a portion of a nucleotide sequence or a homolog thereof from a targeted coleopteran and/or hemipteran pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA sequence or a homolog thereof; and (f) chemically synthesizing all or a substantial portion of a gene sequence, or a siRNA or miRNA or shRNA or hpRNA or mRNA or dsRNA.

In further embodiments, a method for obtaining a nucleic acid fragment comprising a nucleotide sequence for producing a substantial portion of an iRNA (e.g., dsRNA, siRNA, shRNA, miRNA, and hpRNA) molecule includes: (a) synthesizing first and second oligonucleotide primers specifically complementary to a portion of a native nucleotide sequence from a targeted coleopteran and/or hemipteran pest; and (b) amplifying a cDNA or gDNA insert present in a cloning vector using the first and second oligonucleotide primers of step (a), wherein the amplified nucleic acid molecule comprises a substantial portion of a siRNA or shRNA or miRNA or hpRNA or mRNA or dsRNA molecule.

Nucleic acids of the invention can be isolated, amplified, or produced by a number of approaches. For example, an iRNA (e.g., dsRNA, siRNA, shRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P. E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,415,732, 4,458,066, 4,725,677, 4,973,679, and 4,980,460. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present invention may be produced chemically or enzymatically by one skilled in the art through manual or automated reactions, or in vivo in a cell comprising a nucleic acid molecule comprising a sequence encoding the RNA, dsRNA, siRNA, miRNA, shRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., U.S. Pat. Nos. 5,593,874, 5,693,512, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a coleopteran and/or hemipteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a nucleotide sequence that, upon expression to RNA and ingestion by a coleopteran and/or hemipteran pest, achieves suppression of a target gene in a cell, tissue, or organ of the coleopteran and/or hemipteran pest. Thus, some embodiments provide a recombinant nucleic acid molecule comprising a nucleic acid sequence capable of being expressed as an iRNA (e.g., dsRNA, siRNA, miRNA, shRNA, and hpRNA) molecule in a plant cell to inhibit target gene expression in a coleopteran and/or hemipteran pest. In order to initiate or enhance expression, such recombinant nucleic acid molecules may comprise one or more regulatory sequences, which regulatory sequences may be operably linked to the nucleic acid sequence capable of being expressed as an iRNA. Methods to express a gene suppression molecule in plants are known, and may be used to express a nucleotide sequence of the present invention. See, e.g., International PCT Publication No. WO06/073727; and U.S. Patent Publication No. 2006/0200878 A1).

In specific embodiments, a recombinant DNA molecule of the invention may comprise a nucleic acid sequence encoding a dsRNA molecule. Such recombinant DNA molecules may encode dsRNA molecules capable of inhibiting the expression of endogenous target gene(s) in a coleopteran and/or hemipteran pest cell upon ingestion. In many embodiments, a transcribed RNA may form a dsRNA molecule that may be provided in a stabilized form; e.g., as a hairpin and stem and loop structure.

In these and further embodiments, one strand of a dsRNA molecule may be formed by transcription from a nucleotide sequence which is substantially homologous to a nucleotide sequence consisting of SEQ ID NO:1; the complement of SEQ ID NO:1; SEQ ID NO:3, the complement of SEQ ID NO:3; SEQ ID NO:5; the complement of SEQ ID NO:5; a fragment of at least 19 contiguous nucleotides of SEQ ID NOs:1, 3, or 5; the complement of a fragment of at least 19 contiguous nucleotides of SEQ ID NOs:1, 3, or 5; a native coding sequence of a *Diabrotica* organism (e.g., WCR) comprising SEQ ID NOs:1, 3, or 5; the complement of a native coding sequence of a *Diabrotica* organism comprising SEQ ID NOs:1, 3, or 5; a native non-coding sequence of a *Diabrotica* organism that is transcribed into a native RNA molecule comprising SEQ ID NOs:1, 3, or 5; the complement of a native non-coding sequence of a *Diabrotica* organism that is transcribed into a native RNA molecule comprising SEQ ID NOs:1, 3, or 5; a fragment of at least 19 contiguous nucleotides of a native coding sequence of a *Diabrotica* organism (e.g., WCR) comprising SEQ ID NOs: 1, 3, or 5; the complement of a fragment of at least 19 contiguous nucleotides of a native coding sequence of a *Diabrotica* organism comprising SEQ ID NOs:1, 3, or 5; a fragment of at least 19 contiguous nucleotides of a native non-coding sequence of a *Diabrotica* organism that is transcribed into a native RNA molecule comprising SEQ ID NOs:1, 3, or 5; and the complement of a fragment of at least 19 contiguous nucleotides of a native non-coding sequence of a *Diabrotica* organism that is transcribed into a native RNA molecule comprising SEQ ID NOs:1, 3, or 5.

In other embodiments, one strand of a dsRNA molecule may be formed by transcription from a nucleotide sequence which is substantially homologous to a nucleotide sequence consisting of SEQ ID NO:89; the complement of SEQ ID NO:89; a fragment of at least 15 contiguous nucleotides of SEQ ID NO:89; the complement of a fragment of at least 15 contiguous nucleotides of SEQ ID NO:89; a native coding sequence of a hemipteran organism comprising SEQ ID NO:89; the complement of a native coding sequence of a hemipteran organism comprising SEQ ID NO:89; a native non-coding sequence of a hemipteran organism that is transcribed into a native RNA molecule comprising SEQ ID NO:89; the complement of a native non-coding sequence of a hemipteran organism that is transcribed into a native RNA molecule comprising SEQ ID NO:89; a fragment of at least 15 contiguous nucleotides of a native coding sequence of a hemipteran organism comprising SEQ ID NO:89; the complement of a fragment of at least 15 contiguous nucleotides of a native coding sequence of a hemipteran organism comprising SEQ ID NO:89; a fragment of at least 15 contiguous nucleotides of a native non-coding sequence of a hemipteran organism that is transcribed into a native RNA molecule comprising SEQ ID NO:89; and the complement of a fragment of at least 15 contiguous nucleotides of a native non-coding sequence of a hemipteran organism that is transcribed into a native RNA molecule comprising SEQ ID NO:89.

In particular embodiments, a recombinant DNA molecule encoding a dsRNA molecule may comprise at least two nucleotide sequence segments within a transcribed sequence, such sequences arranged such that the transcribed sequence comprises a first nucleotide sequence segment in a sense orientation, and a second nucleotide sequence segment (comprising the complement of the first nucleotide sequence segment) is in an antisense orientation, relative to at least one promoter, wherein the sense nucleotide sequence segment and the antisense nucleotide sequence segment are linked or connected by a spacer sequence segment of from about five (~5) to about one thousand (~1000) nucleotides. The spacer sequence segment may form a loop between the sense and antisense sequence segments. The sense nucleotide sequence segment or the antisense nucleotide sequence segment may be substantially homologous to the nucleotide sequence of a target gene (e.g., a gene comprising SEQ ID NOs:1, 3, 5, or 89) or fragment thereof. In some embodiments, however, a recombinant DNA molecule may encode a dsRNA molecule without a spacer sequence. In embodiments, a sense coding sequence and an antisense coding sequence may be different lengths.

Sequences identified as having a deleterious effect on coleopteran and/or hemipteran pests or a plant-protective effect with regard to coleopteran and/or hemipteran pests may be readily incorporated into expressed dsRNA molecules through the creation of appropriate expression cassettes in a recombinant nucleic acid molecule of the invention. For example, such sequences may be expressed as a hairpin with stem and loop structure by taking a first segment corresponding to a target gene sequence (e.g., SEQ ID NOs:1, 3, 5, 89, and fragments thereof); linking this sequence to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms and comprises the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native coleopteran and/or hemipteran pest sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Embodiments of the invention include introduction of a recombinant nucleic acid molecule of the present invention into a plant (i.e., transformation) to achieve coleopteran and/or hemipteran pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acid sequences of the invention can, for example, be suitably inserted into a vector under the control of a suitable promoter that functions in one or more hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart coleopteran and/or hemipteran pest resistance to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a nucleotide sequence that is substantially homologous and specifically hybridizable to a corresponding transcribed nucleotide sequence within a coleopteran and/or hemipteran pest that may cause damage to the host plant species. The coleopteran and/or hemipteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within coleopteran and/or hemipteran pests that infest the transgenic host plant. In some embodiments, suppression of expression of the target gene in the target coleopteran and/or hemipteran pest may result in the plant being resistant to attack by the pest.

In order to enable delivery of iRNA molecules to a coleopteran and/or hemipteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a nucleotide sequence of the invention operably linked to one or more regulatory sequences, such as a heterologous promoter sequence that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-5749) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-324); the CaMV 35S promoter (Odell et al. (1985) Nature 313:810-

812; the figwort mosaic virus 35S-promoter (Walker et al. (1987) Proc. Natl. Acad. Sci. USA 84(19):6624-6628); the sucrose synthase promoter (Yang and Russell (1990) Proc. Natl. Acad. Sci. USA 87:4144-4148); the R gene complex promoter (Chandler et al. (1989) Plant Cell 1:1175-1183); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 5,378,619 and 6,051,753); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-573; Bevan et al. (1983) Nature 304:184-187).

In particular embodiments, nucleic acid molecules of the invention comprise a tissue-specific promoter, such as a root-specific promoter. Root-specific promoters drive expression of operably-linked coding sequences exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a nucleotide sequence or fragment for coleopteran and/or hemipteran pest control according to the invention may be cloned between two root-specific promoters oriented in opposite transcriptional directions relative to the nucleotide sequence or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a coleopteran and/or hemipteran pest so that suppression of target gene expression is achieved.

Additional regulatory sequences that may optionally be operably linked to a nucleic acid molecule of interest include 5'UTRs that function as a translation leader sequence located between a promoter sequence and a coding sequence. The translation leader sequence is present in the fully-processed mRNA, and it may affect processing of the primary transcript, and/or RNA stability. Examples of translation leader sequences include maize and *petunia* heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAntl; TEV (Carrington and Freed (1990) J. Virol. 64:1590-7); and AGRtunos (GenBank™ Accession No. V00087; and Bevan et al. (1983) Nature 304:184-7).

Additional regulatory sequences that may optionally be operably linked to a nucleic acid molecule of interest also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory sequences operatively linked to one or more nucleotide sequences of the present invention. When expressed, the one or more nucleotide sequences result in one or more RNA molecule(s) comprising a nucleotide sequence that is specifically complementary to all or part of a native RNA molecule in a coleopteran and/or hemipteran pest. Thus, the nucleotide sequence(s) may comprise a segment encoding all or part of a ribonucleotide sequence present within a targeted coleopteran and/or hemipteran pest RNA transcript, and may comprise inverted repeats of all or a part of a targeted coleopteran and/or hemipteran pest transcript. A plant transformation vector may contain sequences specifically complementary to more than one target sequence, thus allowing production of more than one dsRNA for inhibiting expression of two or more genes in cells of one or more populations or species of target coleopteran and/or hemipteran pests. Segments of nucleotide sequence specifically complementary to nucleotide sequences present in different genes can be combined into a single composite nucleic acid molecule for expression in a transgenic plant. Such segments may be contiguous or separated by a spacer sequence.

In some embodiments, a plasmid of the present invention already containing at least one nucleotide sequence(s) of the invention can be modified by the sequential insertion of additional nucleotide sequence(s) in the same plasmid, wherein the additional nucleotide sequence(s) are operably linked to the same regulatory elements as the original at least one nucleotide sequence(s). In some embodiments, a nucleic acid molecule may be designed for the inhibition of multiple target genes. In some embodiments, the multiple genes to be inhibited can be obtained from the same coleopteran and/or hemipteran pest species, which may enhance the effectiveness of the nucleic acid molecule. In other embodiments, the genes can be derived from different coleopteran and/or hemipteran pests, which may broaden the range of coleopteran and/or hemipteran pests against which the agent(s) is/are effective. When multiple genes are targeted for suppression or a combination of expression and suppression, a polycistronic DNA element can be fabricated.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide tolerance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase (ALS) gene which confers imidazolinone or sulfonylurea tolerance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18th Stadler Genetics Symposium, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to coleopteran and/or hemipteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by Agrobacterium-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580, 5,550,318, 5,538,880, 6,160,208, 6,399,861, and 6,403,865), etc. Techniques that are particularly useful for transforming corn are described, for example, in U.S. Pat. Nos. 5,591,616, 7,060,876 and 7,939,3281. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences encoding one or more iRNA molecules in the genome of the transgenic plant.

The most widely utilized method for introducing an expression vector into plants is based on the natural transformation system of various Agrobacterium species. A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border sequences. The T-region may also contain a selectable marker for efficient recovery of transgenic cells and plants, and a multiple cloning site for inserting sequences for transfer such as a dsRNA encoding nucleic acid.

Thus, in some embodiments, a plant transformation vector is derived from a Ti plasmid of A. tumefaciens (See, e.g., U.S. Pat. Nos. 4,536,475, 4,693,977, 4,886,937, and 5,501,967; and European Patent No. EP 0 122 791) or a Ri plasmid of A. rhizogenes. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as Sinorhizobium, Rhizobium, and Mesorhizobium that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., typically about 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA sequence encoding one or more iRNA molecules that inhibit target gene expression in a coleopteran and/or hemipteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or immuno blots) or by enzymatic function;

plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event". Such transgenic plants are hemizygous for the inserted exogenous sequence. In some embodiments, a transgenic plant homozygous with respect to a transgene may be obtained by sexually mating (selfing) an independent segregant transgenic plant that contains a single exogenous gene sequence to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules that have a coleopteran and/or hemipteran pest-inhibitory effect are produced in a plant cell. The iRNA molecules (e.g., dsRNA molecules) may be expressed from multiple nucleic acid sequences introduced in different transformation events, or from a single nucleic acid sequence introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple nucleic acid sequences that are each homologous to different loci within one or more coleopteran and/or hemipteran pests (for example, the locus defined by SEQ ID NOs:1, 3, 5, or 89), both in different populations of the same species of coleopteran and/or hemipteran pest, or in different species of coleopteran and/or hemipteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence that encodes an iRNA molecule may be introduced into a first plant line that is amenable to transformation to produce a transgenic plant, which transgenic plant may be crossed with a second plant line to introgress the nucleotide sequence that encodes the iRNA molecule into the second plant line.

The invention also includes commodity products containing one or more of the sequences of the present invention. Particular embodiments include commodity products produced from a recombinant plant or seed containing one or more of the nucleotide sequences of the present invention. A commodity product containing one or more of the sequences of the present invention is intended to include, but not be limited to, meals, oils, crushed or whole grains or seeds of a plant, or any food or animal feed product comprising any meal, oil, or crushed or whole grain of a recombinant plant or seed containing one or more of the sequences of the present invention. The detection of one or more of the sequences of the present invention in one or more commodity or commodity products contemplated herein is de facto evidence that the commodity or commodity product is produced from a transgenic plant designed to express one or more of the nucleotides sequences of the present invention for the purpose of controlling coleopteran and/or hemipteran plant pests using dsRNA-mediated gene suppression methods.

In some aspects, seeds and commodity products produced by transgenic plants derived from transformed plant cells are included, wherein the seeds or commodity products comprise a detectable amount of a nucleic acid sequence of the invention. In some embodiments, such commodity products may be produced, for example, by obtaining transgenic plants and preparing food or feed from them. Commodity products comprising one or more of the nucleic acid sequences of the invention includes, for example and without limitation: meals, oils, crushed or whole grains or seeds of a plant, and any food product comprising any meal, oil, or crushed or whole grain of a recombinant plant or seed comprising one or more of the nucleic acid sequences of the invention. The detection of one or more of the sequences of the invention in one or more commodity or commodity products is de facto evidence that the commodity or commodity product is produced from a transgenic plant designed to express one or more of the iRNA molecules of the invention for the purpose of controlling coleopteran and/or hemipteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran and/or hemipteran pest other than the one defined by SEQ ID NOs:1, 3, 5, or 89, such as, for example, one or more loci selected from the group consisting of Caf1-180 (U.S. Patent Application Publication No. 2012/0174258), VatpaseC (U.S. Patent Application Publication No. 2012/0174259), Rho1 (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), ROP (U.S. patent application Publication Ser. No. 14/577,811), RNA polymerase II (U.S. Patent Application Publication No. 62/133,214), RNA polymerase II140 (U.S. patent application Publication Ser. No. 14/577,854), RNA polymerase II215 (U.S. Patent Application Publication No. 62/133,202), RNA polymerase II33 (U.S. Patent Application Publication No. 62/133,210), ncm (U.S. Patent Application No. 62/095,487), Dre4 (U.S. patent application Ser. No. 14/705,807), COPI alpha (U.S. Patent Application No. 62/063,199), COPI beta (U.S. Patent Application No. 62/063,203), COPI gamma (U.S. Patent Application No. 62/063,192), COPI delta (U.S. Patent Application No. 62/063,216); a transgenic event from which is transcribed an iRNA molecule targeting a gene in an organism other than a coleopteran and/or hemipteran pest (e.g., a plant-parasitic nematode); a gene encoding an insecticidal protein (e.g., a *Bacillus thuringiensis* insecticidal protein, such as, for example, Cry34Ab1 (U.S. Pat. Nos. 6,127,180, 6,340,593, and 6,624,145), Cry35Ab1 (U.S. Pat. Nos. 6,083,499, 6,340, 593, and 6,548,291), a "Cry34/35Ab1" combination in a single event (e.g., maize event DAS-59122-7; U.S. Pat. No. 7,323,556), Cry3A (e.g., U.S. Pat. No. 7,230,167), Cry3B (e.g., U.S. Pat. No. 8,101,826), Cry6A (e.g., U.S. Pat. No. 6,831,062), and combinations thereof (e.g., U.S. Patent Application Nos. 2013/0167268, 2013/0167269, and 2013/0180016); *Alcaligenes* spp. (e.g., U.S. Patent Application Publication No. 2014/0033361) or *Pseudomonas* spp. (e.g., PCT Application Publication No. WO2015038734) insecticidal protein); a herbicide tolerance gene (e.g., a gene providing tolerance to glyphosate, glufosinate, dicamba or 2,4-D (e.g., U.S. Pat. No. 7,838,733)); and a gene contributing to a desirable phenotype in the transgenic plant, such as increased yield, altered fatty acid metabolism, or restoration of cytoplasmic male sterility. In particular embodiments, sequences encoding iRNA molecules of the invention may be combined with other insect control or with disease resistance traits in a plant to achieve desired traits for enhanced control of insect damage and plant disease. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Coleopteran and/or Hemipteran Pest

A. Overview

In some embodiments of the invention, at least one nucleic acid molecule useful for the control of coleopteran and/or hemipteran pests may be provided to a coleopteran and/or hemipteran pest, wherein the nucleic acid molecule leads to RNAi-mediated gene silencing in the coleopteran and/or hemipteran pest. In particular embodiments, an iRNA molecule (e.g., dsRNA, siRNA, miRNA, shRNA, and hpRNA) may be provided to the coleopteran and/or hemipteran pest. In some embodiments, a nucleic acid molecule useful for the control of coleopteran and/or hemipteran pests may be provided to a coleopteran and/or hemipteran pest by contacting the nucleic acid molecule with the coleopteran and/or hemipteran pest. In these and further embodiments, a nucleic acid molecule useful for the control of coleopteran and/or hemipteran pests may be provided in a feeding substrate of the coleopteran and/or hemipteran pest, for example, a nutritional composition. In these and further embodiments, a nucleic acid molecule useful for the control of coleopteran and/or hemipteran pests may be provided through ingestion of plant material comprising the nucleic acid molecule that is ingested by the coleopteran and/or hemipteran pest. In certain embodiments, the nucleic acid molecule is present in plant material through expression of a recombinant nucleic acid sequence introduced into the plant material, for example, by transformation of a plant cell with a vector comprising the recombinant nucleic acid sequence and regeneration of a plant material or whole plant from the transformed plant cell.

B. RNAi-Mediated Target Gene Suppression

In embodiments, the invention provides iRNA molecules (e.g., dsRNA, siRNA, miRNA, shRNA, and hpRNA) that may be designed to target essential native nucleotide sequences (e.g., essential genes) in the transcriptome of a coleopteran and/or hemipteran pest (e.g., WCR, NCR, MCR, BSB, *Nezara viridula, Piezodorus guildinii, Halyomorpha halys, Acrosternum hilare*, and *Euschistus servus*), for example by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the invention may be used in methods for gene suppression in a coleopteran and/or hemipteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand". The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable than are single-stranded RNA molecules, during preparation and during the step of providing the iRNA molecule to a cell, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a coleopteran and/or hemipteran pest. In certain embodiments, the in vitro transcribed iRNA molecule may be a stabilized dsRNA molecule that comprises a stem-loop structure. After a coleopteran and/or hemipteran pest contacts the in vitro transcribed iRNA molecule, post-transcriptional inhibition of a target gene in the coleopteran and/or hemipteran pest (for example, an essential gene) may occur.

In some embodiments of the invention, expression of a nucleic acid molecule comprising at least 15 contiguous nucleotides of a nucleotide sequence is used in a method for post-transcriptional inhibition of a target gene in a coleopteran pest, wherein the nucleotide sequence is selected from the group consisting of: SEQ ID NO:1; the complement of SEQ ID NO:1; SEQ ID NO:3; the complement of SEQ ID NO:3; SEQ ID NO:5; the complement of SEQ ID NO:5; a fragment of at least 15 contiguous nucleotides of SEQ ID NOs:1, 3, or 5; the complement of a fragment of at least 15 contiguous nucleotides of SEQ ID NOs:1, 3, or 5; a native coding sequence of a *Diabrotica* organism (e.g., WCR) comprising SEQ ID NOs:1, 3, or 5; the complement of a native coding sequence of a *Diabrotica* organism comprising SEQ ID NOs:1, 3, or 5; a native non-coding sequence of a *Diabrotica* organism that is transcribed into a native RNA molecule comprising SEQ ID NOs:1, 3, or 5; the complement of a native non-coding sequence of a *Diabrotica* organism that is transcribed into a native RNA molecule comprising SEQ ID NOs:1, 3, or 5; the complement of a native non-coding sequence of a *Diabrotica* organism that is transcribed into a native RNA molecule comprising SEQ ID NOs:1, 3, or 5; a fragment of at least 15 contiguous nucleotides of a native coding sequence of a *Diabrotica* organism (e.g., WCR) comprising SEQ ID NOs:1, 3, or 5; the complement of a fragment of at least 15 contiguous nucleotides of a native coding sequence of a *Diabrotica* organism comprising SEQ ID NOs:1, 3, or 5; a fragment of at least 15 contiguous nucleotides of a native non-coding sequence of a *Diabrotica* organism that is transcribed into a native RNA molecule comprising SEQ ID NOs:1, 3, or 5; and the complement of a fragment of at least 15 contiguous nucleotides of a native non-coding sequence of a *Diabrotica* organism that is transcribed into a native RNA molecule comprising SEQ ID NOs:1, 3, or 5. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

In certain embodiments of the invention, expression of a nucleic acid molecule comprising at least 15 contiguous nucleotides of a nucleotide sequence is used in a method for post-transcriptional inhibition of a target gene in a hemipteran pest, wherein the nucleotide sequence is selected from the group consisting of: SEQ ID NO:89; the complement of SEQ ID NO:89; a fragment of at least 15 contiguous nucleotides of SEQ ID NO:89; the complement of a fragment of at least 15 contiguous nucleotides of SEQ ID NO:89; a native coding sequence of a hemipteran organism SEQ ID NO:89; the complement of a native coding sequence of a hemipteran organism comprising SEQ ID NO:89; a native non-coding sequence of a hemipteran organism that is transcribed into a native RNA molecule comprising SEQ ID NO:89; the complement of a native non-coding sequence of a hemipteran organism that is transcribed into a native RNA molecule comprising SEQ ID NO:89; the complement of a native non-coding sequence of a hemipteran organism that is transcribed into a native RNA molecule comprising SEQ ID NO:89; a fragment of at least 15 contiguous nucleotides of a native coding sequence of a hemipteran organism comprising SEQ ID NO:89; the complement of a fragment of at least 15 contiguous nucleotides of a native coding sequence of a hemipteran organism comprising SEQ ID NO:89; a fragment of at least 15 contiguous nucleotides of a native non-coding sequence of a hemipteran organism that is transcribed into a native RNA molecule comprising SEQ ID NO:89; and the complement of a fragment of at least 15 contiguous nucleotides of a native non-coding sequence of a hemipteran organism that is transcribed into a native RNA molecule comprising SEQ ID NO:89. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a hemipteran pest.

In some embodiments, expression of at least one nucleic acid molecule comprising at least 15 contiguous nucleotides of a nucleotide sequence may be used in a method for post-transcriptional inhibition of a target gene in a coleopteran pest, wherein the nucleotide sequence is selected from the group consisting of: SEQ ID NO:1; the complement of SEQ ID NO:1; SEQ ID NO:3; the complement of SEQ ID NO:3; SEQ ID NO:5; the completment of SEQ ID NO:5; a fragment of at least 15 contiguous nucleotides of SEQ ID NOs:1, 3, or 5; the complement of a fragment of at least 15 contiguous nucleotides of SEQ ID NOs:1, 3, or 5; a native coding sequence of a *Diabrotica* organism (e.g., WCR) comprising SEQ ID NOs:1, 3, or 5; the complement of a native coding sequence of a *Diabrotica* organism (e.g., WCR) comprising SEQ ID NOs:1, 3, or 5; a native non-coding sequence of a *Diabrotica* organism that is transcribed into a native RNA molecule comprising SEQ ID NOs:1, 3, or 5; the complement of a native non-coding sequence of a *Diabrotica* organism that is transcribed into a native RNA molecule comprising SEQ ID NOs:1, 3, or 5; a fragment of at least 15 contiguous nucleotides of a native coding sequence of a *Diabrotica* organism (e.g., WCR) comprising SEQ ID NOs:1, 3, or 5; the complement of a fragment of at least 15 contiguous nucleotides of a native coding sequence of a *Diabrotica* organism comprising SEQ ID NOs:1, 3, or 5; a fragment of at least 15 contiguous nucleotides of a native non-coding sequence of a *Diabrotica* organism that is transcribed into a native RNA molecule comprising SEQ ID NOs:1, 3, or 5; and the complement of a fragment of at least 15 contiguous nucleotides of a native non-coding sequence of a *Diabrotica* organism that is transcribed into a native RNA molecule comprising SEQ ID NOs:1, 3, or 5. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest. In particular examples, such a nucleic acid molecule may comprise a nucleotide sequence comprising SEQ ID NOs:1, 3, or 5.

In particular embodiments of the invention, expression of a nucleic acid molecule comprising at least 15 contiguous nucleotides of a nucleotide sequence is used in a method for post-transcriptional inhibition of a target gene in a hemipteran pest, wherein the nucleotide sequence is selected from the group consisting of: SEQ ID NO:89; the complement of SEQ ID NO:89; a fragment of at least 15 contiguous nucleotides of SEQ ID NO:89; the complement of a fragment of at least 15 contiguous nucleotides of SEQ ID NO:89; a native coding sequence of a hemipteran organism SEQ ID NO:89; the complement of a native coding sequence of a hemipteran organism comprising SEQ ID NO:89; a native non-coding sequence of a hemipteran organism that is transcribed into a native RNA molecule comprising SEQ ID NO:89; the complement of a native non-coding sequence of a hemipteran organism that is transcribed into a native RNA molecule comprising SEQ ID NO:89; the complement of a native non-coding sequence of a hemipteran organism that is transcribed into a native RNA molecule comprising SEQ ID NO:89; a fragment of at least 15 contiguous nucleotides of a native coding sequence of a hemipteran organism comprising SEQ ID NO:89; the complement of a fragment of at least 15 contiguous nucleotides of a native coding sequence of a hemipteran organism comprising SEQ ID NO:89; a fragment of at least 15 contiguous nucleotides of a native non-coding sequence of a hemipteran organism that is transcribed into a native RNA molecule comprising SEQ ID NO:89; and the complement of a fragment of at least 15 contiguous nucleotides of a native non-coding sequence of a hemipteran organism that is transcribed into a native RNA molecule comprising SEQ ID NO:89. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a hemipteran pest. In particular examples, such a nucleic acid molecule may comprise a nucleotide sequence comprising SEQ ID NO:89.

It is an important feature of some embodiments of the invention that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., nucleotide sequences substantially homologous to the iRNA molecule(s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 15, 16, 17, 18, 19, 20, 21, 22, 23, 24, 25, 26, 27, 28, 29, 30, 35, 40, 45, 25, 50, 100, 200, 300, 400, 500, or at least about 1000 bases. In some embodiments, a sequence of greater than 15 to 100 nucleotides may be used. In particular embodiments, a sequence of greater than about 200 to 300 nucleotides may be used. In particular embodiments, a sequence of greater than about 500 to 1000 nucleotides may be used, depending on the size of the target gene.

In certain embodiments, expression of a target gene in a coleopteran and/or hemipteran pest may be inhibited by at least 10%; at least 33%; at least 50%; or at least 80% within a cell of the coleopteran and/or hemipteran pest, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although in certain embodiments of the invention inhibition occurs in substantially all cells of the coleopteran and/or hemipteran pest, in other embodiments inhibition occurs only in a subset of cells expressing the target gene.

In some embodiments, transcriptional suppression in a cell is mediated by the presence of a dsRNA molecule exhibiting substantial sequence identity to a promoter DNA sequence or the complement thereof, to effect what is referred to as "promoter trans suppression". Gene suppression may be effective against target genes in a coleopteran and/or hemipteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary sequences in the cells of the coleopteran and/or hemipteran pest. Post-transcriptional gene suppression by antisense or sense oriented RNA to regulate gene expression in plant cells is disclosed in U.S. Pat. Nos. 5,107,065, 5,231,020, 5,283,184, and 5,759,829.

C. Expression of iRNA Molecules Provided to a Coleopteran and/or Hemipteran Pest Expression of iRNA molecules for RNAi-mediated gene inhibition in a coleopteran and/or hemipteran pest may be carried out in any one of many in vitro or in vivo formats. The iRNA molecules may then be provided to a coleopteran and/or hemipteran pest, for example, by contacting the iRNA molecules with the pest, or by causing the pest to ingest or otherwise internalize the iRNA molecules. Some embodiments of the invention include transformed host plants of a coleopteran and/or hemipteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a coleopteran and/or hemipteran pest during feeding, the pest may ingest iRNA molecules expressed in the transgenic plants or cells. The nucleotide sequences of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a coleopteran and/or hemipteran pest comprises providing in the tissue of the host of the pest a gene-suppressive amount of at least one dsRNA molecule formed following transcription of a nucleotide sequence as described herein, at least one segment of which is complementary to an mRNA sequence within the cells of the coleopteran and/or hemipteran pest. A dsRNA molecule, including its modified form such as an siRNA, miRNA, shRNA, or hpRNA molecule, ingested by a coleopteran and/or hemipteran pest in accordance with the invention, may be at least from about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or 100% identical to an RNA molecule transcribed from a nucleic acid molecule comprising a nucleotide sequence comprising SEQ ID NOs:1, 3, 5, or 89. Isolated and substantially purified nucleic acid molecules including, but not limited to, non-naturally occurring nucleotide sequences and recombinant DNA constructs for providing dsRNA molecules of the present invention are therefore provided, which suppress or inhibit the expression of an endogenous coding sequence or a target coding sequence in the coleopteran and/or hemipteran pest when introduced thereto.

Particular embodiments provide a delivery system for the delivery of iRNA molecules for the post-transcriptional inhibition of one or more target gene(s) in a coleopteran and/or hemipteran plant pest and control of a population of the coleopteran and/or hemipteran plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the invention (e.g., a stabilized dsRNA molecule); to transform a plant cell or plant; and to generate the transgenic plant cell or the transgenic plant that contains the transcribed iRNA molecule.

To impart coleopteran and/or hemipteran pest resistance to a transgenic plant, a recombinant DNA molecule may, for example, be transcribed into an iRNA molecule, such as a dsRNA molecule, a siRNA molecule, a miRNA molecule, a shRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a coleopteran and/or hemipteran pest of a type that may infest the host plant. Expression of a target gene within the coleopteran and/or hemipteran pest is suppressed by the ingested dsRNA molecule, and the suppression of expression of the target gene in the coleopteran and/or hemipteran pest results in, for example, cessation of feeding by the coleopteran and/or hemipteran pest, with an ultimate result being, for example, that the transgenic plant is protected from further damage by the coleopteran and/or hemipteran pest. The modulatory effects of dsRNA molecules have been shown to be applicable to a variety of genes expressed in pests, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn plant) caused by a coleopteran and/or hemipteran pest that feeds on the plant, wherein the method comprises providing in the host plant a transformed plant cell expressing at least one nucleic acid molecule of the invention, wherein the nucleic acid molecule(s) functions upon being taken up by the coleopteran and/or hemipteran pest to inhibit the expression of a target sequence within the coleopteran and/or hemipteran pest, which inhibition of expression results in mortality, reduced growth, and/or reduced reproduction of the coleopteran and/or hemipteran pest, thereby reducing the damage to the host plant caused by the coleopteran and/or hemipteran pest. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a coleopteran and/or hemipteran pest cell. In some embodiments, the nucleic acid molecule(s) consist of one nucleotide sequence that is specifically hybridizable to a nucleic acid molecule expressed in a coleopteran and/or hemipteran pest cell.

In other embodiments, a method for increasing the yield of a corn crop is provided, wherein the method comprises introducing into a corn plant at least one nucleic acid molecule of the invention; cultivating the corn plant to allow the expression of an iRNA molecule comprising the nucleic acid sequence, wherein expression of an iRNA molecule comprising the nucleic acid sequence inhibits coleopteran and/or hemipteran pest growth and/or coleopteran and/or hemipteran pest damage, thereby reducing or eliminating a loss of yield due to coleopteran and/or hemipteran pest infestation. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran and/or hemipteran pest cell. In some embodiments, the nucleic acid molecule(s) consists of one nucleotide sequence that is specifically hybridizable to a nucleic acid molecule expressed in a coleopteran and/or hemipteran pest cell.

In some embodiments, a method for modulating the expression of a target gene in a coleopteran and/or hemipteran pest is provided, the method comprising: transforming a plant cell with a vector comprising a nucleic acid sequence encoding at least one nucleic acid molecule of the invention, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the coleopteran and/or hemipteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran and/or hemipteran pest cell. In some embodiments, the nucleic acid molecule(s) consists of one nucleotide sequence that is specifically hybridizable to a nucleic acid molecule expressed in a coleopteran and/or hemipteran pest cell.

iRNA molecules of the invention can be incorporated within the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to coleopteran and/or hemipteran pests. For example, the iRNA molecules of the invention may be directly introduced into the cells of a coleopteran and/or hemipteran pest. Methods for introduction may include direct mixing of iRNA with plant tissue from a host for the coleopteran and/or hemipteran pest, as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the coleopteran and/or hemipteran pests known to infest the plant. iRNA molecules produced by chemical or enzymatic synthesis may also be formulated in a manner consistent with common agricultural practices, and used as spray-on products for controlling plant damage by a coleopteran and/or hemipteran pest. The formulations may include the appropriate stickers and wetters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from coleopteran and/or hemipteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1

Insect Diet Bioassays

Sample Preparation and Bioassays

A number of dsRNA molecules (including those corresponding to rpL40-1 reg1 (SEQ ID NO:9), rpL40-3 reg3 (SEQ ID NO:10), rpL40-1 ver1 (SEQ ID NO:11), rpL40-1 ver2 (SEQ ID NO:12), rpL40-1 ver3 (SEQ ID NO:13), rpL40-1 ver4 (SEQ ID NO:14), and rpL40-1 ver5 (SEQ ID NO:15), were synthesized and purified using a MEGASCRIPT® RNAi kit or HiScribe® T7 In Vitro Transcription Kit. The purified dsRNA molecules were prepared in TE buffer, and all bioassays contained a control treatment consisting of this buffer, which served as a background check for mortality or growth inhibition of WCR (*Diabrotica virgifera virgifera* LeConte). The concentrations of dsRNA molecules in the bioassay buffer were measured using a NANODROP™ 8000 spectrophotometer (THERMO SCIENTIFIC, Wilmington, Del.).

Samples were tested for insect activity in bioassays conducted with neonate insect larvae on artificial insect diet. WCR eggs were obtained from CROP CHARACTERISTICS, INC. (Farmington, Minn.).

The bioassays were conducted in 128-well plastic trays specifically designed for insect bioassays (C-D INTERNATIONAL, Pitman, N.J.). Each well contained approximately 1.0 mL of an artificial diet designed for growth of coleopteran insects. A 60 µL aliquot of dsRNA sample was delivered by pipette onto the surface of the diet of each well (40 µL/cm$^2$). dsRNA sample concentrations were calculated as the amount of dsRNA per square centimeter (ng/cm$^2$) of surface area (1.5 cm$^2$) in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light: Dark)) for 9 days, after which time the total number of insects exposed to each sample, the number of dead insects, and the weight of surviving insects were recorded. Average percent mortality and average growth inhibition were calculated for each treatment. Growth inhibition (GI) was calculated as follows:

$$GI=[1-(TWIT/TNIT)/(TWIBC/TNIBC)]$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

Statistical analysis was done using JMP™ software (SAS, Cary, N.C.).

$LC_{50}$ (Lethal Concentration) is defined as the dosage at which 50% of the test insects are killed. $GI_{50}$ (Growth Inhibition) is defined as the dosage at which the mean growth (e.g. live weight) of the test insects is 50% of the mean value seen in Background Check samples.

Replicated bioassays demonstrated that ingestion of particular samples resulted in a surprising and unexpected mortality and growth inhibition of corn rootworm larvae.

Example 2

Identification of Candidate Target Genes

Multiple stages of WCR (*Diabrotica virgifera virgifera* LeConte) development were selected for pooled transcriptome analysis to provide candidate target gene sequences for control by RNAi transgenic plant insect resistance technology.

In one exemplification, total RNA was isolated from about 0.9 gm whole first-instar WCR larvae; (4 to 5 days post-hatch; held at 16° C.), and purified using the following phenol/TRI REAGENT®-based method (MOLECULAR RESEARCH CENTER, Cincinnati, Ohio):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 μL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 gm of larvae yielded over 1 mg of total RNA, with an $A_{260}/A_{280}$ ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA; 1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1×TAE was used as the running buffer. Before use, the electrophoresis tank and the well-forming comb were cleaned with RNAseAway™ (INVITROGEN INC., Carlsbad, Calif.). Two μL of RNA sample were mixed with 8 μL of TE buffer (10 mM Tris HCl pH 7.0; 1 mM EDTA) and 104 of RNA sample buffer (NOVAGEN® Catalog No 70606; EMD4 Bioscience, Gibbstown, N.J.). The sample was heated at 70° C. for 3 min, cooled to room temperature, and 5 μL (containing 1 μg to 2 μg RNA) were loaded per well. Commercially available RNA molecular weight markers were simultaneously run in separate wells for molecular size comparison. The gel was run at 60 volts for 2 hr.

A normalized cDNA library was prepared from the larval total RNA by a commercial service provider (EUROFINS MWG Operon, Huntsville, Ala.), using random priming. The normalized larval cDNA library was sequenced at ½ plate scale by GS FLX 454 Titanium™ series chemistry at EUROFINS MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for RNAi targeting were selected using information regarding lethal RNAi effects of particular genes in other insects such as *Drosophila* and *Tribolium*. These genes were hypothesized to be essential for survival and growth in coleopteran insects. Selected target gene homologs were identified in the transcriptome sequence database as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit to the non-*Diabrotica* candidate gene sequence present in the *Diabrotica* sequences. In most cases, *Tribolium* candidate genes which were annotated as encoding a protein gave an unambiguous sequence homology to a sequence or sequences in the *Diabrotica* transcriptome sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, Sequencher™ v4.9 (GENE CODES CORPORATION, Ann Arbor, Mich.) was used to assemble the sequences into longer contigs.

A candidate target gene encoding *Diabrotica* rpL40 (SEQ ID NOs:1, 3, and 5) was identified as a gene that may lead to coleopteran pest mortality, inhibition of growth, inhibition of development, or inhibition of reproduction in WCR.

The sequence of SEQ ID NOs:1, 3, and 5 are novel. The sequence is not provided in public databases and is not disclosed in WO/2011/025860; U.S. Patent Application No. 20070124836; U.S. Patent Application No. 20090306189; U.S. Patent Application No. US20070050860; U.S. Patent Application No. 20100192265; or U.S. Pat. No. 7,612,194. The *Diabrotica* rpL40-1 sequence (SEQ ID NO:1) is somewhat related to a fragment of a sequence from *Aedes aegypti* (GENBANK Accession No. AF418984.1). The closest homolog of the *Diabrotica* RPL40-1 amino acid sequence (SEQ ID NO:2) is a *Drosophila melanogaster* protein having GENBANK Accession No. NP 476776.1 (100% similar; 100% identical over the homology region). The *Diabrotica* rpL40-2 sequence (SEQ ID NO:3) is somewhat related to a fragment of a sequence from *Dendroctonus ponderosae* (GENBANK Accession No. APGK01027402.1). The closest homolog of the *Diabrotica* RPL40-2 amino acid sequence (SEQ ID NO:4) is a *Saccoglossus kowalevskii* protein having GENBANK Accession No. XP_006817704.1 (99% similar; 98% identical over the homology region). The *Diabrotica* rpL40-3 sequence (SEQ ID NO:5) is somewhat related to a short fragment of a sequence from *Phyllostachys edulis* (GENBANK Accession No. FP093773.1). The closest homolog of the *Diabrotica* RPL40-3 amino acid sequence (SEQ ID NO:6) is a *Gregarina niphandrodes* protein having GENBANK Accession No. XP_011128524.1 (96% similar; 88% identical over the homology region). The closest homolog of the *Diabrotica* RPL40-3 amino acid sequence (SEQ ID NO:7) is a *Gregarina niphandrodes* protein having GENBANK Accession No. XP_011128522.1 (51% similar; 35% identical over the homology region). The closest homolog of the *Diabrotica* RPL40-3 amino acid sequence (SEQ ID NO:8) is a *Gregarina niphandrodes* protein having GENBANK Accession No. XDR24359.1 (62% similar; 44% identical over the homology region).

rpL40 dsRNA transgenes can be combined with other dsRNA molecules to provide redundant RNAi targeting and synergistic RNAi effects. Transgenic corn events expressing dsRNA that targets rpL40 are useful for preventing root feeding damage by corn rootworm. rpL40 dsRNA transgenes represent new modes of action for combining with *Bacillus thuringiensis, Alcaligenes* spp., or *Pseudomonas* spp. insecticidal protein technology in Insect Resistance Management gene pyramids to mitigate against the development of rootworm populations resistant to either of these rootworm control technologies.

Full-length or partial clones of sequences of a *Diabrotica* candidate gene, herein referred to as rpL40, were used to generate PCR amplicons for dsRNA synthesis.

SEQ ID NO:1 shows a 574 bp DNA sequence of *Diabrotica* rpL40-1.

SEQ ID NO:3 shows a 652 bp DNA sequence of *Diabrotica* rpL40-2.

SEQ ID NO:5 shows a 4065 bp DNA sequence of *Diabrotica* rpL40-3.

SEQ ID NO:9 shows a 306 bp DNA sequence of rpL40-1 reg1.

SEQ ID NO:10 shows a 361 bp DNA sequence of rpL40-3 reg3.

SEQ ID NO:11 shows a 117 bp DNA sequence of rpL40-1 v1.

SEQ ID NO:12 shows a 143 bp DNA sequence of rpL40-1 v2.

SEQ ID NO:13 shows a 141 bp DNA sequence of rpL40-1 v3.

SEQ ID NO:14 shows a 130 bp DNA sequence of rpL40-1 v4.

SEQ ID NO:15 shows a 165 bp DNA sequence of rpL40-1 v5.

Example 3

Amplification of Target Genes to Produce dsRNA

Primers were designed to amplify portions of coding regions of each target gene by PCR. See Table 1. Where appropriate, a T7 phage promoter sequence (TTAATAC-GACTCACTATAGGGAGA; SEQ ID NO:16) was incorporated into the 5' ends of the amplified sense or antisense strands. See Table 1. Total RNA was extracted from WCR, and first-strand cDNA was used as template for PCR reactions using opposing primers positioned to amplify all or part of the native target gene sequence. dsRNA was also amplified from a DNA clone comprising the coding region for a yellow fluorescent protein (YFP) (SEQ ID NO:17; Shagin et al. (2004) Mol. Biol. Evol. 21(5):841-50).

TABLE 1

Primers and Primer Pairs used to amplify portions of coding regions of exemplary rpL40 target gene and YFP negative control gene.

| | Gene ID | Primer ID | SEQ ID NO: | Sequence |
|---|---|---|---|---|
| Pair 1 | rpL40-1 reg1 | rpL40-1_F | 18 | TTAATACGACTCACTATAGGGAGA GAAAATGTCAAGGCGAAAATCCA AG |
| | | rpL40-1_R | 19 | TTAATACGACTCACTATAGGGAGA CTTCTTTGGGCGCAAATTGTTG |
| Pair 2 | rpL40-3 reg 1 | rpL40-3_F | 20 | TTAATACGACTCACTATAGGGAGA GTCGAGAAGGTCAAGGACTCG |
| | | rpL40-3_R | 21 | TTAATACGACTCACTATAGGGAGA AGCTTCACCATCGCGCCGAGGTTC TTC |
| Pair 3 | rpL40-1 v1 | rpL40-1_v1_F | 22 | TTAATACGACTCACTATAGGGAGA CCACCAGATCAGCAACGTCTAATT TTTG |
| | | rpL40-1_v1_R | 23 | TTAATACGACTCACTATAGGGAGA ACCACGTAGACGTAACACCAAATG |

TABLE 1-continued

Primers and Primer Pairs used to amplify portions of coding regions of exemplary rpL40 target gene and YFP negative control gene.

| | Gene ID | Primer ID | SEQ ID NO: | Sequence |
|---|---|---|---|---|
| Pair 4 | rpL40-1 v2 | rpL40-1_v2_F | 24 | TTAATACGACTCACTATAGGGAGA TCGAACCATCATTGCGTATTTTGG |
| | | rpL40-1_v2_R | 25 | TTAATACGACTCACTATGGGAGA CTTCTTTGGGCGCAAATTGTTGGT G |
| Pair 5 | rpL40-1 v3 | rpL40-1_v3_F | 26 | TTAATACGACTCACTATAGGGAGA CAAGAGAGGCAAAAAACCAACG |
| | | rpL40-1_v3_R | 27 | TTAATACGACTCACTATAGGGAGA CTGGTGGAATACCCTCTTTGTC |
| Pair 6 | rpL40-1 v4 | rpL40-1_v4_F | 28 | TTAATACGACTCACTATAGGGAGA GCCGTAAGTGCTATGCTCGTTTG |
| | | rpL40-1_v4_R | 29 | TTAATACGACTCACTATAGGGAGA CCAGACATACAGCACAAAAATAC |
| Pair 7 | rpL40-1 v5 | rpL40-1_v5_F | 30 | TTAATACGACTCACTATAGGGAGA CAGCAACGTCTAATTTTTGCTG |
| | | rpL40-1_v5_R | 31 | TTAATACGACTCACTATAGGGAGA CATTTTGTCGCAATTGTATTTTG |
| Pair 8 | YFP | YFP-F_T7 | 32 | TTAATACGACTCACTATAGGGAGA CACCATGGGCTCCAGCGGCGCCC |
| | | YFP-F_T7 | 33 | TTAATACGACTCACTATAGGGAGA AGATCTTGAAGGCGCTCTTCAGG |

Example 4

RNAi Constructs

Template preparation by PCR and dsRNA synthesis.

A strategy used to provide specific templates for rpL40 and YFP dsRNA production is shown in FIG. 1. Template DNAs intended for use in rpL40 dsRNA synthesis were prepared by PCR using the primer pairs in Table 1 and (as PCR template) first-strand cDNA prepared from total RNA isolated from WCR first-instar larvae. For each selected rpL40 and YFP target gene region, PCR amplifications introduced a T7 promoter sequence at the 5' ends of the amplified sense and antisense strands (the YFP segment was amplified from a DNA clone of the YFP coding region). The PCR products having a T7 promoter sequence at their 5' ends of both sense and antisense strands were used as transcription template for dsRNA production. See FIG. 1. The sequences of the dsRNA templates amplified with the particular primer pairs were: SEQ ID NO:9 (rpL40-1 reg1), SEQ ID NO:10 (rpL40-3 reg3), SEQ ID NO:11 (rpL40-1 v1), SEQ ID NO:12 (rpL40-1 v2), SEQ ID NO:13 (rpL40-1 v3), SEQ ID NO:14 (rpL40-1 v4), SEQ ID NO:15 (rpL40-1 v5), and YFP (SEQ ID NO:17). Double-stranded RNA for insect bioassay was synthesized and purified using an AMBION® MEGASCRIPT® RNAi kit following the manufacturer's instructions (INVITROGEN) or HiScribe™ T7 High Yield RNA Synthesis Kit following the manufacturer's instructions (New England Biolabs). The concentrations of dsRNAs were measured using a NANODROP™ 8000 spectrophotometer (THERMO SCIENTIFIC, Wilmington, Del.).

Construction of Plant Transformation Vectors

Entry vectors harboring a target gene construct for hairpin formation comprising segments of rpL40 (SEQ ID NOs:1, 3, or 5) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a segment of a rpL40 target gene sequence in opposite orientation to one another, the two segments being separated by a linker polynucleotide (e.g., a loop (such as SEQ ID NO:112) or an ST-LS1 intron; Vancanneyt et al. (1990) Mol. Gen. Genet. 220(2):245-50). Thus, the primary mRNA transcript contains the two rpL40 gene segment sequences as large inverted repeats of one another, separated by the linker sequence. A copy of a promoter (e.g. maize ubiquitin 1, U.S. Pat. No. 5,510,474; 35S from Cauliflower Mosaic Virus (CaMV); Sugarcane bacilliform badnavirus (ScBV) promoter; promoters from rice actin genes; ubiquitin promoters; pEMU; MAS; maize H3 histone promoter; ALS promoter; phaseolin gene promoter; cab; rubisco; LAT52; Zm13; and/ or apg) is used to drive production of the primary mRNA hairpin transcript, and a fragment comprising a 3' untranslated region (e.g., a maize peroxidase 5 gene (ZmPer5 3'UTR v2; U.S. Pat. No. 6,699,984), AtUbi10, AtEf1, or StPinII) is used to terminate transcription of the hairpin-RNA-expressing gene.

A binary destination vector comprises an herbicide tolerance gene (aryloxyalknoate dioxygenase; AAD-1 v3) (U.S. Pat. No. 7,838,733(B2), and Wright et al. (2010) Proc. Natl. Acad. Sci. U.S.A. 107:20240-5) under the regulation of a plant operable promoter (e.g., sugarcane bacilliform badnavirus (ScBV) promoter (Schenk et al. (1999) Plant Mol. Biol. 39:1221-30) or ZmUbi1 (U.S. Pat. No. 5,510,474)). A 5'UTR and linker are positioned between the 3' end of the promoter segment and the start codon of the AAD-1 coding region. A fragment comprising a 3' untranslated region from a maize lipase gene (ZmLip 3'UTR; U.S. Pat. No. 7,179, 902) is used to terminate transcription of the AAD-1 mRNA.

A negative control binary vector, which comprises a gene that expresses a YFP protein, is constructed by means of standard GATEWAY® recombination reactions with a typical binary destination vector and entry vector. The binary destination vector comprises a herbicide tolerance gene (aryloxyalknoate dioxygenase; AAD-1 v3) (as above) under the expression regulation of a maize ubiquitin 1 promoter (as above) and a fragment comprising a 3' untranslated region from a maize lipase gene (ZmLip 3'UTR; as above). An entry vector comprises a YFP coding region under the expression control of a maize ubiquitin 1 promoter (as above) and a fragment comprising a 3' untranslated region from a maize peroxidase 5 gene (as above).

Example 5

Screening of Candidate Target Genes

Synthetic dsRNA designed to inhibit target gene sequences identified in EXAMPLE 2 caused mortality and growth inhibition when administered to WCR in diet-based assays. rpL40 reg1, rpL40 v2, rpL40 v3, and rpL40 v4, were observed to exhibit greatly increased efficacy in this assay over other dsRNAs screened.

Replicated bioassays demonstrated that ingestion of dsRNA preparations derived from rpL40 reg1, rpL40 v1, rpL40 v2, rpL40 v3, rpL40 v4, and rpL40 v5 each resulted in mortality and/or growth inhibition of western corn rootworm larvae. Table 2 and Table 3 show the results of diet-based feeding bioassays of WCR larvae following 9-day exposure to these dsRNAs, as well as the results obtained with a negative control sample of dsRNA prepared from a yellow fluorescent protein (YFP) coding region (SEQ ID NO:17).

TABLE 2

Results of rpL40 dsRNA diet feeding assays obtained with western corn rootworm larvae after 9 days of feeding. ANOVA analysis found significance differences in Mean % Mortality and Mean % Growth Inhibition (GI). Means were separated using the Tukey-Kramer test.

| Gene Name | Dose (ng/cm$^2$) | No. Rows | Mean % Mortality ± SEM* | Mean GI ± SEM |
|---|---|---|---|---|
| rpL40-1 reg1 | 500 | 12 | 91.60 ± 1.97 (CD) | 0.98 ± 0.01 (A) |
| rpL40-1 v1 | 500 | 18 | 11.83 ± 2.32 (DEF) | 0.44 ± 0.04 (B) |
| rpL40-1 v2 | 500 | 4 | 34.56 ± 6.62 (B) | 0.58 ± 0.10 (B) |
| rpL40-1 v3 | 500 | 2 | 36.40 ± 1.11 (B) | 0.63 ± 0.14 (AB) |
| rpL40-1 v4 | 500 | 2 | 61.77 ± 14.70 (BC) | 0.84 ± 0.10 (AB) |
| rpL40-1 v5 | 500 | 4 | 65.20 ± 2.45 (CDE) | 0.62 ± 0.10 (B) |
| TE** | 0 | 36 | 18.13 ± 1.99 (EF) | 0.08 ± 0.03 (C) |
| WATER | 500 | 28 | 13.84 ± 2.04 (EF) | −0.14 ± 0.04 (C) |
| YFP*** | 0 | 28 | 14.26 ± 1.72 (F) | 0.05 ± 0.04 (D) |

*SEM = Standard Error of the Mean. Letters in parentheses designate statistical levels. Levels not connected by same letter are significantly different (P < 0.05).
**TE = Tris HCl (1 mM) plus EDTA (1 mM) buffer, pH 7.2.
***YFP = Yellow Fluorescent Protein

TABLE 3

Summary of oral potency of rpL40 dsRNA on WCR larvae (ng/cm$^2$).

| Gene Name | LC$_{50}$ (ng/cm$^2$) | Range | GI$_{50}$ (ng/cm$^2$) | Range |
|---|---|---|---|---|
| rpL40-1 reg1 | 12.91 | 9.88-16.71 | 4.06 | 3.28-5.02 |

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,612,194, which discloses 9,112 sequences. However, it was determined that many genes suggested to have utility for RNAi-mediated insect control are not efficacious in controlling *Diabrotica*. It was also determined that sequences rpL40 reg1, rpL40 v1, rpL40 v2, rpL40 v3, rpL40 v4, and rpL40 v5 each provide surprising and unexpected superior control of *Diabrotica*, compared to other genes suggested to have utility for RNAi-mediated insect control.

For example, Annexin, Beta spectrin 2, and mtRP-L4 were each suggested in U.S. Pat. No. 7,612,194 to be efficacious in RNAi-mediated insect control. SEQ ID NO:33 is the DNA sequence of Annexin region 1 (Reg 1), and SEQ ID NO:34 is the DNA sequence of Annexin region 2 (Reg 2). SEQ ID NO:35 is the DNA sequence of Beta spectrin 2 region 1 (Reg 1), and SEQ ID NO:36 is the DNA sequence of Beta spectrin 2 region 2 (Reg2). SEQ ID NO:37 is the DNA sequence of mtRP-L4 region 1 (Reg 1), and SEQ ID NO:38 is the DNA sequence of mtRP-L4 region 2 (Reg 2). A YFP sequence (SEQ ID NO:17) was also used to produce dsRNA as a negative control.

Figure 2:
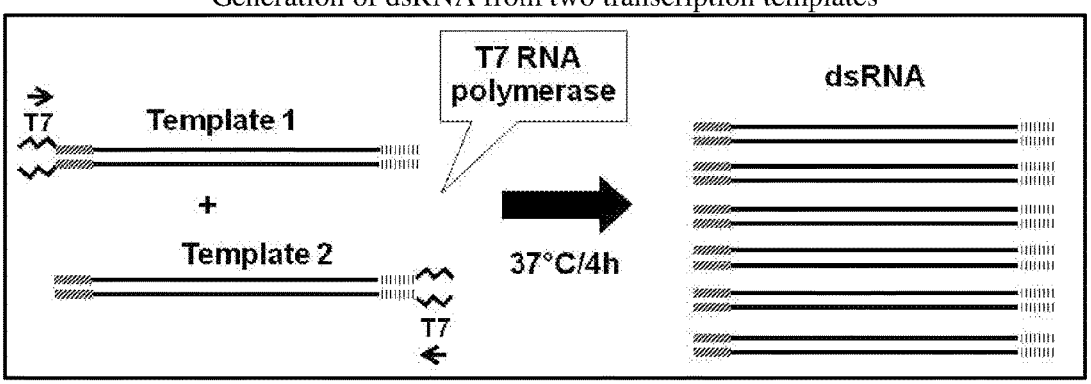
FIG. 2 includes a depiction of a strategy used to provide dsRNA from two transcription templates.

Each of the aforementioned sequences was used to produce dsRNA by the methods of EXAMPLE 3. The strategy used to provide specific templates for dsRNA production is shown in FIG. 2. Template DNAs intended for use in dsRNA synthesis were prepared by PCR using the primer pairs in Table 4 and (as PCR template) first-strand cDNA prepared from total RNA isolated from WCR first-instar larvae. (YFP was amplified from a DNA clone.) For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. See FIG. 2. Double-stranded RNA was synthesized and purified using an AMBION® MEGAscript® RNAi kit following the manufacturer's instructions (INVITROGEN). The concentrations of dsRNAs were measured using a NANODROP™ 8000 spectrophotometer (THERMO SCIENTIFIC, Wilmington, Del.). and the dsRNAs were each tested by the same diet-based bioassay methods described above. Table 4 lists the sequences of the primers used to produce the YFP, Annexin Reg1, Annexin Reg2, Beta spectrin 2 Reg1, Beta spectrin 2 Reg2, mtRP-L4 Reg1, and mtRP-L4 Reg2 dsRNA molecules. YFP primer sequences for use in the method depicted in FIG. 2 are also listed in Table 4. Table 5 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, water, or YFP protein.

TABLE 4

Primers and Primer Pairs used to amplify portions of coding regions of genes.

| | Gene ID | Primer ID | SEQ ID NO: | Sequence |
|---|---|---|---|---|
| Pair 9 | YFP | YFP-F_T7 | 39 | TTAATACGACTCACTATAGGGAGAACCATGGGCTCCAGCGGCGCCC |
| | YFP | YFP-R | 40 | AGATCTTGAAGGCGCTCTTCAGG |
| Pair 10 | YFP | YFP-F | 41 | CACCATGGGCTCCAGCGGCGCCC |
| | YFP | YFP-R_T7 | 42 | TTAATACGACTCACTATAGGGAGAGATCTTGAAGGCGCTCTTCAGG |
| Pair 11 | Annexin (Reg 1) | Ann-F1_T7 | 43 | TTAATACGACTCACTATAGGGAGACTCCAACAGTGGTTCCTTATC |
| | Annexin (Reg 1) | Ann-R1 | 44 | CTAATAATTCTTTTTTAATGTTCCTGAGG |
| Pair 12 | Annexin (Reg 1) | Ann-F1 | 45 | GCTCCAACAGTGGTTCCTTATC |
| | Annexin (Reg 1) | Ann-R1_T7 | 46 | TTAATACGACTCACTATAGGGAGACTAATAATTCTTTTTTAATGTTCCTGAGG |
| Pair 13 | Annexin (Reg 2) | Ann-F2_T7 | 47 | TTAATACGACTCACTATAGGGAGATTGTTACAAGCTGGAGAACTTCTC |
| | Annexin (Reg 2) | Ann-R2 | 48 | CTTAACCAACAACGGCTAATAAGG |
| Pair 14 | Annexin (Reg 2) | Ann-F2 | 49 | TTGTTACAAGCTGGAGAACTTCTC |
| | Annexin (Reg 2) | Ann-R2T7 | 50 | TTAATACGACTCACTATAGGGAGACTTAACCAACAACGGCTAATAAGG |
| Pair 15 | Beta-spect2 (Reg 1) | Bestasp2-F1_T7 | 51 | TTAATACGACTCACTATAGGGAGAAGATGTTGGCTGCATCTAGAGAA |
| | Beta-spect2 (Reg 1) | Bestasp2-R1 | 52 | GTCCATTCGTCCATCCACTGCA |
| Pair 16 | Beta-spect2 (Reg 1) | Bestasp2-F1 | 53 | AGATGTTGGCTGCATCTAGAGAA |
| | Beta-spect2 (Reg 1) | Bestasp2-R1_T7 | 54 | TTAATACGACTCACTATAGGGAGAGTCCATTCGTCCATCCACTGCA |
| Pair 17 | Beta-spect2 (Reg 2) | Bestasp2-F2_T7 | 55 | TTAATACGACTCACTATAGGGAGAG |
| | Beta-spect2 (Reg 2) | Bestasp2-R2 | 56 | CTGGGCAGCTTCTTGTTTCCTC |
| Pair 18 | Beta-spect2 (Reg 2) | Bestasp2-F2 | 57 | GCAGATGAACACCAGCGAGAAA |
| | Beta-spect2 (Reg 2) | Bestasp2-R2_T7 | 58 | TTAATACGACTCACTATAGGGAGACTGGGCAGCTTCTTGTTTCCTC |
| Pair 19 | mtRP-L4 (Reg 1) | L4-F1_T7 | 59 | TTAATACGACTCACTATAGGGAGAAGTGAAATGTTAGCAAATATAACATCC |
| | mtRP-L4 (Reg 1) | L4-R1 | 60 | ACCTCTCACTTCAAATCTTGACTTTG |
| Pair 20 | mtRP-L4 (Reg 1) | L4-F1 | 61 | AGTGAAATGTTAGCAAATATAACATCC |
| | mtRP-L4 (Reg 1) | L4-R1_T7 | 62 | TTAATACGACTCACTATAGGGAGAACCTCTCACTTCAAATCTTGACTTTG |
| Pair 21 | mtRP-L4 (Reg 2) | L4-F2_T7 | 63 | TTAATACGACTCACTATAGGGAGACAAAGTCAAGATTTGAAGTGAGAGGT |
| | mtRP-L4 (Reg 2) | L4-R2 | 64 | CTACAAATAAAACAAGAAGGACCCC |
| Pair 22 | mtRP-L4 (Reg 2) | L4-F2 | 65 | CAAAGTCAAGATTTGAAGTGAGAGGT |
| | mtRP-L4 (Reg 2) | L4-R2_T7 | 66 | TTAATACGACTCACTATAGGGAGACTACAAATAAAACAAGAAGGACCCC |

TABLE 5

Results of diet feeding assays obtained with western corn rootworm larvae after 9 days.

| Gene Name | Dose (ng/cm$^2$) | Mean Live Larval Weight (mg) | Mean % Mortality | Mean Growth Inhibition |
|---|---|---|---|---|
| Annexin-Reg 1 | 1000 | 0.545 | 0 | −0.262 |
| Annexin-Reg 2 | 1000 | 0.565 | 0 | −0.301 |
| Beta spectrin2 Reg 1 | 1000 | 0.340 | 12 | −0.014 |
| Beta spectrin2 Reg 2 | 1000 | 0.465 | 18 | −0.367 |
| mtRP-L4 Reg 1 | 1000 | 0.305 | 4 | −0.168 |
| mtRP-L4 Reg 2 | 1000 | 0.305 | 7 | −0.180 |
| TE buffer* | 0 | 0.430 | 13 | 0.000 |
| Water | 0 | 0.535 | 12 | 0.000 |
| YFP** | 1000 | 0.480 | 9 | −0.386 |

*TE = Tris HCl (10 mM) plus EDTA (1 mM) buffer, pH 8.
**YFP = Yellow Fluorescent Protein Example 6

Production of Transgenic Maize Tissues Comprising Insecticidal dsRNAs

*Agrobacterium*-Mediated Transformation.

Transgenic maize cells, tissues, and plants that produce one or more insecticidal dsRNA molecules (for example, at least one dsRNA molecule including a dsRNA molecule targeting a gene comprising rpL40-1 (SEQ ID NO:1); rpL40-2 (SEQ ID NO:3); rpL40-3 (SEQ ID NO:5); rpL40-1 reg1 (SEQ ID NO:9); rpL40-3 reg3 (SEQ ID NO:10); rpL40-1 v1 (SEQ ID NO:11); rpL40-1 v2 (SEQ ID NO:12); rpL40-1 v3 (SEQ ID NO:13); rpL40-1 v4 (SEQ ID NO:14); rpL40-1 v5 (SEQ ID NO:15); BSB_rpL40 (SEQ ID NO:89); BSB_rpL40 reg1 (SEQ ID NO:91); or BSB_rpL40 v1 (SEQ ID NO:92) through expression of a chimeric gene stably-integrated into the plant genome were produced following *Agrobacterium*-mediated transformation. Maize transformation methods employing superbinary or binary transformation vectors are known in the art, as described, for example, in U.S. Pat. No. 8,304,604, which is herein incorporated by reference in its entirety. Transformed tissues were selected by their ability to grow on Haloxyfop-containing medium and are screened for dsRNA production, as appropriate. Portions of such transformed tissue cultures may be presented to neonate corn rootworm larvae for bioassay, essentially as described in EXAMPLE 1.

*Agrobacterium* Culture Initiation.

Glycerol stocks of *Agrobacterium* strain DAt13192 cells (WO 2012/016222A2) harboring a binary transformation vector described above (EXAMPLE 4) were streaked on AB minimal medium plates (Watson, et al., (1975) J. Bacteriol. 123:255-264) containing appropriate antibiotics and were grown at 20° C. for 3 days. The cultures were then streaked onto YEP plates (gm/L: yeast extract, 10; Peptone, 10; NaCl 5) containing the same antibiotics and were incubated at 20° C. for 1 day.

*Agrobacterium* Culture.

On the day of an experiment, a stock solution of Inoculation Medium and acetosyringone was prepared in a volume appropriate to the number of constructs in the experiment and pipetted into a sterile, disposable, 250 mL flask. Inoculation Medium (Frame et al. (2011) *Genetic Transformation Using Maize Immature Zygotic Embryos*. IN Plant Embryo Culture Methods and Protocols: Methods in Molecular Biology. T. A. Thorpe and E. C. Yeung, (Eds), Springer Science and Business Media, LLC. pp 327-341) contained: 2.2 gm/L MS salts; 1×ISU Modified MS Vitamins (Frame et al., ibid.) 68.4 gm/L sucrose; 36 gm/L glucose; 115 mg/L L-proline; and 100 mg/L myo-inositol; at pH 5.4.) Acetosyringone was added to the flask containing Inoculation Medium to a final concentration of 200 μM from a 1 M stock solution in 100% dimethyl sulfoxide and the solution was thoroughly mixed.

For each construct, 1 or 2 inoculating loops-full of *Agrobacterium* from the YEP plate were suspended in 15 mL of the Inoculation Medium/acetosyringone stock solution in a sterile, disposable, 50 mL centrifuge tube, and the optical density of the solution at 550 nm ($OD_{550}$) was measured in a spectrophotometer. The suspension was then diluted to $OD_{550}$ of 0.3 to 0.4 using additional Inoculation Medium/acetosyringone mixture. The tube of *Agrobacterium* suspension was then placed horizontally on a platform shaker set at about 75 rpm at room temperature and shaken for 1 to 4 hours while embryo dissection was performed.

Ear Sterilization and Embryo Isolation.

Maize immature embryos were obtained from plants of *Zea mays* inbred line B104 (Hallauer et al. (1997) Crop Science 37:1405-1406) grown in the greenhouse and self- or sib-pollinated to produce ears. The ears were harvested approximately 10 to 12 days post-pollination. On the experimental day, de-husked ears were surface-sterilized by immersion in a 20% solution of commercial bleach (ULTRA CLOROX® Germicidal Bleach, 6.15% sodium hypochlorite; with two drops of TWEEN 20) and shaken for 20 to 30 min, followed by three rinses in sterile deionized water in a laminar flow hood. Immature zygotic embryos (1.8 to 2.2 mm long) were aseptically dissected from each ear and randomly distributed into microcentrifuge tubes containing 2.0 mL of a suspension of appropriate *Agrobacterium* cells in liquid Inoculation Medium with 200 μM acetosyringone, into which 2 μL of 10% BREAK-THRU® S233 surfactant (EVONIK INDUSTRIES; Essen, Germany) was added. For a given set of experiments, embryos from pooled ears were used for each transformation.

*Agrobacterium* Co-Cultivation.

Following isolation, the embryos were placed on a rocker platform for 5 minutes. The contents of the tube were then poured onto a plate of Co-cultivation Medium, which contained 4.33 gm/L MS salts; 1×ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 200 μM acetosyringone in DMSO; and 3 gm/L GELZAN™, at pH 5.8. The liquid *Agrobacterium* suspension was removed with a sterile, disposable, transfer pipette. The embryos were then oriented with the scutellum facing up using sterile forceps with the aid of a microscope. The plate was closed, sealed with 3M™ MICROPORE™ medical tape, and placed in an incubator at 25° C. with continuous light at approximately 60 μmol m$^{-2}$s$^{-1}$ of Photosynthetically Active Radiation (PAR).

Callus Selection and Regeneration of Transgenic Events.

Following the Co-Cultivation period, embryos were transferred to Resting Medium, which was composed of 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino) ethanesulfonic acid monohydrate; PHYTOTECHNOLOGIES LABR.; Lenexa, Kans.); 250 mg/L Carbenicillin; and 2.3 gm/L GELZAN™; at pH 5.8. No more than 36 embryos were moved to each plate. The plates were placed in a clear plastic box and incubated at 27° C. with continuous light at approximately 50 µmol m$^{-2}$s$^{-1}$ PAR for 7 to 10 days. Callused embryos were then transferred (<18/plate) onto Selection Medium I, which was comprised of Resting Medium (above) with 100 nM R-Haloxyfop acid (0.0362 mg/L; for selection of calli harboring the AAD-1 gene). The plates were returned to clear boxes and incubated at 27° C. with continuous light at approximately 50 µmol m$^{-2}$s$^{-1}$ PAR for 7 days. Callused embryos were then transferred (<12/plate) to Selection Medium II, which was comprised of Resting Medium (above) with 500 nM R-Haloxyfop acid (0.181 mg/L). The plates were returned to clear boxes and incubated at 27° C. with continuous light at approximately 50 µmol m$^{-2}$s$^{-1}$ PAR for 14 days. This selection step allowed transgenic callus to further proliferate and differentiate.

Proliferating, embryogenic calli were transferred (<9/plate) to Pre-Regeneration medium. Pre-Regeneration Medium contained 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L AgNO$_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 0.181 mg/L Haloxyfop acid; at pH 5.8. The plates were stored in clear boxes and incubated at 27° C. with continuous light at approximately 50 µmol m$^{-2}$s$^{-1}$ PAR for 7 days. Regenerating calli were then transferred (<6/plate) to Regeneration Medium in PHYTATRAYS™ (SIGMA-ALDRICH) and incubated at 28° C. with 16 hours light/8 hours dark per day (at approximately 160 µmol m$^{-2}$s$^{-1}$ PAR) for 14 days or until shoots and roots develop. Regeneration Medium contained 4.33 gm/L MS salts; 1×ISU Modified MS Vitamins; 60 gm/L sucrose; 100 mg/L myo-inositol; 125 mg/L Carbenicillin; 3 gm/L GELLAN™ gum; and 0.181 mg/L R-Haloxyfop acid; at pH 5.8. Small shoots with primary roots were then isolated and transferred to Elongation Medium without selection. Elongation Medium contained 4.33 gm/L MS salts; 1×ISU Modified MS Vitamins; 30 gm/L sucrose; and 3.5 gm/L GELRITE™: at pH 5.8.

Transformed plant shoots selected by their ability to grow on medium containing Haloxyfop were transplanted from PHYTATRAYS™ to small pots filled with growing medium (PROMIX BX; PREMIER TECH HORTICULTURE), covered with cups or HUMI-DOMES (ARCO PLASTICS), and then hardened-off in a CONVIRON growth chamber (27° C. day/24° C. night, 16-hour photoperiod, 50-70% RH, 200 µmol m$^{-2}$s$^{-1}$ PAR). In some instances, putative transgenic plantlets were analyzed for transgene relative copy number by quantitative real-time PCR assays using primers designed to detect the AAD1 herbicide tolerance gene integrated into the maize genome. Further, qPCR assays were used to detect the presence of the linker and/or target sequence in putative transformants. Selected transformed plantlets were then moved into a greenhouse for further growth and testing.

Transfer and Establishment of T$_0$ Plants in the Greenhouse for Bioassay and Seed Production.

When plants reached the V3-V4 stage, they were transplanted into IE CUSTOM BLEND (PROFILE/METRO MIX 160) soil mixture and grown to flowering in the greenhouse (Light Exposure Type: Photo or Assimilation; High Light Limit: 1200 PAR; 16-hour day length; 27° C. day/24° C. night).

Plants to be used for insect bioassays were transplanted from small pots to TINUS™ 350-4 ROOTRAINERS® (SPENCER-LEMAIRE INDUSTRIES, Acheson, Alberta, Canada) (one plant per event per ROOTRAINER®). Approximately four days after transplanting to ROOTRAINERS®, plants were infested for bioassay.

Plants of the T$_1$ generation were obtained by pollinating the silks of T$_0$ transgenic plants with pollen collected from plants of non-transgenic elite inbred line B104 or other appropriate pollen donors, and planting the resultant seeds. Reciprocal crosses were performed when possible.

Example 7

Molecular Analyses of Transgenic Maize Tissues

Molecular analyses (e.g. RT-qPCR) of maize tissues were performed on samples from leaves collected from greenhouse grown plants on the same days that root feeding damage is assessed.

Results of RT-qPCR assays for the Per5 3'UTR were used to validate expression of the transgenes. Results of RT-qPCR assays for linker sequence (which is integral to the formation of dsRNA hairpin molecules) in expressed RNAs were used to validate the presence of hairpin transcripts. Transgene RNA expression levels were measured relative to the RNA levels of an endogenous maize gene.

DNA qPCR analyses to detect a portion of the AAD1 coding region in genomic DNA were used to estimate transgene insertion copy number. Samples for these analyses were collected from plants grown in environmental chambers. Results were compared to DNA qPCR results of assays designed to detect a portion of a single-copy native gene, and simple events (having one or two copies of rpL40 transgenes) were advanced for further studies in the greenhouse.

Additionally, qPCR assays designed to detect a portion of the spectinomycin-resistance gene (SpecR; harbored on the binary vector plasmids outside of the T-DNA) were used to determine if the transgenic plants contained extraneous integrated plasmid backbone sequences.

RNA Transcript Expression Level:

target qPCR. Callus cell events or transgenic plants were analyzed by real time quantitative PCR (qPCR) of the target sequence to determine the relative expression level of the full length hairpin transcript, as compared to the transcript level of an internal maize gene (SEQ ID NO:67; GENBANK Accession No. BT069734), which encodes a TIP4l-like protein (i.e., a maize homolog of GENBANK Accession No. AT4G34270; having a tBLASTX score of 74% identity). RNA was isolated using an Norgen BioTek Total RNA Isolation Kit (Norgen, Thorold, ON). The total RNA was subjected to an On Column DNaseI treatment according to the kit's suggested protocol. The RNA was then quantified on a NANODROP 8000 spectrophotometer (THERMO SCIENTIFIC) and concentration was normalized to 50 ng/µL. First strand cDNA was prepared using a HIGH CAPACITY cDNA SYNTHESIS KIT (INVITROGEN) in a 10 µL reaction volume with 5 µL denatured RNA, substantially according to the manufacturer's recommended protocol. The protocol was modified slightly to include the addition of 10 µL of 100 µM T20VN oligonucleotide (IDT) (SEQ ID NO:68; TTTTTTTTTTTTTTTTTTTTVN, where V is A, C, or G, and N is A, C, G, or T/U) into the 1 mL tube of random primer stock mix, in order to prepare a working stock of combined random primers and oligo dT.

Following cDNA synthesis, samples were diluted 1:3 with nuclease-free water, and stored at −20° C. until assayed.

Separate real-time PCR assays for the target gene and TIP41-like transcript were performed on a LIGHTCYCLER™ 480 (ROCHE DIAGNOSTICS, Indianapolis, Ind.) in 10 µL reaction volumes. For the target gene assay, reactions were run with Primers rpl40 (F) (SEQ ID NO:69) and rpl40 (R) (SEQ ID NO:70), and an IDT Custom Oligo probe rab5 PRB Set1, labeled with FAM and double quenched with Zen and Iowa Black quenchers (SEQ ID NO:111). For the TIP41-like reference gene assay, primers TIPmxF (SEQ ID NO:71) and TIPmxR (SEQ ID NO:72), and Probe HXTIP (SEQ ID NO:73) labeled with HEX (hexachlorofluorescein) were used.

All assays included negative controls of no-template (mix only). For the standard curves, a blank (water in source well) was also included in the source plate to check for sample cross-contamination. Primer and probe sequences are set forth in Table 6. Reaction components recipes for detection of the various transcripts are disclosed in Table 7, and PCR reactions conditions are summarized in Table 8. The FAM (6-Carboxy Fluorescein Amidite) fluorescent moiety was excited at 465 nm and fluorescence was measured at 510 nm; the corresponding values for the HEX (hexachlorofluorescein) fluorescent moiety were 533 nm and 580 nm.

Data were analyzed using LIGHTCYCLER™ Software v1.5 by relative quantification using a second derivative max algorithm for calculation of Cq values according to the supplier's recommendations. For expression analyses, expression values were calculated using the ΔΔCt method (i.e., 2−(Cq TARGET−Cq REF)), which relies on the comparison of differences of Cq values between two targets, with the base value of 2 being selected under the assumption that, for optimized PCR reactions, the product doubles every cycle.

Transcript Size and Integrity:

Northern Blot Assay. In some instances, additional molecular characterization of the transgenic plants is obtained by the use of Northern Blot (RNA blot) analysis to determine the molecular size of the rpL40 hairpin RNA in transgenic plants expressing a rpL40 dsRNA.

All materials and equipment are treated with RNAZAP (AMBION/INVITROGEN) before use. Tissue samples (100 mg to 500 mg) are collected in 2 mL SAFELOCK EPPENDORF tubes, disrupted with a KLECKO™ tissue pulverizer (GARCIA MANUFACTURING, Visalia, CA) with three tungsten beads in 1 mL of TRIZOL (INVITROGEN) for 5 min, then incubated at room temperature (RT) for 10 min. Optionally, the samples are centrifuged for 10 min at 4° C. at 11,000 rpm and the supernatant is transferred into a fresh 2 mL SAFELOCK EPPENDORF tube. After 200 μL of chloroform are added to the homogenate, the tube is mixed by inversion for 2 to 5 min, incubated at RT for 10 minutes, and centrifuged at 12,000×g for 15 min at 4° C. The top phase is transferred into a sterile 1.5 mL EPPENDORF tube, 600 μL of 100% isopropanol are added, followed by incubation at RT for 10 min to 2 hr, and then centrifuged at 12,000×g for 10 min at 4° to 25° C. The supernatant is discarded and the RNA pellet is washed twice with 1 mL of 70% ethanol, with centrifugation at 7,500×g for 10 min at 4° to 25° C. between washes. The ethanol is discarded and the pellet is briefly air dried for 3 to 5 min before resuspending in 50 μL of nuclease-free water.

Total RNA is quantified using the NANODROP8000® (THERMO-FISHER) and samples are normalized to 5 μg/10 μL. 10 μL of glyoxal (AMBION/INVITROGEN) are then added to each sample. Five to 14 ng of DIG RNA standard marker mix (ROCHE APPLIED SCIENCE, Indianapolis, Ind.) are dispensed and added to an equal volume of glyoxal. Samples and marker RNAs are denatured at 50° C. for 45 min and stored on ice until loading on a 1.25% SEAKEM

TABLE 6

Oligonucleotide sequences for molecular analyses of transcript levels in transgenic maize.

| Target | Oligonucleotide | SEQ ID NO. | Sequence |
|---|---|---|---|
| rpl40 | rpl40(F) | 58 | CACCAGATCAGCAACGTCTAA |
| rpl40 | rpl40(R) | 59 | CCAAATGGAGTGTCGATTCCT |
| rpl40 | rpl40 (FAM-Probe) | 111 | CGTCCATCTTCCAATTGTTTGCCAGC |
| TIP41 | TIPmxF | 60 | TGAGGGTAATGCCAACTGGTT |
| TIP41 | TIPmxR | 61 | GCAATGTAACCGAGTGTCTCTCAA |
| TIP41 | HXTIP (HEX-Probe) | 62 | TTTTTGGCTTAGAGTTGATGGTGTACTGATGA |

*TIP41-like protein.

TABLE 7

PCR reaction recipes for transcript detection.

| Component | Target Gene | TIP-like Gene |
|---|---|---|
| | Final Concentration | |
| Roche Buffer | 1X | 1X |
| rpl40 (F) | 0.4 μM | 0 |
| rpl40 (R) | 0.4 μM | 0 |
| rpl40 (FAM) | 0.2 μM | 0 |
| HEXtipZM F | 0 | 0.4 μM |
| HEXtipZM R | 0 | 0.4 μM |
| HEXtipZMP (HEX) | 0 | 0.2 μM |
| cDNA (2.0 μL) | NA | NA |
| Water | To 10 μL | To 10 μL |

TABLE 8

Thermocycler conditions for RNA qPCR. Target Gene and TIP41-like Gene Detection

| Process | Temp. | Time | No. Cycles |
|---|---|---|---|
| Target Activation | 95° C. | 10 min | 1 |
| Denature | 95° C. | 10 sec | 40 |
| Extend | 60° C. | 40 sec | |
| Acquire FAM or HEX | 72° C. | 1 sec | |
| Cool | 40° C. | 10 sec | 1 |

GOLD agarose (LONZA, Allendale, N.J.) gel in NORTHERNMAX 10× glyoxal running buffer (AMBION/INVITROGEN). RNAs are separated by electrophoresis at 65 volts/30 mA for 2 hr and 15 min.

Following electrophoresis, the gel is rinsed in 2×SSC for 5 min and imaged on a GEL DOC station (BIORAD, Hercules, Calif.), then the RNA is passively transferred to a nylon membrane (MILLIPORE) overnight at RT, using 10×SSC as the transfer buffer (20×SSC consists of 3 M sodium chloride and 300 mM trisodium citrate, pH 7.0). Following the transfer, the membrane is rinsed in 2×SSC for 5 minutes, the RNA is UV-crosslinked to the membrane (AGILENT/STRATAGENE), and the membrane is allowed to dry at RT for up to 2 days.

The membrane is prehybridized in ULTRAHYB buffer (AMBION/INVITROGEN) for 1 to 2 hr. The probe consists of a PCR amplified product containing the sequence of interest, labeled with digoxygenin by means of a ROCHE APPLIED SCIENCE DIG procedure. Hybridization in recommended buffer is overnight at a temperature of 60° C. in hybridization tubes. Following hybridization, the blot is subjected to DIG washes, wrapped, exposed to film for 1 to 30 minutes, then the film is developed, all by methods recommended by the supplier of the DIG kit.

Transgene Copy Number Determination.

Maize leaf pieces approximately equivalent to 2 leaf punches were collected in 96-well collection plates (QIAGEN). Tissue disruption was performed with a KLECKO™ tissue pulverizer (GARCIA MANUFACTURING, Visalia, CA) in BIOSPRINT96 AP1 lysis buffer (supplied with a BIOSPRINT96 PLANT KIT; QIAGEN) with one stainless steel bead. Following tissue maceration, genomic DNA (gDNA) was isolated in high throughput format using a BIOSPRINT96 PLANT KIT and a BIOSPRINT96 extraction robot. Genomic DNA was diluted 1:3 DNA:water prior to setting up the qPCR reaction.

qPCR analysis. Transgene detection by hydrolysis probe assay was performed by real-time PCR using a LIGHTCYCLER®480 system. Oligonucleotides used in hydrolysis probe assays to detect the target gene, the linker sequence (e.g., the loop), or to detect a portion of the SpecR gene (i.e. the spectinomycin resistance gene borne on the binary vector plasmids; SEQ ID NO:74; SPC1 oligonucleotides in Table 9), were designed using LIGHTCYCLER® PROBE DESIGN SOFTWARE 2.0. Further, oligonucleotides used in hydrolysis probe assays to detect a segment of the AAD-1 herbicide tolerance gene (SEQ ID NO:75; GAAD1 oligonucleotides in Table 9) were designed using PRIMER EXPRESS software (APPLIED BIOSYSTEMS). Table 9 shows the sequences of the primers and probes. Assays were multiplexed with reagents for an endogenous maize chromosomal gene (Invertase (SEQ ID NO:76; GENBANK Accession No: U16123; referred to herein as IVR1), which served as an internal reference sequence to ensure gDNA was present in each assay. For amplification, LIGHTCYCLER®480 PROBES MASTER mix (ROCHE APPLIED SCIENCE) was prepared at 1× final concentration in a 10 µL volume multiplex reaction containing 0.4 µM of each primer and 0.2 µM of each probe (Table 10). A two step amplification reaction was performed as outlined in Table 11. Fluorophore activation and emission for the FAM- and HEX-labeled probes were as described above; CY5 conjugates were excited maximally at 650 nm and fluoresce maximally at 670 nm.

Cp scores (the point at which the fluorescence signal crosses the background threshold) were determined from the real time PCR data using the fit points algorithm (LIGHTCYCLER® SOFTWARE release 1.5) and the Relative Quant module (based on the ΔΔCt method). Data were handled as described previously (above; RNA qPCR).

TABLE 9

Sequences of primers and probes (with fluorescent conjugate) for gene copy number determination and binary vector plasmid backbone detection.

| Name | SEQ ID NO: | Sequence |
| --- | --- | --- |
| Loop-F | 86 | GGAACGAGCTGCTTGCGTAT |
| Loop-R | 87 | CACGGTGCAGCTGCTTGCTG |
| Loop-P (FAM) | 88 | TCCCTTCCGTAGTCAGAG |
| GAAD1-F | 77 | TGTTCGGTTCCCTCTACCAA |
| GAAD1-R | 78 | CAACATCCATCACCTTGACTGA |
| GAAD1-P (FAM) | 79 | CACAGAACCGTCGCTTCAGCAACA |
| IVR1-F | 80 | TGGCGGACGACGACTTGT |
| IVR1-R | 81 | AAAGTTTGGAGGCTGCCGT |
| IVR1-P (HEX) | 82 | CGAGCAGACCGCCGTGTACTTCTACC |
| SPC1A | 83 | CTTAGCTGGATAACGCCAC |
| SPC1S | 84 | GACCGTAAGGCTTGATGAA |
| TQSPEC (CY5*) | 85 | CGAGATTCTCCGCGCTGTAGA |

CY5 = Cyanine-5

TABLE 10

Reaction components for gene copy number analyses and plasmid backbone detection.

| Component | Amt. (µL) | Stock | Final Conc'n |
| --- | --- | --- | --- |
| 2x Buffer | 5.0 | 2x | 1x |
| Appropriate Forward Primer | 0.4 | 10 µM | 0.4 |
| Appropriate Reverse Primer | 0.4 | 10 µM | 0.4 |
| Appropriate Probe | 0.4 | 5 µM | 0.2 |
| IVR1-Forward Primer | 0.4 | 10 µM | 0.4 |
| IVR1-Reverse Primer | 0.4 | 10 µM | 0.4 |
| IVR1-Probe | 0.4 | 5 µM | 0.2 |
| H₂O | 0.6 | NA* | NA |
| gDNA | 2.0 | ND** | ND |
| Total | 10.0 | | |

*NA = Not Applicable
**ND = Not Determined

TABLE 11

Thermocycler conditions for DNA qPCR Genomic copy number analyses

| Process | Temp. | Time | No. Cycles |
| --- | --- | --- | --- |
| Target Activation | 95° C. | 10 min | 1 |
| Denature | 95° C. | 10 sec | 40 |
| Extend & Acquire FAM, HEX, or CY5 | 60° C. | 40 sec | |
| Cool | 40° C. | 10 sec | 1 |

Example 8

Bioassay of Transgenic Maize

In Vitro Insect Bioassays.

Bioactivity of dsRNA of the subject invention produced in plant cells is demonstrated by bioassay methods. See, e.g., Baum et al. (2007) Nat. Biotechnol. 25(11):1322-1326. One is able to demonstrate efficacy, for example, by feeding various plant tissues or tissue pieces derived from a plant producing an insecticidal dsRNA to target insects in a controlled feeding environment. Alternatively, extracts are prepared from various plant tissues derived from a plant producing the insecticidal dsRNA and the extracted nucleic acids are dispensed on top of artificial diets for bioassays as previously described herein. The results of such feeding assays are compared to similarly conducted bioassays that employ appropriate control tissues from host plants that do not produce an insecticidal dsRNA, or to other control samples.

Insect Bioassays with Transgenic Maize Events.

Two western corn rootworm larvae (1 to 3 days old) hatched from washed eggs are selected and placed into each well of the bioassay tray. The wells are then covered with a "PULL N' PEEL" tab cover (BIO-CV-16, BIO-SERV) and placed in a 28° C. incubator with an 18 hr/6 hr light/dark cycle. Nine days after the initial infestation, the larvae are assessed for mortality, which is calculated as the percentage of dead insects out of the total number of insects in each treatment. The insect samples are frozen at −20° C. for two days, then the insect larvae from each treatment are pooled and weighed. The percent of growth inhibition is calculated as the mean weight of the experimental treatments divided by the mean of the average weight of two control well treatments. The data are expressed as a Percent Growth Inhibition (of the Negative Controls). Mean weights that exceed the control mean weight are normalized to zero.

Insect Bioassays in the Greenhouse.

Western corn rootworm (WCR, *Diabrotica virgifera virgifera* LeConte) eggs were received in soil from CROP CHARACTERISTICS (Farmington, Minn.). WCR eggs were incubated at 28° C. for 10 to 11 days. Eggs were washed from the soil, placed into a 0.15% agar solution, and the concentration was adjusted to approximately 75 to 100 eggs per 0.25 mL aliquot. A hatch plate was set up in a Petri dish with an aliquot of egg suspension to monitor hatch rates.

The soil around the maize plants growing in ROOTRAIN-ERS® was infested with 150 to 200 WCR eggs. The insects were allowed to feed for 2 weeks, after which time a "Root Rating" was given to each plant. A Node-Injury Scale was utilized for grading essentially according to Oleson et al. (2005, J. Econ. Entomol. 98:1-8). Plants which passed this bioassay were transplanted to 5-gallon pots for seed production. Transplants were treated with insecticide to prevent further rootworm damage and insect release in the greenhouses. Plants were hand pollinated for seed production. Seeds produced by these plants were saved for evaluation at the Ti and subsequent generations of plants.

Transgenic negative control plants were generated by transformation with vectors harboring genes designed to produce a yellow fluorescent protein (YFP). Bioassays were conducted with negative controls included in each set of plant materials.

TABLE 12

Root Damage Rating based on greenhouse bioassay and relative transcript expression level results of rpl40-expressing maize plants and YFP control plants.

| Sample ID | Gene of Interest | ssRNA | dsRNA | Root Rating |
|---|---|---|---|---|
| rpl40 Events | | | | |
| 126164[1]-002 | rpl40 | 0.291 | 0.096 | 1 |
| 126164[1]-003 | rpl40 | | 0.063 | 1 |
| 126164[1]-005 | rpl40 | 0.178 | 4.317 | 1 |
| 126164[1]-007 | rpl40 | 0.261 | 3.945 | 1 |
| 126164[1]-008 | rpl40 | 0.232 | 3.227 | 1 |
| 126164[1]-010 | rpl40 | 0.136 | 0.818 | 1 |
| 126164[1]-011 | rpl40 | 0.202 | 3.387 | 1 |
| 126164[1]-012 | rpl40 | 0.356 | 4.408 | 1 |
| 126164[1]-013 | rpl40 | 0.346 | 4.228 | 1 |
| 126164[1]-014 | rpl40 | 0.221 | 1.945 | 1 |
| 126164[1]-015 | rpl40 | 0.325 | 2.770 | 1 |
| 126164[1]-018 | rpl40 | 0.31 | 3.864 | 1 |
| 126164[1]-023 | rpl40 | 0.295 | 3.204 | 1 |
| 126164[1]-028 | rpl40 | 0.281 | 4.258 | 1 |
| 126164[1]-030 | rpl40 | 0.295 | 5.205 | 1 |
| YFP Events | | | | |
| 126944[5]-026 | YFPv2 | | | 1 |
| 126944[6]-031 | YFPv2 | | | 1 |
| 126944[7]-038 | YFPv2 | | | |
| 126944[7]-051 | YFPv2 | | | 1 |
| 126944[7]-052 | YFPv2 | | | 1 |

The measurement of dsRNA relative to the endogenous reference gene (TIP-41 like protein) ranges from 0.063 to 5.205. Root ratings were not significantly different from YFP controls. The relative expression levels of these constructs could be insufficient to provide root protection.

Example 9

Transgenic *Zea mays* Comprising Coleopteran Pest Sequences

Ten to 20 transgenic $T_0$ *Zea mays* plants are generated as described in EXAMPLE 6. A further 10-20 $T_1$ *Zea mays* independent lines expressing hairpin dsRNA for an RNAi construct are obtained for corn rootworm challenge. Hairpin dsRNA may be derived comprising all or part of SEQ ID NOs:1, 3, and 5. Additional hairpin dsRNAs may be derived, for example, from coleopteran pest sequences such as, for example, Caf1-180 (U.S. Patent Application Publication No. 2012/0174258), VatpaseC (U.S. Patent Application Publication No. 2012/0174259), Rho1 (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), ROP (U.S. patent application Ser. No. 14/577,811), RNA polymerase 11140 (U.S. patent application Ser. No. 14/577,854), RNA polymerase I1 (U.S. Patent Application No. 62/133,214), RNA polymerase II-215 (U.S. Patent Application No. 62/133,202), RNA polymerase 33 (U.S. Patent Application No. 62/133,210), ncm (U.S. Patent Application No. 62/095,487), Dre4 (U.S. patent application Ser. No. 14/705,807), COPI alpha (U.S. Patent Application No. 62/063,199), COPI beta (U.S. Patent Application No. 62/063,203), COPI gamma (U.S. Patent Application No. 62/063,192), or COPI delta (U.S. Patent Application No. 62/063,216), spt5 (U.S. Patent Application No. 62/168,613), and spt6 (U.S. Patent Application No. 62/168,606). These are confirmed through RT-PCR or other molecular analysis methods.

Total RNA preparations from selected independent T$_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic Zea mays plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development and viability of feeding coleopteran pests.

In planta delivery of dsRNA, siRNA or miRNA corresponding to target genes and the subsequent uptake by coleopteran pests through feeding results in down-regulation of the target genes in the coleopteran pest through RNA-mediated gene silencing. When the function of a target gene is important at one or more stages of development, the growth, development, and reproduction of the coleopteran pest is affected, and in the case of at least one of WCR, NCR, SCR, MCR, *D. balteata* LeConte, *D. u. tenella*, and *D. u. undecimpunctata* Mannerheim, leads to failure to successfully infest, feed, develop, and/or reproduce, or leads to death of the coleopteran pest. The choice of target genes and the successful application of RNAi is then used to control coleopteran pests.

Phenotypic Comparison of Transgenic RNAi Lines and Nontransformed *Zea mays*.

Target coleopteran pest genes or sequences selected for creating hairpin dsRNA have no similarity to any known plant gene sequence. Hence it is not expected that the production or the activation of (systemic) RNAi by constructs targeting these coleopteran pest genes or sequences will have any deleterious effect on transgenic plants. However, development and morphological characteristics of transgenic lines are compared with nontransformed plants, as well as those of transgenic lines transformed with an "empty" vector having no hairpin-expressing gene. Plant root, shoot, foliage and reproduction characteristics are compared. Plant shoot characteristics such as height, leaf numbers and sizes, time of flowering, floral size and appearance are recorded. In general, there are no observable morphological differences between transgenic lines and those without expression of target iRNA molecules when cultured in vitro and in soil in the glasshouse.

Example 10

Transgenic *Zea mays* Comprising a Coleopteran Pest Sequence and Additional RNAi Constructs A transgenic *Zea mays* plant comprising a heterologous coding sequence in its genome that is transcribed into an iRNA molecule that targets an organism other than a coleopteran pest is secondarily transformed via *Agrobacterium* or WHISKERS™ methodologies (see Petolino and Arnold (2009) Methods Mol. Biol. 526:59-67) to produce one or more insecticidal dsRNA molecules (for example, at least one dsRNA molecule including a dsRNA molecule targeting a gene comprising SEQ ID NOs:1, 3, or 5). Plant transformation plasmid vectors prepared essentially as described in EXAMPLE 4 are delivered via *Agrobacterium* or WHISKERS™-mediated transformation methods into maize suspension cells or immature maize embryos obtained from a transgenic Hi II or B104 *Zea mays* plant comprising a heterologous coding sequence in its genome that is transcribed into an iRNA molecule that targets an organism other than a coleopteran pest.

Example 11

Transgenic *Zea mays* Comprising an RNAi Construct and Additional Coleopteran Pest Control Sequences A transgenic *Zea mays* plant comprising a heterologous coding sequence in its genome that is transcribed into an iRNA molecule that targets a coleopteran pest organism (for example, at least one dsRNA molecule including a dsRNA molecule targeting a gene comprising SEQ ID NOs:1, 3, or 5) is secondarily transformed via *Agrobacterium* or WHISKERS™ methodologies (see Petolino and Arnold (2009) Methods Mol. Biol. 526:59-67) to produce one or more insecticidal protein molecules, for example, Cry3 or Cry34/Cry35Ab1 insecticidal proteins. Plant transformation plasmid vectors prepared essentially as described in EXAMPLE 4 are delivered via *Agrobacterium* or WHISKERS™-mediated transformation methods into maize suspension cells or immature maize embryos obtained from a transgenic B104 *Zea mays* plant comprising a heterologous coding sequence in its genome that is transcribed into an iRNA molecule that targets a coleopteran pest organism. Doubly-transformed plants are obtained that produce iRNA molecules and insecticidal proteins for control of coleopteran pests.

Example 12

Mortality of Neotropical Brown Stink Bug (*Euschistus heros*) Following rpL40 RNAi Injection Neotropical Brown Stink Bug (BSB; *Euschistus heros*) Colony.

BSB were reared in a 27° C. incubator, at 65% relative humidity, with 16:8 hour light: dark cycle. One gram of eggs collected over 2-3 days were seeded in 5 L containers with filter paper discs at the bottom; the containers were covered with #18 mesh for ventilation. Each rearing container yielded approximately 300-400 adult BSB. At all stages, the insects were fed fresh green beans three times per week, a sachet of seed mixture that contained sunflower seeds, soybeans, and peanuts (3:1:1 by weight ratio) was replaced once a week. Water was supplemented in vials with cotton plugs as wicks. After the initial two weeks, insects were transferred onto new container once a week.

BSB Artificial Diet.

BSB artificial diet prepared as follows (used within two weeks of preparation). Lyophilized green beans were blended to a fine powder in a MAGIC BULLET® blender while raw (organic) peanuts were blended in a separate MAGIC BULLET® blender. Blended dry ingredients were combined (weight percentages: green beans, 35%; peanuts, 35%; sucrose, 5%; Vitamin complex (e.g. Vanderzant Vitamin Mixture for insects, SIGMA-ALDRICH, Catalog No. V1007), 0.9%); in a large MAGIC BULLET® blender, which was capped and shaken well to mix the ingredients.

The mixed dry ingredients were then added to a mixing bowl. In a separate container, water and benomyl anti-fungal agent (50 ppm; 25 µL of a 20,000 ppm solution/50 mL diet solution) were mixed well and then added to the dry ingredient mixture. All ingredients were mixed by hand until the solution was fully blended. The diet was shaped into desired sizes, wrapped loosely in aluminum foil, heated for 4 hours at 60° C., then cooled and stored at 4° C.

BSB Transcriptome Assembly.

Six stages of BSB development were selected for mRNA library preparation. Total RNA was extracted from insects frozen at −70° C. and homogenized in 10 volumes of Lysis/Binding buffer in Lysing MATRIX A 2 mL tubes (MP BIOMEDICALS, Santa Ana, Calif.) on a FastPrep®-24 Instrument (MP BIOMEDICALS). Total mRNA was extracted using a mirVana™ miRNA Isolation Kit (AMBION; INVITROGEN) according to the manufacturer's protocol. RNA sequencing using an Illumina® HiSeq™ system (San Diego, Calif.) provided candidate target gene sequences for use in RNAi insect control technology. HiSeq™ generated a total of about 378 million reads for the six samples. The reads were assembled individually for each sample using TRINITY assembler software (Grabherr et al. (2011) Nature Biotech. 29:644-652). The assembled transcripts were combined to generate a pooled transcriptome. This BSB pooled transcriptome contains 378,457 sequences.

BSB_rpL40 Ortholog Identification.

A tBLASTn search of the BSB pooled transcriptome was performed using as query the *Drosophila* rpL40 protein isoform A and B sequences: GENBANK Accession Nos. NP_476776 and NP_001260018. BSB rpL40 (SEQ ID NO:89) was identified as a *Euschistus heron* candidate target gene product with predicted peptide sequence SEQ ID NO:90.

Template Preparation and dsRNA Synthesis.

cDNA was prepared from total BSB RNA extracted from a single young adult insect (about 90 mg) using TRIzol® Reagent (LIFE TECHNOLOGIES). The insect was homogenized at room temperature in a 1.5 mL microcentrifuge tube with 200 µL of TRIzol® using a pellet pestle (FISHERBRAND Catalog No. 12-141-363) and Pestle Motor Mixer (COLE-PARMER, Vernon Hills, Ill.). Following homogenization, an additional 800 µL of TRIzol® was added, the homogenate was vortexed, and then incubated at room temperature for five minutes. Cell debris was removed by centrifugation and the supernatant was transferred to a new tube. Following manufacturer-recommended TRIzol® extraction protocol for 1 mL of TRIzol®, the RNA pellet was dried at room temperature and resuspended in 200 µL of Tris Buffer from a GFX PCR DNA AND GEL EXTRACTION KIT (Illustra™; GE HEALTHCARE LIFE SCIENCES) using Elution Buffer Type 4 (i.e. 10 mM Tris-HCl pH8.0). RNA concentration was determined using a NANODROP™ 8000 spectrophotometer (THERMO SCIENTIFIC, Wilmington, Del.).

cDNA Amplification.

cDNA was reverse-transcribed from 5 µg of BSB total RNA template and oligo dT primer using a SUPERSCRIPT III FIRST-STRAND SYNTHESIS SYSTEM™ for RT-PCR (INVITROGEN), following the supplier's recommended protocol. The final volume of the transcription reaction was brought to 100 µL with nuclease-free water.

Primers BSB_rpL40-1-For (SEQ ID NO:93) and BSB_rpL40-1-Rev (SEQ ID NO:94) were used to amplify BSB_rpL40 region 1, also referred to as BSB_rpL40 reg1 template. The DNA template was amplified by touch-down PCR (annealing temperature lowered from 60° C. to 50° C. in a 1° C./cycle decrease) with 1 µL of cDNA (above) as the template. A fragment comprising a 410 bp segment of BSB_rpL40 reg1 (SEQ ID NO:91) was generated during 35 cycles of PCR. The above procedure was also used to amplify a 301 bp negative control template YFPv2 (SEQ ID NO:95) using YFPv2-F (SEQ ID NO:96) and YFPv2-R (SEQ ID NO:97) primers. The BSB_rpL40 and YFPv2 primers contained a T7 phage promoter sequence (SEQ ID NO:16) at their 5' ends, and thus enabled the use of YFPv2 and BSB_rpL40 DNA fragments for dsRNA transcription.

dsRNA Synthesis.

dsRNA was synthesized using 2 µL of PCR product (above) as the template with a MEGAscript™ RNAi kit (AMBION) used according to the manufacturer's instructions. (See FIG. 1). dsRNA was quantified on a NANODROP™ 8000 spectrophotometer and diluted to 500 ng/µL in nuclease-free 0.1×TE buffer (1 mM Tris HCL, 0.1 mM EDTA, pH7.4).

Injection of dsRNA into BSB Hemoceol.

BSB were reared on a green bean and seed diet, as the colony, in a 27° C. incubator at 65% relative humidity and 16:8 hour light: dark photoperiod. Second instar nymphs (each weighing 1 to 1.5 mg) were gently handled with a small brush to prevent injury and were placed in a Petri dish on ice to chill and immobilize the insects. Each insect was injected with 55.2 nL of a 500 ng/µL dsRNA solution (i.e. 27.6 ng dsRNA; dosage of 18.4 to 27.6 µg/g body weight). Injections were performed using a NANOJECT™ II injector (DRUMMOND SCIENTIFIC, Broomhall, Pa.) equipped with an injection needle pulled from a Drummond 3.5 inch #3-000-203-G/X glass capillary. The needle tip was broken and the capillary was backfilled with light mineral oil, then filled with 2 to 3 µL of dsRNA. dsRNA was injected into the abdomen of the nymphs (10 insects injected per dsRNA per trial), and the trials were repeated on three different days. Injected insects (5 per well) were transferred into 32-well trays (Bio-RT-32 Rearing Tray; BIO-SERV, Frenchtown, N.J.) containing a pellet of artificial BSB diet and covered with Pull-N-Peel™ tabs (BIO-CV-4; BIO-SERV). Moisture was supplied by means of 1.25 mL of water in a 1.5 mL microcentrifuge tube with a cotton wick. The trays were incubated at 26.5° C., 60% humidity and 16:8 hour light: dark photoperiod. Viability counts and weights were taken on day 7 after the injections.

Injections Identified BSB_rpL40 as a Lethal dsRNA Target.

dsRNA that targets segment of YFP coding region, YFPv2 was used as a negative control in BSB injection experiments. As summarized in Table 13, 27.6 ng of BSB_rpL40 reg1 dsRNA injected into the hemoceol of $2^{nd}$ instar BSB nymphs produced high mortality within seven days. The mortality caused by BSB_rpL40 reg1 dsRNA was significantly different from that seen with the same amount of injected YFPv2 dsRNA (negative control), with p=0.00263 (Student's t-test).

TABLE 13

Results of BSB_rpL40 reg1 dsRNA injection into the hemoceol of $2^{nd}$ instar Brown Stink Bug nymphs seven days after injection.

| Treatment* | N Trials | Mean % Mortality | SEM† | p value t-test |
|---|---|---|---|---|
| BSB rpL40 reg1 | 3 | 100 | 0 | 9.89E−05 |
| Not injected | 3 | 10 | 6 | 1.58E−01 |
| YFP v2 dsRNA | 3 | 0 | 0 | |

*Ten insects injected per trial for each dsRNA.
†SEM—Standard error of the mean

Example 13

**Transgenic *Zea mays* Comprising Hemipteran Pest Sequences**

Ten to 20 transgenic $T_0$ *Zea mays* plants harboring expression vectors for nucleic acids comprising SEQ ID NOs:89, 91, and/or 92 are generated as described in EXAMPLE 7. A further 10-20 $T_1$ *Zea mays* independent lines expressing hairpin dsRNA for an RNAi construct are obtained for BSB challenge. Hairpin dsRNA may be derived as set forth in SEQ ID NO:91, SEQ ID NO:92, or otherwise further comprising SEQ ID NO:89. These are confirmed through RT-PCR or other molecular analysis methods. Total RNA preparations from selected independent $T_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development and viability of feeding hemipteran pests.

In planta delivery of dsRNA, siRNA, shRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and reproduction of the hemipteran pest is affected, and in the case of at least one of *Euschistus heros*, *Piezodorus guildinii*, *Halyomorpha halys*, *Nezara viridula*, *Acrosternum hilare*, and *Euschistus servus* leads to failure to successfully infest, feed, develop, and/or reproduce, or leads to death of the hemipteran pest. The choice of target genes and the successful application of RNAi is then used to control hemipteran pests.

Phenotypic Comparison of Transgenic RNAi Lines and Nontransformed *Zea mays*.

Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with nontransformed plants, as well as those of transgenic lines transformed with an "empty" vector having no hairpin-expressing gene. Plant root, shoot, foliage and reproduction characteristics are compared. There is no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 14

**Transgenic *Glycine max* Comprising Hemipteran Pest Sequences**

Ten to 20 transgenic $T_0$ *Glycine max* plants harboring expression vectors for nucleic acids comprising SEQ ID NOs:89, 91 and/or 92 are generated as is known in the art, including for example by *Agrobacterium*-mediated transformation, as follows. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of Split-Seed Soybeans.

The split soybean seed comprising a portion of an embryonic axis protocol required preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation.

The split soybean seeds comprising a partial portion of the embryonic axis are then immersed for about 30 minutes in a solution of *Agrobacterium tumefaciens* (e.g., strain EHA 101 or EHA 105) containing binary plasmid comprising SEQ ID NOs:89, 91 and/or 92. The *Agrobacterium tumefaciens* solution is diluted to a final concentration of $\lambda$=0.6 $OD_{650}$ before immersing the cotyledons comprising the embryo axis.

Co-Cultivation.

Following inoculation, the split soybean seed is allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot Induction.

After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (LIBERTY®).

Shoot Elongation.

After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L Na$_2$EDTA, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 μmol/m$^2$ sec.

Rooting.

Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L Na$_2$EDTA, 20 g/L sucrose and 0.59 g/L MES, 50 mg/L asparagine, 100 mg/L L-pyroglutamic acid 7 g/L Noble agar, pH 5.6) in phyta trays.

Cultivation.

Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/m$^2$ sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

A further 10-20 T$_1$ *Glycine max* independent lines expressing hairpin dsRNA for an RNAi construct are obtained for BSB challenge. Hairpin dsRNA may be derived as set forth in SEQ ID NOs:91-92, or otherwise further comprising SEQ ID NO:89. These are confirmed through RT-PCR or other molecular analysis methods. Total RNA preparations from selected independent T$_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Glycine max* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development and viability of feeding hemipteran pests.

In planta delivery of dsRNA, siRNA, shRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and reproduction of the hemipteran pest is affected, and in the case of at least one of *Euschistus heros, Piezodorus guildinii, Halyomorpha halys, Nezara viridula, Acrosternum hilare*, and *Euschistus servus* leads to failure to successfully infest, feed, develop, and/or reproduce, or leads to death of the hemipteran pest. The choice of target genes and the successful application of RNAi is then used to control hemipteran pests.

Phenotypic comparison of transgenic RNAi lines and nontransformed *Glycine max* Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with nontransformed plants, as well as those of transgenic lines transformed with an "empty" vector having no hairpin-expressing gene. Plant root, shoot, foliage and reproduction characteristics are compared. There is no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 15

*E. heros* Bioassays on Artificial Diet

In dsRNA feeding assays on artificial diet, 32-well trays are set up with an ~18 mg pellet of artificial diet and water, as for injection experiments (EXAMPLE 12). dsRNA at a concentration of 200 ng/μl is added to the food pellet and water sample, 100 μl to each of two wells. Five $2^{nd}$ instar *E. heros* nymphs are introduced into each well. Water samples and dsRNA that targets YFP transcript are used as negative controls. The experiments are repeated on three different days. Surviving insects are weighed and the mortality rates are determined after 8 days of treatment.

Example 16

Transgenic *Arabidopsis thaliana* Comprising Hemipteran Pest Sequences

*Arabidopsis* transformation vectors containing a target gene construct for hairpin formation comprising segments of rpL40 (SEQ ID NO:89) are generated using standard molecular methods similar to EXAMPLE 4. *Arabidopsis* transformation is performed using standard *Agrobacterium*-based procedure. T$_1$ seeds are selected with glufosinate tolerance selectable marker. Transgenic T$_1$ *Arabidopsis* plants are generated and homozygous simple-copy T$_2$ transgenic plants are generated for insect studies. Bioassays are performed on growing *Arabidopsis* plants with inflorescences. Five to ten insects are placed on each plant and monitored for survival within 14 days.

Construction of *Arabidopsis* Transformation Vectors.

Entry clones based on an entry vector harboring a target gene construct for hairpin formation comprising a segment of rpL40 (SEQ ID NO:89) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a target gene segment in opposite orientations, the two segments being separated by a linker sequence (e.g., a loop (such as SEQ ID NO:112) or an ST-LS1 intron (Vancanneyt et al. (1990) Mol. Gen. Genet. 220(2):245-50)). Thus, the primary mRNA transcript contains the two rpL40 gene segment sequences as large inverted repeats of one another, separated by the linker sequence. A copy of a *Arabidopsis thaliana* ubiquitin 10 promoter (Callis et al. (1990) J. Biological Chem. 265:12486-12493) is used to drive production of the primary mRNA hairpin transcript, and a fragment comprising a 3' untranslated region from Open Reading Frame 23 of *Agrobacterium tumefaciens* (AtuORF23 3' UTR v1; U.S. Pat. No. 5,428,147) is used to terminate transcription of the hairpin-RNA-expressing gene.

The hairpin clone within an entry vector described above is used in standard GATEWAY® recombination reaction with a typical binary destination vector to produce hairpin RNA expression transformation vectors for *Agrobacterium*-mediated *Arabidopsis* transformation.

The binary destination vector comprises a herbicide tolerance gene, DSM-2v2 (U.S. Patent App. No. 2011/0107455), under the regulation of a Cassava vein mosaic virus promoter (CsVMV Promoter v2, U.S. Pat. No. 7,601,885; Verdaguer et al, (1996) Plant Molecular Biology, 31:1129-1139). A fragment comprising a 3' untranslated region from Open Reading Frame 1 of *Agrobacterium tumefaciens* (AtuORF1 3' UTR v6; Huang et al, (1990) J. Bacteriol, 172:1814-1822) is used to terminate transcription of the DSM2v2 mRNA.

A negative control binary construct, which comprises a gene that expresses a YFP hairpin RNA, is constructed by means of standard GATEWAY® recombination reactions with a typical binary destination vector and entry vector. An entry construct comprises a YFP hairpin sequence (hpYFP v2-1, SEQ ID NO:89) under the expression control of an *Arabidopsis* Ubiquitin 10 promoter (as above) and a fragment comprising an ORF23 3' untranslated region from *Agrobacterium tumefaciens* (as above).

Production of Transgenic *Arabidopsis* Comprising Insecticidal Hairpin RNAs: *Agrobacterium*-Mediated Transformation.

Binary plasmids containing hairpin sequences are electroporated into *Agrobacterium* strain GV3101 (pMP90RK). The recombinant *Agrobacterium* clones are confirmed by restriction analysis of plasmids preparations of the recombinant *Agrobacterium* colonies. A Qiagen Plasmid Max Kit (Qiagen, Cat#12162) is used to extract plasmids from *Agrobacterium* cultures following the manufacture recommended protocol.

*Arabidopsis* Transformation and $T_1$ Selection.

Twelve to fifteen *Arabidopsis* plants (c.v. Columbia) are grown in 4" pots in the green house with light intensity of 250 µmol/m², 25° C., and 18:6 hours of light: dark conditions. Primary flower stems are trimmed one week before transformation. *Agrobacterium* inoculums are prepared by incubating 10 µl of recombinant *Agrobacterium* glycerol stock in 100 ml LB broth (Sigma L3022)+100 mg/L Spectinomycin+50 mg/L Kanamycin at 28° C. and shaking at 225 rpm for 72 hours. *Agrobacterium* cells are harvested and suspended into 5% sucrose+0.04% Silwet-L77 (Lehle Seeds Cat # VIS-02)+10 µg/L benzamino purine (BA) solution to $OD_{600}$ 0.8~1.0 before floral dipping. The above-ground parts of the plant are dipped into the *Agrobacterium* solution for 5-10 minutes, with gentle agitation. The plants are then transferred to the greenhouse for normal growth with regular watering and fertilizing until seed set.

Example 17

Growth and Bioassays of Transgenic *Arabidopsis*

Selection of $T_1$ *Arabidopsis* Transformed with Hairpin RNAi Constructs.

Up to 200 mg of $T_1$ seeds from each transformation is stratified in 0.1% agarose solution. The seeds are planted in germination trays (10.5"×21"×1"; T.O. Plastics Inc., Clearwater, Minn.) with #5 sunshine media. Transformants are selected for tolerance to Ignite® (glufosinate) at 280 g/ha at 6 and 9 days post planting. Selected events are transplanted into 4" diameter pots. Insertion copy analysis is performed within a week of transplanting via hydrolysis quantitative Real-Time PCR (qPCR) using Roche LightCycler480. The PCR primers and hydrolysis probes are designed against DSM2v2 selectable marker using LightCycler Probe Design Software 2.0 (Roche). Plants are maintained at 24° C., with a 16:8 hour light: dark photoperiod under fluorescent and incandescent lights at intensity of 100-150 mE/m2×s.

*E. heros* Plant Feeding Bioassay.

At least four low copy (1-2 insertions), four medium copy (2-3 insertions), and four high copy (≥4 insertions) events are selected for each construct. Plants are grown to a flowering stage (plants containing flowers and siliques). The surface of soil is covered with ~50 ml volume of white sand for easy insect identification. Five to ten $2^{nd}$ instar *E. heros* nymphs are introduced onto each plant. The plants are covered with plastic tubes that are 3" in diameter, 16" tall, and with wall thickness of 0.03" (Item No. 484485, Visipack Fenton MO); the tubes are covered with nylon mesh to isolate the insects. The plants are kept under normal temperature, light, and watering conditions in a conviron. In 14 days, the insects are collected and weighed; percent mortality as well as growth inhibition (1−weight treatment/weight control) are calculated. YFP hairpin-expressing plants are used as controls.

$T_2$ *Arabidopsis* Seed Generation and $T_2$ Bioassays.

$T_2$ seed is produced from selected low copy (1-2 insertions) events for each construct. Plants (homozygous and/or heterozygous) are subjected to *E. heros* feeding bioassay, as described above. $T_3$ seed is harvested from homozygotes and stored for future analysis.

Example 18

Transformation of Additional Crop Species

Cotton is transformed with rpL40 (with or without a chloroplast transit peptide) to provide control of hemipteran insects by utilizing a method known to those of skill in the art, for example, substantially the same techniques previously described in EXAMPLE 14 of U.S. Pat. No. 7,838,733, or Example 12 of PCT International Patent Publication No. WO 2007/053482.

Example 19

RpL40 dsRNA in Insect Management

RpL40 dsRNA transgenes are combined with other dsRNA molecules in transgenic plants to provide redundant RNAi targeting and synergistic RNAi effects. Transgenic plants including, for example and without limitation, corn, soybean, and cotton expressing dsRNA that target rpL40 are useful for preventing feeding damage by coleopteran and hemipteran insects. RpL40 dsRNA transgenes are also combined in plants with *Bacillus thuringiensis* insecticidal protein technology to represent new modes of action in Insect Resistance Management gene pyramids. When combined with other dsRNA molecules that target insect pests, and/or with *Bacillus thuringiensis* insecticidal proteins, in a transgenic plants, a synergistic insecticidal effect is observed that also mitigates the development of resistant insect populations.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

What may be claimed is:

1. An isolated nucleic acid comprising a polynucleotide operably linked to a heterologous promoter, wherein the polynucleotide comprises at least a first nucleotide sequence that is selected from the group consisting of a native coding sequence of a *Diabrotica* organism comprising SEQ ID NO:12; the complement of a native coding sequence of a *Diabrotica* organism comprising SEQ ID NO:12; a fragment of at least 35 contiguous nucleotides of a native coding sequence of a *Diabrotica* organism comprising SEQ ID NO:12; the complement of a fragment of at least 35 contiguous nucleotides of a native coding sequence of a *Diabrotica* organism comprising SEQ ID NO:12; a native coding sequence of a *Diabrotica* organism comprising SEQ ID NO:13; the complement of a native coding sequence of a *Diabrotica* organism comprising SEQ ID NO:13; a fragment of at least 35 contiguous nucleotides of a native coding sequence of a *Diabrotica* organism comprising SEQ ID NO:13; the complement of a fragment of at least 35 contiguous nucleotides of a native coding sequence of a *Diabrotica* organism comprising SEQ ID NO:13; a native coding sequence of a *Diabrotica* organism comprising SEQ ID NO:14; the complement of a native coding sequence of a *Diabrotica* organism comprising SEQ ID NO:14; a fragment of at least 35 contiguous nucleotides of a native coding sequence of a *Diabrotica* organism comprising SEQ ID NO:14; and the complement of a fragment of at least 35 contiguous nucleotides of a native coding sequence of a *Diabrotica* organism comprising SEQ ID NO:14;
  a second nucleotide sequence; and,
  a third nucleotide sequence that is the reverse complement of the first nucleotide sequence, wherein the third nucleotide sequence is linked to the first nucleotide sequence by the second nucleotide sequence.

2. The nucleic acid molecule of claim 1, wherein the *Diabrotica* organism is selected from the group consisting of *D. v. virgifera* LeConte; *D. barberi* Smith and Lawrence; *D. u. howardi*; *D. v. zeae*; *D. balteata* LeConte; *D. u. tenella*; *D. speciosa* Germar; and *D. u. undecimpunctata* Mannerheim.

3. The nucleic acid molecule of claim 1, wherein the molecule is a plant transformation vector.

4. A polynucleotide encoded by the polynucleotide of the nucleic acid molecule of claim 1.

5. A double-stranded ribonucleic acid (dsRNA) molecule comprising the polynucleotide of claim 4.

6. The double-stranded ribonucleic acid molecule of claim 5, wherein contacting the polynucleotide sequence with a coleopteran insect inhibits the expression of an endogenous nucleotide sequence specifically complementary to the polynucleotide.

7. The double-stranded ribonucleic acid molecule of claim 6, wherein contacting said double-stranded ribonucleic acid molecule with a coleopteran kills or inhibits the growth, viability, and/or feeding of the insect.

8. The nucleic acid molecule of claim 1, wherein the heterologous promoter is functional in a plant cell.

9. A cell comprising the nucleic acid molecule of claim 1.

10. The cell of claim 9, wherein the cell is a prokaryotic cell.

11. The cell of claim 9, wherein the cell is a eukaryotic cell.

12. A transgenic plant cell comprising the nucleic acid molecule of claim 1, wherein the heterologous promoter is functional in the plant cell.

13. A transgenic plant material comprising the nucleic acid molecule of claim 8.

14. The transgenic plant material of claim 13, wherein the plant material is a seed or plant.

15. A commodity product produced from the plant of claim 13, wherein the commodity product comprises a detectable amount of the polynucleotide.

16. The transgenic plant cell of claim 12, wherein the cell is a Zea mays cell.

17. The transgenic plant material of claim 13, wherein the plant material is a Zea mays plant material.

18. The transgenic plant or seed of claim 14, wherein the plant or seed is a Zea mays plant or seed.

19. A method for controlling a coleopteran insect population, the method comprising feeding insects of the population with an agent comprising the dsRNA molecule of claim 5.

20. The method according to claim 19, wherein the agent is a transgenic plant material expressing the dsRNA molecule.

21. The method according to claim 19 wherein the agent is a sprayable formulation.

22. The method according to claim 19, wherein the agent is a transgenic plant material expressing the dsRNA molecule.

23. The method according to claim 19, wherein the agent is a sprayable formulation.

24. A method for improving the yield of a crop, the method comprising:
cultivating in the crop the transgenic plant or seed of claim 14, such that the dsRNA molecule is expressed.

25. The method according to claim 24, wherein the plant is Zea mays.

26. A method for producing a transgenic plant cell, the method comprising:
transforming a plant cell with the nucleic acid molecule of claim 8;
culturing the transformed plant cell under conditions sufficient to allow for development of a plant cell culture; and
selecting a transgenic plant cell that has integrated the polynucleotide in its genome and expresses the dsRNA molecule.

27. A method for producing a coleopteran insect resistant transgenic plant, the method comprising:
regenerating a transgenic plant from the transgenic plant cell of claim 12.

28. The nucleic acid molecule of claim 1, further comprising a polynucleotide encoding a polypeptide from *Bacillus thuringiensis*, *Alcaligenes* spp., or *Pseudomonas* spp.

29. The nucleic acid molecule of claim 28, wherein the polynucleotide encodes a polypeptide from *B. thuringiensis* that is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

30. The transgenic plant cell of claim 12, wherein the cell comprises a polynucleotide encoding a polypeptide from *Bacillus thuringiensis*, *Alcaligenes* spp., or *Pseudomonas* spp.

31. The transgenic plant cell of claim 30, wherein the polynucleotide encodes a polypeptide from *B. thuringiensis* that is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

32. The transgenic plant of claim 13, wherein the plant comprises a polynucleotide encoding a polypeptide from *Bacillus thuringiensis*, *Alcaligenes* spp., or *Pseudomonas* spp.

33. The transgenic plant of claim 32, wherein the polynucleotide encodes a polypeptide from *B. thuringiensis* that is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

34. The method according to claim 26, wherein the transgenic plant cell comprises a polynucleotide encoding a polypeptide from *Bacillus thuringiensis*, *Alcaligenes* spp., or *Pseudomonas* spp.

35. The method according to claim 34, wherein the polynucleotide encodes a polypeptide from *B. thuringiensis* that is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

* * * * *